US008198060B2

(12) United States Patent
Williams et al.

(10) Patent No.: US 8,198,060 B2
(45) Date of Patent: Jun. 12, 2012

(54) NEMATODE PHOSPHOETHANOLAMINE N-METHYLTRANSFERASE-LIKE SEQUENCES

(75) Inventors: Deryck J. Williams, St. Louis, MO (US); Merry B. McLaird, Kirkwood, MO (US); Michelle Coutu Hresko, Chesterfield, MO (US); Anita M. Frevert, St. Louis, MO (US); Ronald E. Worthington, St. Louis, MO (US); Andrew P. Kloek, San Francisco, CA (US); Jennifer A. Davila-Aponte, St. Louis, MO (US); John D. Bradley, St. Louis, MO (US); Siqun Xu, Ballwin, MO (US)

(73) Assignee: Divergence, Inc., St. Louis, MO (US)

( * ) Notice: Subject to any disclaimer, the term of this patent is extended or adjusted under 35 U.S.C. 154(b) by 335 days.

(21) Appl. No.: 12/260,071

(22) Filed: Oct. 28, 2008

(65) Prior Publication Data
US 2009/0123986 A1 May 14, 2009

Related U.S. Application Data

(62) Division of application No. 10/602,268, filed on Jun. 23, 2003, now Pat. No. 7,442,533.

(60) Provisional application No. 60/390,490, filed on Jun. 21, 2002.

(51) Int. Cl.
C12N 9/12 (2006.01)
(52) U.S. Cl. ........................................ 435/194; 530/350
(58) Field of Classification Search .................. None
See application file for complete search history.

(56) References Cited

U.S. PATENT DOCUMENTS

| 3,824,233 A | 7/1974 | Friedman | 260/240 |
| 6,165,987 A | 12/2000 | Harvey | 514/30 |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
GenBank Accession No. AAB04824; GI: 1458245, Pauley et al., 2004.
GenBank Accession No. AAA81102; GI: 1055130, Leimbach, 2002.
Andriamampandry et al., "Properties of a partially purified phosphodimethylethanolamine methyltransferase . . . " Biochem, J. 288:267-272, 1992.
Bolognese et al., "The isolation and characterization in yeast of a gene for Arabidopsis S-Adenosylmethionine: . . . " Plant Physiology 124:1800-1813, 2000.
Charron et al., "Molecular and biochemical characterization of a cold-regulated phosphoethanolamine . . . " Plant Physiology 129:363-373, 2002.
De Rudder et al., "Plant-exuded choline is used for rhizobial membrane lipid biosynthesis by . . . " J. of Biol. Chem 272(28):20011-20016, 1999.
Hanada et al., "A gene encoding phosphatidylethanolamine N-methyltransferase from Acetobacter aceti and . . . " Biosci. Biotech. Biochem 65(12):2741-2748, 2001.
Kanipes et al., "The phospholipids methyltransferases in yeast" Biochemica et Biophysica Acta 1348:134-141, 1997.
Lopez-Lara et al., "Novel pathway for phosphatidylcholine biosynthesis in bacteria associated with eukaryotes" J. of Biotech. 91:211-221, 2001.
McNeil et al., "Enhanced synthesis of choline and glycine betaine in transgenic tobacco plants." PNAS 98(17):10001-10005, 2001.
Mukherjee et al., "Partial purification of a phosphoethanolamine methyltransferase from rat brain cytosol" Neurochem. Res. 20(10):1233-1237, 1995.
Nuccio et al., "cDNA cloning of phosphoethanolamine N-methyltransferase from spinach by complementation . . . " J. of Biol. Chem. 275(19):14095-14101, 2000.
Sheard et al., "Plasma choline concentration in humans fed parenterally" Amer. J. of Clin. Nutrician 43:219-224, 1986.
Tayek et al., "Abnormal liver function in malnourished patients receiving total parenteral nutrician:" J. of Amer. College of Nutrician 9(1):76-83, 1990.
Vance et al., "Phosphatidylethanolamine N-methyltransferase from liver" Biochemica et Biophysica Acta 1348:142-150, 1997.
GenBank Accession No. T27936; GI: 7511249; Leimbach, D., Mar. 2000.
GenBank Accession No. AA038583; GI: 28275059; Wilson, R., May 2003.
GenBank Accession No. AAL00881; GI: 15487647; Wilson, R., May 2003.
GenBank Accession No. BI744289; GI: 15766091; McCarter, J., Sep. 2001.
GenBank Accession No. BM284222; GI: 17993264; McCarter, J., Dec. 2001.
GenBank Accession No. BG227205; GI:12714760; McCarter, J., May 2001.
GenBank Accession No. CB016194; GI: 27590930; Blaxter, M.L., Jan. 2003.
GenBank Accession No. AW097500; GI: 6067811; McCarter, J., May 2001.
GenBank Accession No. BI500593; GI: 15339937; McCarter, J., Aug. 2001.
Genbank Accession No. AW114998; GI:6081336; McCarter, J., May 2001.
GenBank Accession No. AI987127; GI: 5816211; McCarter, J., May 2001.
GenBank Accession No. BQ625256; GI: 21652426; McCarter, J., Jul. 2002.

(Continued)

Primary Examiner — Richard Hutson
(74) Attorney, Agent, or Firm — Fish & Richardson P.C.

(57) ABSTRACT

Nucleic acid molecules from nematodes encoding phosphoethanolamine n-methyltransferase polypeptides are described. PEAMT-like polypeptide sequences are also provided, as are vectors, host cells, and recombinant methods for production of PEAMT-like nucleotides and polypeptides. Also described are screening methods for identifying inhibitors and/or activators, as well as methods for antibody production.

3 Claims, 8 Drawing Sheets

OTHER PUBLICATIONS

GenBank Accession No. BI142998; GI: 14624708; McCarter, J., Jul. 2001.
GenBank Accession No. BE238954; GI: 9033918; Dautova, M., Jul. 2000.
GenBank Accession No. BM343328; GI: 18080101; McCarter, J., Jan. 2002.
GenBank Accession No. BI594600; GI: 15498087; Blaxter, M.L., Sep. 2001.
GenBank Accession No. BM282649; GI: 17991691; McCarter, J., Dec. 2001.
GenBank Accession No. BM517436; GI: 18688588; McCarter, J., Feb. 2002.
GenBank Accession No. BM283632; GI: 17992674; McCarter, J., Dec. 2001.
GenBank Accession No. BM517415; GI: 18688567; McCarter, J., Feb. 2002.
GenBank Accession No. BM319736; GI: 18054078; McCarter, J., Jan. 2002.
GenBank Accession No. BM567173; GI: 18828817; McCarter, J., Feb. 2002.
GenBank Accession No. BM517116; GI: 18688268; McCarter, .J., Feb. 2002.
GenBank Accession No. BM319312; GI: 18053654; McCarter, J., Jan. 2002.
GenBank Accession No. BM283359; GI: 17992401; McCarter, J., Dec. 2001.
GenBank Accession No. BM282721; GI: 17991763; McCarter, J., Dec. 2001.
GenBank Accession No. BM283536; GI: 17992578; McCarter, J., Dec. 2001.
GenBank Accession No. BM518439; GI: 18689591; McCarter, J., Feb. 2002.
GenBank Accession No. BM517603; GI: 18688755; McCarter, J., Feb. 2002.
GenBank Accession No. BM517738; GI: 18688890; McCarter, J., Feb. 2002.
GenBank Accession No. BM515217; GI: 18686360; McCarter, J., Feb. 2002.
GenBank Accession No. BM284413; GI: 17993455; McCarter, J., Dec. 2001.
GenBank Accession No. BM283081; GI: 17992123; McCarter, J., Dec. 2001.
UniProtKB Accession No. Q23552: Leimbach, D., Nov. 1995.
UniProtKB Accession No. Q22993; Pauley et al., Jul. 1996.
Palavalli et al., "Defining the Role of Phosphomethylethanolamine N-Methyltransferase from *Caenorhabditis elegans* in . . ." Biochemistry 45:6056-6065, 2006.
Ngo et al., The Protein Folding Problem and Tertiary Structure Prediction, 1994, Merz et al. (ed), Birkhauser, Boston, MA pp. 433 and 492-495.

* cited by examiner

```
1
gggtttaattacccaagtttgagagaataaaaggtgaata ATG ACC GAA GCA ATT CGA CGC TCT TCT TTC AAA AAT TTC TGG TCG
                                          M   T   E   A   I   R   R   S   S   F   K   N   F   W   S
86
AAA TTT TCG CAT CGT TGT GAT AAT ACA GTA ATG ATG TTG AAT AAA AGC GCC GAT GAA TTT GAA GCC GAT GAT CGT
K   F   S   H   R   C   D   N   T   V   M   M   L   N   K   S   A   D   E   F   E   A   D   D   R
161
GCA GAT ATT ATA TCT TCA TTA CCC GAT CTA CAT GGC AAG GAT ATT GTC GAT ATT GGC GCT GGA ATT GGA CGT TTC
A   D   I   I   S   S   L   P   D   L   H   G   K   D   I   V   D   I   G   A   G   I   G   R   F
236
ACG ACA ATT TTC GCA CAT GAT GCA CGT CAT GTA CTA TCA TGC GAT TTT ATC GAA AGT TTC ATG GCA AAA AAT AAA
T   T   I   F   A   H   D   A   R   H   V   L   S   C   D   F   I   E   S   F   M   A   K   N   K
311
GAA CGG AAT GCG CAT TTC TCT AAT ATC TCT TAT CAG GTT GGC GAT GCG GTA CAT TTA CAA CTC GAT CCA AAC AGT
E   R   N   A   H   F   S   N   I   S   Y   Q   V   G   D   A   V   H   L   Q   L   D   P   N   S
386
GTA GAC CTT GTG TTC ACG AAC TGG CTC ATG ATG TAC CTC AGC GAT GAT GAA GTT ATT CGC TTT CTT CTC AAC GCA
V   D   L   V   F   T   N   W   L   M   M   Y   L   S   D   D   E   V   I   R   F   L   L   N   A
461
CTC CGA TGG CTT CGT CCT AAC GGC TAT TTG CAC CTT CGA GAG TCA TGC AGC CAA CCG TCA ACC GCA CGA GTT GGA
L   R   W   L   R   P   N   G   Y   L   H   L   R   E   S   C   S   Q   P   S   T   A   R   V   G
536
GGA ACG ATG CAT AAT AGT ACA GAG ATA AAT CCA ACC AGC TAT CGA CTA TCC TCT GAG TAT ATA AAA TTG CTA AGG
G   T   M   H   N   S   T   E   I   N   P   T   S   Y   R   L   S   S   E   Y   I   K   L   L   R
611
AAT ATT CGT TAT CGT GAA TTA GAT GGC ACA TTA TTT CGC TTC GAA GTG CAT TGG GCT TGT TCA GTG CCC ACT TAT
N   I   R   Y   R   E   L   D   G   T   L   F   R   F   E   V   H   W   A   C   S   V   P   T   Y
686
ATC GTC GTG CAA AAT AAT TGG CGT CAA GTT CAT TGG TTA ACG CAA AAA GTT CGA TGC AAC GAT GAT GCG ATA ATG
I   V   V   Q   N   N   W   R   Q   V   H   W   L   T   Q   K   V   R   C   N   D   D   A   I   M
761
TCT ATC GAA CAC CTT CTC GGA CAT TTT AGT ACA CTA TGG AAG GTG GAG CAA CAA AAG TGG GAT CGT TAC CTC GAC
S   I   E   H   L   L   G   H   F   S   T   L   W   K   V   E   Q   Q   K   W   D   R   Y   L   D
836
AAT GAA TCC TAT TGC TGG ACT GAT GAG GTG TTT GGC TAT GCG TTA ATG AAG GAA ACG ATT GAG AGT ATG CCC GCA
N   E   S   Y   C   W   T   D   E   V   F   G   Y   A   L   M   K   E   T   I   E   S   M   P   A
911
GTA TTG GCA TAT AAT CCT CGC AAA TTG GCC TAT CAT TTG CAT ATA AAT GCG CAT CGC ATT TCT GAG ATG TTA CAT
V   L   A   Y   N   P   R   K   L   A   Y   H   L   H   I   N   A   H   R   I   S   E   M   L   H
986 e
TGT AAT GTT GTA TGG AAT GTG GAG ATA AAT GAA TTT TTC TAT CGG ACA TCA TTA ACG AAA GCA AAT CGC CTC AAA
C   N   V   V   W   N   V   E   I   N   E   F   F   Y   R   T   S   L   T   K   A   N   R   L   K
1061
GAT CAA CGA GTT CGA TTT GGA TGG AAT GCT ACG CTT GAA TCG TCG CTG AAT TAT TGG AAA GAA CGT GGT GCT CTC
D   Q   R   V   R   F   G   W   N   A   T   L   E   S   S   L   N   Y   W   K   E   R   G   A   L
1136
TTC GAT ATT TTT ATC GCC ACT GAA TTT TTC ACC GAT CTC GAT GAA AGT ACC ATC GAT AAG CTC TCC GTG GTA TTA
F   D   I   F   I   A   T   E   F   F   T   D   L   D   E   S   T   I   D   K   L   S   V   V   L
1211
AAA GCG GAT GCA CCT CTA ATT CTG CTG GAG CCA TTT GAC GAA TCA GCT TAT GAT GAG AAA TAC ATC ATG AAG TTG
K   A   D   A   P   L   I   L   L   E   P   F   D   E   S   A   Y   D   E   K   Y   I   M   K   L
1286
TTA TCA CGT TAT CAA CAA ATT TCT ATC GAG GAT ATC ACT GAG ATG TGC ACA GAA GCG ATT CAT AAA TAT CTA AGC
L   S   R   Y   Q   Q   I   S   I   E   D   I   T   E   M   C   T   E   A   I   H   K   Y   L   S
1361
GAA AGA GAT TTA GAG AAT AAT ATT GGA ACA AAA GTA TGG AAA TTA ATA AAA GCG CAT ATG tgattgaatttttacgaaaa
E   R   D   L   E   N   N   I   G   T   K   V   W   K   L   I   K   A   H   M
1441
aaacgacgacgacgatgattcctatgaatgtttttatctgacgctgcaaacgatgaatatacgattgtcataaattgagaatatgagaatattgtcggct
1541
taatgcatatattggcaacatataaactgtgtgttttataaaaaaaaaaaaaaaaagtactagtcgacgcgtggccaagggcgaattctgcagatatcc
1641
atcacactggcggccgctcgagcatgcatctagagggcccaattcgccctatagtgagtcgtattacaattcactggccgtcgttttacaacgtcgtgac
1741
tgggaaaaccctggcgttacccaacttaattcgccttgcagcacat
```

FIGURE 1

```
1
ggttttaacccagtatctcaagagca ATG ACG GCT GAG GTG CGA CGG GAT TCC TTC AAG ACG TTC TGG GAC AAG TAC TCA
                           M   T   A   E   V   R   R   D   S   F   K   T   F   W   D   K   Y   S
81
GAT AAA CCC GAC ACT AAT TCG ATG ATG CTC AAC CAG ACT GCA CAA GAT CTG GAA GCT AGC GAT AGA GCA GAT ATC
D   K   P   D   T   N   S   M   M   L   N   Q   T   A   Q   D   L   E   A   S   D   R   A   D   I
156
CTC TCC AGC CTA CCT CAC CTA ACC AAC AAA GAC GTG GTC GAT ATT GGC GCT GGA ATC GGG CGC TTC ACT ACT GTG
L   S   S   L   P   H   L   T   N   K   D   V   V   D   I   G   A   G   I   G   R   F   T   T   V
231
CTA GCA GAA ACT GCT CGA TGG GTT CTT TCA ACG GAT TTC ATC GAA TCG TTC ATC GAA AAA AAT CAA GAA CGA AAT
L   A   E   T   A   R   W   V   L   S   T   D   F   I   E   S   F   I   E   K   N   Q   E   R   N
306
GCT CAC ATG GGT AAC ATC AGT TAT CAA ATA GGA GAC GCA GTC CAT TTG CAA ATG GAC GAG AAA AGC GTG GAT CTC
A   H   M   G   N   I   S   Y   Q   I   G   D   A   V   H   L   Q   M   D   E   K   S   V   D   L
381
GTT TTT ACG AAT TGG TTG ATG ATG TAT CTC TCC GAT CGT GAA GTC ATT GAA TTT CTG CTG AAT GCT ATG CGA TGG
V   F   T   N   W   L   M   M   Y   L   S   D   R   E   V   I   E   F   L   L   N   A   M   R   W
456
TTG AGA GCG GAC GGA TAC ATT CAT CTC AGA GAA AGC TGC TCC GAG CCA AGC ACG GGC CGT CTG AAG ACC GCC ACA
L   R   A   D   G   Y   I   H   L   R   E   S   C   S   E   P   S   T   G   R   L   K   T   A   T
531
ATG CAC TCA GCC GTT GAC GCC AAC CCA ACA CAT TAC CGT TTC TCA TCG CTG TAT ATC AAG CTT CTT CGA GCA ATC
M   H   S   A   V   D   A   N   P   T   H   Y   R   F   S   S   L   Y   I   K   L   L   R   A   I
606
CGA TAC GGG GAC AGT GAT GGA AAA ATG TGG AAA TTT GAT GTG CAG TGG AGC TGC TCG GTG CCC ACC TAC ATA CGG
R   Y   G   D   S   D   G   K   M   W   K   F   D   V   Q   W   S   C   S   V   P   T   Y   I   R
681
AGG TGC AAT AAC TGG CGT CAA GTG CAT TGG TTG ACG AAG AAG GTA CCG GCA GTT GGC GAC GAA GAG ACT TCA GTC
R   C   N   N   W   R   Q   V   H   W   L   T   K   K   V   P   A   V   G   D   E   E   T   S   V
756
GAC GAT TTG CTC AAC TTG TTC AGC CAG ATC TGG CCA GCC GAA CAA AAG ACG TGG GAT GAA AAA CTA GAC AAT GAA
D   D   L   L   N   L   F   S   Q   I   W   P   A   E   Q   K   T   W   D   E   K   L   D   N   E
831
AAA TAC AGT TGG ACT GAT AAG ATA TTC TCG AAT GCG ATC GAT GAT GAA GTG GTG CCA AAG AAC AGT ACC GCC TAT
K   Y   S   W   T   D   K   I   F   S   N   A   I   D   D   E   V   V   P   K   N   S   T   A   Y
906
GTC TTC ACA CCA AGG CAA CGA TCC CCC TTC TTG CAC GTC AAC TCG CAC CTT TTG GCA GAG AAG TTC ACA TGC AAT
V   F   T   P   R   Q   R   S   P   F   L   H   V   N   S   H   L   L   A   E   K   F   T   C   N
981
GTA TGG AAT GTT GAA ACA AAA GAG TAT TTG TAT CGT ACT TCG TTG ACG AAG GCA AAC AAC CAG AAG GAC CAA CGA
V   W   N   V   E   T   K   E   Y   L   Y   R   T   S   L   T   K   A   N   N   Q   K   D   Q   R
1056
GTG CGC TTC GGT TGG AAC GAG TCC TTG TCT TCG CCC ATC GAC TAC TGG AAT CAG AGG GAC GCT TCA TTT GAC TGC
V   R   F   G   W   N   E   S   L   S   S   P   I   D   Y   W   N   Q   R   D   A   S   F   D   C
1131
ATG GTA GCA ACT GAA CTT CTC GCG ACT TGT GAT GAT GAG AGC GTA AAG AGT ATT GCG AGC ATT ATG AAA CCA GAA
M   V   A   T   E   L   L   A   T   C   D   D   E   S   V   K   S   I   A   S   I   M   K   P   E
1206
GCG AAG GTG GTG CTC CTC GAA CCA GTT AGC GGA ATT GAC GAG ACG TCC GTT AGG CAG CGA ATG ACT ACT TGT GGG
A   K   V   V   L   L   E   P   V   S   G   I   D   E   T   S   V   R   Q   R   M   T   T   C   G
1281
TTC AAA AAC ATT ACC ATC GTC GAT GTT ACA CAG GAG TCC TTG AAC GCC GAG GTT TCT TTC ATT AAG GAC CAC AAC
F   K   N   I   T   I   V   D   V   T   Q   E   S   L   N   A   E   V   S   F   I   K   D   H   N
1356
TTG GAC GTC GAA CTC TCT GGT TGT AAT TAC CTA CTG ATC AAG GCT TCA CTT taatgcaacatagtaaggaacggatgatttct
L   D   V   E   L   S   G   C   N   Y   L   L   I   K   A   S   L
1439
ttttatacgtcacttttatgaaataagcctttggacattgattacggtgttgtgagattttttctgctgcatttgtcatctgtatggttttgattttactg
1539
aagttatttgtccaactcatttgaaattgtaaaaaataaccccctcaatcgaagaaatttgtaccggtgacttaataaaactttttttctcgctcaaaaaaa
1639
aaaaaaaaaaagtactagtcgacgcgtggcc
```

FIGURE 2

```
1
gggtttaattacccaagtttgagcaattgaatat ATG CGG ATG CGA CTG GAG CAC GAG GAC ACT GAC ATG GAC TGG AGG CAA
                                    M   R   M   R   L   E   H   E   D   T   D   M   D   W   R   Q
83
ATT TAT CAC TCC TTT TGG AAC AAA TTT TCC GAT AGG GCT GAC AAT ACA TCC ATG CTT TTA AAT GCG GAT GCT GAT
 I   Y   H   S   F   W   N   K   F   S   D   R   A   D   N   T   S   M   L   L   N   A   D   A   D
158
AAA TTT GAA GCT CTT GAC AGA GCC GAA ATT ATC GGA ATG TTG CCC TCT TTT AAA AAT AAA TTT GTT GTG GAT ATT
 K   F   E   A   L   D   R   A   E   I   I   G   M   L   P   S   F   K   N   K   F   V   V   D   I
233
GGG GCG GGT ATT GGA AGA TTC ACA ACA GAA TTT GCC AAA AAG GCA AGA GAA GTG GTC TCA ACA GAT TTT GTA GCT
 G   A   G   I   G   R   F   T   T   E   F   A   K   K   A   R   E   V   V   S   T   D   F   V   A
308
AGC TTT ATC GAG AAA AAT CGG GAA ACA AAT ATA GCC TTT AAT AAC ATT GAA TGG AGA GTT GGT GAT GCT GTA AGA
 S   F   I   E   K   N   R   E   T   N   I   A   F   N   N   I   E   W   R   V   G   D   A   V   R
383
TTA GAT TTT GAA GAG GGG AGT ATT GAT ATA GTC TTT ACC AAT TGG CTT TTG ATG TAT TTA GTG GAT GAA GAA GTT
 L   D   F   E   E   G   S   I   D   I   V   F   T   N   W   L   L   M   Y   L   V   D   E   E   V
458
GTT CAA TTT TTG ATT AAT GCC ATT AAA TGG CTC AGG CCT GGC GGT TAT TTA CAT TTG AGA GAG TCC TGC TCT GAA
 V   Q   F   L   I   N   A   I   K   W   L   R   P   G   G   Y   L   H   L   R   E   S   C   S   E
533
CCT AGC AGC AAA AAA TCT AAT AAT TCG CTA CAT TCC AAT TCG GAT AGT ATC AAT CCA ACT AAA TAT CGC TTT TCA
 P   S   S   K   K   S   N   N   S   L   H   S   N   S   D   S   I   N   P   T   K   Y   R   F   S
608
TCC GCA TAT ATT CAA TTG CTC AAA TCA ATT AAT TTT AAA AGC GGA GAT GGA ACC GTT TGG GGG TTT AAA ATC CAC
 S   A   Y   I   Q   L   L   K   S   I   N   F   K   S   G   D   G   T   V   W   G   F   K   I   H
683
TGG GCT AGC TCT GTT AAT GTT TAT ATT CAA AAA AAT GCA AAT TGG AGA CAA GTG CAT TGG TTA GTA AGC AAG GTT
 W   A   S   S   V   N   V   Y   I   Q   K   N   A   N   W   R   Q   V   H   W   L   V   S   K   V
758
CCT AAA AAG GAA AAA TTT ATG CCA AAT TTG GGT ACA CTG CTT GGA GAG AAG TGG CCT GAA GAG CAG AAG GAA TGG
 P   K   K   E   K   F   M   P   N   L   G   T   L   L   G   E   K   W   P   E   E   Q   K   E   W
833
GAC AAT AAA CTT GAC TTG GCT TTG AAT GAG AAT CAG AAT ATC ACC TCA ACT CTA GCC AGT TAT CTT TTA TCT AGT
 D   N   K   L   D   L   A   L   N   E   N   Q   N   I   T   S   T   L   A   S   Y   L   L   S   S
908
GGG ATT GGA ACA AAT TCA GTT ATA CTT GTT TTC GAC TTG AGA AAT AGT GAA AAT CAG CCC AGT ATT AAT GTT CAC
 G   I   G   T   N   S   V   I   L   V   F   D   L   R   N   S   E   N   Q   P   S   I   N   V   H
983
ACA TTG GCT AAC AGA TTA AAT TCA AAT ATT TGG TCT GTT TCC CTC AAT CCT TTC TGC TTC CGT CAT TCA TTA ACC
 T   L   A   N   R   L   N   S   N   I   W   S   V   S   L   N   P   F   C   F   R   H   S   L   T
1058
CTT GCT AAT AAT AAC CAA GAT CGA CGG ATT AGA CAC TCT TGG CAT GAG GAT ATT GAA AGC GCT TTC CAC TTT TTG
 L   A   N   N   N   Q   D   R   R   I   R   H   S   W   H   E   D   I   E   S   A   F   H   F   L
1133
GGT GAA CAA ATA TCC GGC AAA GAG AAA AAT ATC AGC AGA TTA TTT GAT GTG ATT ATT GGT ATT GGT TTG TTA GAA
 G   E   Q   I   S   G   K   E   K   N   I   S   R   L   F   D   V   I   I   G   I   G   L   L   E
1208
AAA ATT AAA AAA ATG AAG GAC GCT AGC GAG AAA GTT GAG AAA ATC CTT GGC CGT TAT TTG TTA AGT ATT GAA ACA
 K   I   K   K   M   K   D   A   S   E   K   V   E   K   I   L   G   R   Y   L   L   S   I   E   T
1283
GGC GAA GGA GAT GAT ATA CGA AAG GAA AAA AAG AAT GAG GAC ATT GTA GAA TAT TTC CCA TCA GAA CTA TTT ACA
 G   E   G   D   D   I   R   K   E   K   K   N   E   D   I   V   E   Y   F   P   S   E   L   F   T
1358
AAA CAA ACA ATA GAA TTC AAA GCA GAT AAT GGA TTT AAT CAG CTT GAT tagaattggaaaaagagaaaaattgtgaacaaaaaa
 K   Q   T   I   E   F   K   A   D   N   G   F   N   Q   L   D
1442
aaaaaaaaaaagtactagtcgacgcgtggcc
```

FIGURE 3

```
1
  tttataaaacccagtttgagtaccgttttattattttaag ATG GAG GGT GAA AAT GAT AGA CAG AAT TTT CTT GAA TAT TGG
                                            M   E   G   E   N   D   R   Q   N   F   L   E   Y   W
84
AGA CAA TTT GGC AAT ATA GCT AAT ATC AAT GGT ATG ATG CTT AAT GCT AAT GCT TCT TTA ATT GAG AAA AAT GAT
 R   Q   F   G   N   I   A   N   I   N   G   M   M   L   N   A   N   A   S   L   I   E   K   N   D
159
AGG CAT GAT GTA TGT CTA TTA CTT CCT GAT TTA AAA GGA AAA ACT GTT TTA GAT GCT GGT GCT GGA ATT GGA CGT
 R   H   D   V   C   L   L   L   P   D   L   K   G   K   T   V   L   D   A   G   A   G   I   G   R
234
TTT ACT GCT GAA CTT GCT GAA AGG GCT GAA AAA GTT TAT GCA TCA GAT TTT ATT TCT GAA TAT GTT ACT AAA TTA
 F   T   A   E   L   A   E   R   A   E   K   V   Y   A   S   D   F   I   S   E   Y   V   T   K   L
309
CAA GAA CTT AGT GCT GAA GCG TTA AAA AAT GGA AAA ATT ATT GAT GTT ACA GTA GCA GAT GCT ACA TGT CTT TCT
 Q   E   L   S   A   E   A   L   K   N   G   K   I   I   D   V   T   V   A   D   A   T   C   L   S
384
TAT CCA GAG AAT AGT TAT TTC CTT GTT TTT ACT AAT TGG TTG TTT ATG TAT TTT AAT AAT ACT GAA TGT GTA CGT
 Y   P   E   N   S   Y   F   L   V   F   T   N   W   L   F   M   Y   F   N   N   T   E   C   V   R
459
TTT ACT GTA AAT GCA TTA AAA TGG TTA GAA GAA GGT GGA TAT TTT AAA TTA AGA GAA TCA TGT TCT GAA CCA TCA
 F   T   V   N   A   L   K   W   L   E   E   G   G   Y   F   K   L   R   E   S   C   S   E   P   S
534
ACA AGA AGA GTT GGA AAT AGA AAT GAA ACT TCT CTT CAT GCT GCC GTT CAA TCA AAT CCA ACT GAA TAT AGA TTT
 T   R   R   V   G   N   R   N   E   T   S   L   H   A   A   V   Q   S   N   P   T   E   Y   R   F
609
TCA TCT GTT TAT CTT AAA TTA ATT GAA GCA GCT AGA TAC GTT GAT TCA AAT AAT CAA AAA TGG AAA TTC GAA ATA
 S   S   V   Y   L   K   L   I   E   A   A   R   Y   V   D   S   N   N   Q   K   W   K   F   E   I
684
GAA ATT TGT GGT TCT ATT CCA ACA TAC ATT TTA AAT GGT AAT ACT TGG AGA CAA GTA CAG TTA ATT GCT AAA AAA
 E   I   C   G   S   I   P   T   Y   I   L   N   G   N   T   W   R   Q   V   Q   L   I   A   K   K
759
GTA AAA GCA GAT GAT AAT GAT GTT GTT TTA TCC CAA GAT GAG TTG AAA AAT TTA ATG ACT AAT GAT TGG ATA ATG
 V   K   A   D   D   N   D   V   V   L   S   Q   D   E   L   K   N   L   M   T   N   D   W   I   M
834
GAA CAA AAA AAG ACT GAT TCT ATT GTT GAT GGT AGA GTA CAA TAT TTT GCT GAT AAA ATT TTT GCT AAT GAA TTA
 E   Q   K   K   T   D   S   I   V   D   G   R   V   Q   Y   F   A   D   K   I   F   A   N   E   L
909
TCA AAT ATT GAT ATG ACT AAT ACT GAA TCC ATT TCA TCA ATA TTT GTT TTC CAA TCT TCA TTT AAT CCA TGG TAC
 S   N   I   D   M   T   N   T   E   S   I   S   S   I   F   V   F   Q   S   S   F   N   P   W   Y
984
AAA AGA ATT TTC CCA TTT TCT TTA GCA TCA AAT AAA TAT TGC CAT GTC TGG ACA AAT GAG GGT AAT CGT GAA CTT
 K   R   I   F   P   F   S   L   A   S   N   K   Y   C   H   V   W   T   N   E   G   N   R   E   L
1059
TTT AGA TGT TCA TTA ACT TCA GCT AAT GAA GAA AGA AAT ATT GGA ATG TTT TTT ACC TAT TCA AAA GAC AAT GTT
 F   R   C   S   L   T   S   A   N   E   E   R   N   I   G   M   F   F   T   Y   S   K   D   N   V
1134
TTT AAT GCC TTA GAT TAC GTT AAA AAA AGA AAC TTT TTA TTA AAC AGT TTT CTA GCT ATT GAC TAT TTA AAT AAT
 F   N   A   L   D   Y   V   K   K   R   N   F   L   L   N   S   F   L   A   I   D   Y   L   N   N
1209
CAT GAA GTT AAT TTT ATT GAA TCA TTT AAT AAT ATT GCT TCT CAA GAT GCT AAA ATT CTC CTT CTT GAA TCA TTT
 H   E   V   N   F   I   E   S   F   N   N   I   A   S   Q   D   A   K   I   L   L   L   E   S   F
1284
TCA AAT GAG GAT GAA AAA AAT TTA AAA TTA AGT AAA CTT AAT AAG CAA TAC ACA GTA AAG TGC GTA ACA GAA AAC
 S   N   E   D   E   K   N   L   K   L   S   K   L   N   K   Q   Y   T   V   K   C   V   T   E   N
1359
GTT CAT AAT GAA GTT AAA AAT GTA CAT CAA GAT GAA GAA ATT GTA TGT GAC GTT ACA TCG AAA AAA TGG ATG CTT
 V   H   N   E   V   K   N   V   H   Q   D   E   E   I   V   C   D   V   T   S   K   K   W   M   L
1434
ATC AAT GTA AAC CAT taatatcattcatcaagtaatgttatctaacaacgtaattttttttattgactcttaaaattcattatttttttaatta
 I   N   V   N   H
1529
aaatattattttacaaaaaaaatggcttaatatttcttttaataaattaag
```

FIGURE 4

```
1
gggtttaattacccaagtttgagggtggtgcagcgaactacgcagccataaacggtgag ATG CCT GCG GCA GAG CGT GAA CTA ATC AGT
                                                            M   P   A   A   E   R   E   L   I   S
90
GCA TTA TTC GAC GTT ACA CCG AAA GAT GCT CTT ACA AGT GTA CTC TTG GTC ACC TCT GCC CAA TCA GAG GAA AGC
A   L   F   D   V   T   P   K   D   A   L   T   S   V   L   L   V   T   S   A   Q   S   E   E   S
165
AAT TCA TCA CTG GTT GCA CTC TTT GAG GAC AGA GCA ATT AAC GTA ACC ATC GTT GAG CGT CTT GAG GGA TTG CAA
N   S   S   L   V   A   L   F   E   D   R   A   I   N   V   T   I   V   E   R   L   E   G   L   Q
240
AGC ACT CGA GCT GAC GCA TAT GAC GCC ATT ATC AGC AAT AAA TTG ATC GTC GAG AAC TGT TTA ATC AAT AAA CCA
S   T   R   A   D   A   Y   D   A   I   I   S   N   K   L   I   V   E   N   C   L   I   N   K   P
315
TCA GAT CTC GAT ACA TTC GTC GCA TCG GCT CTA AAA GAA GAA GGT GTA CTC ATC GTT CGT GAA GAC CTA AAT GGT
S   D   L   D   T   F   V   A   S   A   L   K   E   E   G   V   L   I   V   R   E   D   L   N   G
390
TGT TCT GCG TGT GAG AAG GTC GCT CAG CTA ACG CAT TTC TTT GAT CTG TTT CGA ACA ACT CTG AAC GGC GTT ACG
C   S   A   C   E   K   V   A   Q   L   T   H   F   F   D   L   F   R   T   T   L   N   G   V   T
465
ATT GGC TTC AAA TTC TAT TCA CTC AAG CAA GTC AAT GCC TCA ATT CAT ACC GAA GGA AAC TTT CTG GAT GTC TTC
I   G   F   K   F   Y   S   L   K   Q   V   N   A   S   I   H   T   E   G   N   F   L   D   V   F
540
TGG ATA TTG CGG AAA GAA TGT TTC GAA GCG CTG GAC GAG AAC CAA AAA ACA AAA ACC TTT CGT GAT TTT CTC GAT
W   I   L   R   K   E   C   F   E   A   L   D   E   N   Q   K   T   K   T   F   R   D   F   L   D
615
ACT ACG CAA TAC ACT GAC GAG AGC ATA CGT GCA TAT GAA TGG ATC TTC GGC GAT AAC TTC ATC AGT CCG GGC GGT
T   T   Q   Y   T   D   E   S   I   R   A   Y   E   W   I   F   G   D   N   F   I   S   P   G   G
690
TAT GAC GAA AAC TTA GAA GTT CTG AAG CGA TTC GGT GAT CTA AAA CCG GAT TGT AAA ATG CTC GAC ATC GGT GTT
Y   D   E   N   L   E   V   L   K   R   F   G   D   L   K   P   D   C   K   M   L   D   I   G   V
765
GGG ATC GGT GGA GGT GCC CGC CAG GCT GCT AGG GAA TTC GGA GCG CTG GTT CTC GGT ATG GAT ATT AGT GCG AAT
G   I   G   G   G   A   R   Q   A   A   R   E   F   G   A   L   V   L   G   M   D   I   S   A   N
840
ATG CTT TCA ATA GCG ATG GAT CGC CTA CAG AAT GAG AAA GAC ACT CGC GTT CGT TAT CAA ATA TCC GAC GCT CTC
M   L   S   I   A   M   D   R   L   Q   N   E   K   D   T   R   V   R   Y   Q   I   S   D   A   L
915
GAA TAT GAG TTT CCA GCC AAC TCG TTT GAT TAC GTT TTC AGT CGT GAC GGT TTA CAT CAT AAC GAG CGC ATC GAC
E   Y   E   F   P   A   N   S   F   D   Y   V   F   S   R   D   G   L   H   H   N   E   R   I   D
990
ATC GTA ATG CGA AAG ATT TTC CAC TGG TTG AAA CCT GGT GGG AAA GTG CTC ATC ACG GTG TAT GGC ATG GGC CAT
I   V   M   R   K   I   F   H   W   L   K   P   G   G   K   V   L   I   T   V   Y   G   M   G   H
1065
GGG ACA TTA AGC GCG AAA TTC CAA GCC TAT GTG GAA AAG AGG AAA TAT TTT CTG AAG ACA CTC GAA GAG ATG GTT
G   T   L   S   A   K   F   Q   A   Y   V   E   K   R   K   Y   F   L   K   T   L   E   E   M   V
1140
GAG ATA ACT GAA GCT GCT GGA TTC GAA AAT GTG CAA GGG ACA AAC CTC ACC AAG CGA TTC CGC GAT ATA CTG CTC
E   I   T   E   A   A   G   F   E   N   V   Q   G   T   N   L   T   K   R   F   R   D   I   L   L
1215
GAC GAG CGG ACA AAA ACG CTG AAC CGA AAA AAC GAA TTC CTT GAG AAA TTC GAT GAA GGA ACA TTC AAC AGC CTC
D   E   R   T   K   T   L   N   R   K   N   E   F   L   E   K   F   D   E   G   T   F   N   S   L
1290
TTG AAC GGA TGG AAT GAT AAG ATC GGC TTT ATC GAC GAC GAT AAC CAT AAT TGG AAT CAG ATC TTC GCA ACA AAA
L   N   G   W   N   D   K   I   G   F   I   D   D   D   N   H   N   W   N   Q   I   F   A   T   K
1365
CCA CTT TAG aagttcctcttttttgaccggttgatcgacgtcaacagcagcgcttgaacaacactcaactatgtcttctactaaatgctgcaaatt
P   L   *
1462
cttgcatgggcagtgctgtccgttcatcacttgcaggttattaaaactttgtaaagttaaatatagcttgt
```

FIGURE 5

```
1
gggtttaattacccaagtttgagattttttttcaaaaaattttaaaataataaa ATG AGT GCA TTA TCT TGT GAA TTA GCT TAT GCA
                                                        M   S   A   L   S   C   E   L   A   Y   A
89
CTT CAA AAT CAT CCA AAT GCA CCC AAA AAT GGC GAA ACT GTT CTC TTA TTA ATT AAC GAT CAA GAT GTT AAT GAA
L   Q   N   H   P   N   A   P   K   N   G   E   T   V   L   L   L   I   N   D   Q   D   V   N   E
164
AGG AAT TTA AAT TCT GAT CTA AGA AAT TTA TTC GAA GAT AAA TTT AAT TTG GAG GAG ATG GAT ATT GGA GAG TTG
R   N   L   N   S   D   L   R   N   L   F   E   D   K   F   N   L   E   E   M   D   I   G   E   L
239
ATA AAT ATA TCA GAA CGT TTA GAT AAA GAA GAT AAT GAC AAC GAA GAA GAG AAT TTA GAA ACA CGT TTT GAT GCT
I   N   I   S   E   R   L   D   K   E   D   N   D   N   E   E   E   N   L   E   T   R   F   D   A
314
GCT ATT TGC TCT AAT TTA TTT ATT GGA CAA GGA ATT GTA AAT GAC CGT CAT CGT ATT GCT CAA GTA TTA GGA TTA
A   I   C   S   N   L   F   I   G   Q   G   I   V   N   D   R   H   R   I   A   Q   V   L   G   L
389
CTT CTT CGT TTA ATA CGG ACA GAT GGA GTT GTA ATT ATT AGA GAA AAT CTA AAG CAA TGG GGT TCT CGT TCA ATT
L   L   R   L   I   R   T   D   G   V   V   I   I   R   E   N   L   K   Q   W   G   S   R   S   I
464
GCT GAT TTA ACT AAA TTT CTT GAT GTT TTT GCT TTT CGA AAA CAA CAA AAT AAT CAA AAA CAA CAA CAA ACA CTT
A   D   L   T   K   F   L   D   V   F   A   F   R   K   Q   Q   N   N   Q   K   Q   Q   Q   T   L
539
GGA TTT AAT TTT TAT GGA ATG AGC CAA GTA CAG GAC AGC ATT TAT GCA CAT TCT AAT TTT CTT GAC GTT TTT TGG
G   F   N   F   Y   G   M   S   Q   V   Q   D   S   I   Y   A   H   S   N   F   L   D   V   F   W
614
AGC TTA ACA ACA GCT ATT GAA GTT AGA TTA TAT GAT GAT AAA TTA GCT ACT TTT AGG GAA TTT TTG GAT AAA ACA
S   L   T   T   A   I   E   V   R   L   Y   D   D   K   L   A   T   F   R   E   F   L   D   K   T
689
CAG TAT ACT GAG GAC AAC GTT GCT AGT TAT GAG TGG ATA TTT GGG ACA GAT TTT ATC AGC CCA GGT GGA GTG AAT
Q   Y   T   E   D   N   V   A   S   Y   E   W   I   F   G   T   D   F   I   S   P   G   G   V   N
764
GAA AAT AGA AGA GTA CTA AAA TAT TTC CGT CAT TTA CGT CCA GGA CAA CAA ATG CTT GAT ATT GGT GTT GGA ATT
E   N   R   R   V   L   K   Y   F   R   H   L   R   P   G   Q   Q   M   L   D   I   G   V   G   I
839
GGT GGA GGA GCT AGA CAA GCT GCT AGG GAG TTT GGT CTT CAA GTA CTT GGT TGT GAT CTT TCT TCA AAT ATG ATT
G   G   G   A   R   Q   A   A   R   E   F   G   L   Q   V   L   G   C   D   L   S   S   N   M   I
914
CAA CAT GCT TTT GAT CGT AAT CAA CGT GAC AAA GAT CAT CGT GTT GAA TAT CAA ATT GCT GAT GCT ATG GTT TAT
Q   H   A   F   D   R   N   Q   R   D   K   D   H   R   V   E   Y   Q   I   A   D   A   M   V   Y
989
CGT TAT GAA TCT AAT GCT TTT GAT ATT GTA TTT AGT AGA GAT TGT ATT CAA CAT ATT AAA GAT ACA AAA AGA TTA
R   Y   E   S   N   A   F   D   I   V   F   S   R   D   C   I   Q   H   I   K   D   T   K   R   L
1064
TTT AGA AAT ATT TAT ACT TGG CTT AAA CCA GGT GGA CAA GTA CTT GTT ACA ATG TAT GGG AAA GGA CAT GGA GTT
F   R   N   I   Y   T   W   L   K   P   G   G   Q   V   L   V   T   M   Y   G   K   G   H   G   V
1139
CTC TCG CCA AAA TTT CAT GAA TAT GTT CGT AAA CGG CAA TAT GCA CTA AAA ACT TTA GAA GAA TAT AGA GAA ATT
L   S   P   K   F   H   E   Y   V   R   K   R   Q   Y   A   L   K   T   L   E   E   Y   R   E   I
1214
GCT CAT AAT GTT GGT TTA ACA ACT ATT TAC ACA GAA AAT ATG ACT AAA CGT TTG AGA GAA ATT TTA GTA ATT GAA
A   H   N   V   G   L   T   T   I   Y   T   E   N   M   T   K   R   L   R   E   I   L   V   I   E
1289
CGT GAT AGA GCA GTT GAA AAT AAA GAA GAA TTT ATT CAA AAA TTT AGT GAA AAA CTT TAT TCA AAA TTA ATT GAG
R   D   R   A   V   E   N   K   E   E   F   I   Q   K   F   S   E   K   L   Y   S   K   L   I   E
1364
GGT TGG GCA GAT AAA TTA CAA TTT ATT GAT GAA GAT AAC CAA AAT TGG TTG TTA CTT CGT GCG GAG AAA CCG GTG
G   W   A   D   K   L   Q   F   I   D   E   D   N   Q   N   W   L   L   R   A   E   K   P   V
1439
CAT CCG CAT GCT TAT TTA ACT GAA GCT GGA GCT taaaacaaattatttaagacaagaaaataaagagaagaaaatttttttaatttttt
H   P   H   A   Y   L   T   E   A   G   A
1528
tatatca
```

FIGURE 6

```
C_elegans_a    ...MSTDQQ......SSVEDQTVAMVNVRRANFKSFWDKYSDKPDTNSMMLNHSAEELES: 51
C_elegans_b    MDRYSPYDKTVFLIFCTAYILQKAMVNVRRANFKSFWDKYSDKPDTNSMMLNHSAEELES: 60
H_contortus    ..............................MTAEVRRDSFKTFWDKYSDKPDTNSMMLNQTAQDLEA: 37
A_summ         ..............................MTEAIRRSSFKNFWSKPSHRCDNTVMMLNKSADEFEA: 37
M_incognita    ...............MRMRLEHEDTDMDWRQIYHSFWNKFSDRADNTSMLLNADADKFEA: 45
S_stercoralis  ...................MEGENDRQNFLEYWRQFGNIANINGMMLNANASLIEK: 37

C_elegans_a    SDRADILASLPLLHNKDVVDIGAGIGRFTTVLAETARWVLSTDFIDSPIKKNQERNAHLG:111
C_elegans_b    SDRADILASLPLLHNKDVVDIGAGIGRFTTVLAETARWVLSTDFIDSPIKKNQERNAHLG:120
H_contortus    SDRADILSSLPHLTNKDVVDIGAGIGRFTTVLAETARWVLSTDFIESPIEKNQERNAHMG: 97
A_summ         DDRADIISSLPDLHGKDIVDIGAGIGRFTTIFAHDARHVLSCDFIESFMAKNKERNAHFS: 97
M_incognita    LDRAEIIGMLPSFKNKFVVDIGAGIGRFTTEFAKKAREVVSTDPVASPIEKNRETNIAPN:105
S_stercoralis  NDRHDVCLLLPDLKGKTVLDAGAGIGRFTAELAERAEKVYASDFISEYVTKLQELSAEAL: 97

C_elegans_a    N....INYQVGDAVGLKMESNSVDLVFTNWLMMYLSDEETVEFIPNCMRWLRSHGIVHLR:167
C_elegans_b    N....INYQVGDAVGLKMESNSVDLVFTNWLMMYLSDEETVEFIPNCMRWLRSHGIVHLR:176
H_contortus    N....ISYQIGDAVHLQMDEKSVDLVFTNWLMMYLSDREVIEFLLNAMRWLRADGYIHLR:153
A_summ         N....ISYQVGDAVHLQLDPNSVDLVFTNWLMMYLSDDEVIRPLLNALRWLRPNGYLHLR:153
M_incognita    N....IEWRVGDAVRLDFEEGSIDIVFTNWLLMYLVDEEVVQFLINAIKWLRPGGYLHLR:161
S_stercoralis  KNGKIIDVTVADATCLSYPENSYPLVFTNWLPMYPNNTECVRPTVNALKWLEEGGYFKLR:157

C_elegans_a    ESCSEPSTGRS...KAKSMHDTANANPTHYRFSSLYINLLRAIRYRDVDNKLWRPNVQWS:224
C_elegans_b    ESCSEPSTGRS...KAKSMHDTANANPTHYRFSSLYINLLRAIRYRDVDNKLWRPNVQWS:233
H_contortus    ESCSEPSTGRL...KTATMHSAVDANPTHYRFSSLYIKLLRAIRYGDSDGKMWKFDVQWS:210
A_summ         ESCSQPSTAR....VGGTMHNSTEINPTSYRLSSEYIKLLRNIRYRELDGTLPRPEVHWA:209
M_incognita    ESCSEPSSKKS...NNSLHSNSDSINPTKYRFSSAYIQLLKSINFKSGDGTVWGFKIHWA:218
S_stercoralis  ESCSEPSTRRVGNRNETSLHAAVQSNPTEYRFSSVYLKLIEAARYVDSNNQKWRFEIEIC:217

C_elegans_a    CSVPTYIKRSNNWRQVHWLAEKVPAEDGAKGTSFNELVELIKNTWQNEQEAWDAKLD...:281
C_elegans_b    CSVPTYIKRSNNWRQVHWLAEKVPAEDGAKGTSFNELVELIKNTWQNEQEAWDAKLD...:290
H_contortus    CSVPTYIRRCNNWRQVHWLTKKVPAVGDEE.TSVDDLLNLFSQIWPAEQKTWDEKLD...:266
A_summ         CSVPTYIVVQNNWRQVHWLTQKVRCNDDAI.MSIEHLLGHFSTLWKVEQQKWDRYLD...:265
M_incognita    SSVNVYIQKNANWRQVHWLVSKVPKKE....KPMPNLGTLLGEKWPEEQKEWDNKLDLAL:274
S_stercoralis  GSIPTYILNGNTWRQVQLIAKKVKADDNDVVLSQDELKNLMTNDWIMEQKKTDSIVD...:274

C_elegans_a    DEKYVWTDKVFSSALT.....SLPSNSTFFLYTPRTVSPYCHINAHTLAETFNAN.VWNT:335
C_elegans_b    DEKYVWTDKVFSSALT.....SLPSNSTFFLYTPRTVSPYCHINAHTLAETFNAN.VWNT:344
H_contortus    NEKYSWTDKIFSNAIDDE...VVPKNSTAYVFTPRQRSPFLHVNSHLLAEKFTCN.VWNV:322
A_summ         NESYCWTDEVFGYALMKE...TIESMPAVLAYNPRKLAYHLHINAHRISEMLHCNVVWNV:322
M_incognita    NENQNITSTLASYLLSS....GIGTNSVILVPDLRNSENQPSINVHTLANRLNSN.IWSV:329
S_stercoralis  GRVQYFPADKIFANELSNIDMTNTESISSIFVFQSSPNPWYKRIPPFSLASNKYCH.VWTN:333

C_elegans_a    EIIPEYYRTSLTKSNNLKDQRVRFGWN.QSLTDSVTYWQQKDALFDVPVATEPLSTVDDE:394
C_elegans_b    EIIPEYYRTSLTKSNNLKDQRVRFGWN.QSLTDSVTYWQQKDALFDVPVATEPLSTVDDE:403
H_contortus    ETKEYLYRTSLTKANNQKDQRVRFGWN.ESLSSPIDYWNQRDASPDCMVATELLATCDDE:381
A_summ         EINEPYYRTSLTKANRLKDQRVRFGWN.ATLESSLNYWKERGALPDIFIATEPFTDLDES:381
M_incognita    SLNPFCFRHSLTLANNNQDRRIRHSWH.EDIESAFHFLGEQISGKEKNISRLFDVIIGIG:388
S_stercoralis  EGNRELPRCSLTSANEERNIGMPFTYSKDNVFNALDYVKKRNFLLNSPLAIDYLNNHEVN:393

C_elegans_a    TIRQLPNVMSDGAKFITLEP..VDEVNEAEMKQRIQELGYTLKSFTDVTDQCIEAQEQYF:452
C_elegans_b    TIRQLPNVMSDGAKFITLEP..VDEVNEAEMKQRIQELGYTLKSFTDVTDQCIEAQEQYF:461
H_contortus    SVKSIASIMKPEAKVVLLEP..VSGIDETSVRQRMTTCGFPKNITIVDVTQESLNAEVSPI:439
A_summ         TIDKLSVVLKADAPLILLEP..FDESAYDEKYIMKLLSRYQQISIEDITEMCTEAIHKYL:439
M_incognita    LLEKIKKMKDASEKVEKILGRYLLSIETGEGDDIRKEKKNEDIVEYFPSELFTKQTIEFK:448
S_stercoralis  FIESFNNIASQDAKILLLES..FSNEDE...RNLKLSKLNKQYTVKCVTENVHNEVKNVH:448

C_elegans_a    KDHEQLRDEKVIRKNWVLLELTH:475
C_elegans_b    KDHEQLRDEKVIRKNWVLLELTH:484
H_contortus    KDHN..LDVELSGCNYLLIKASL:460
A_summ         SERD..LENNIGTKVWKLIKAHM:460
M_incognita    ADNG..........FNQLD...:457
S_stercoralis  QDEE..IVCDVTSKKWMLINVNH:469
```

FIGURE 7

```
A_suum      MP..AAERELISALFDVTPKDALTSVLLVTSAQSEES..NSSLVALFEDRA........I: 48
C_elegans   MSSLSIPRQSLYYVNKVTEGRSVSNVQVVSPCQKQ....GQTYVTAFTPLT........S: 48
M_javanica  MSALSCELAYALQNHPNAPKNGETVLLLINDQDVNERNLNSDLRNLFEDKFNLEEMDIGE: 60

A_suum      NVTIVERLEGLQSTRA......DAYDAIISNKLIVENCLIN..KPSDLDTFVASALKEEG:100
C_elegans   NVQVHTSLEQLSTIR.......NADVLIFNNALSQIITNAD..LLTDFLKNATNATAIGG: 99
M_javanica  LINISERLDKEDNDNEEENLETRFDAAICSNLFIGQGIVNDRHRIAQVLGLLLRLIRTDG:120

A_suum      VLIVREDLNGCSACEKVAQLTHFFDLFRTT.LNGV.....TIGFKFYSLKQVNASIHTEG:154
C_elegans   TVIIREDLKDCSDKRQVARLTDYFDVFRTTDSDGN.....NTGLDLYTVDQVEHSNYVEQ:154
M_javanica  VVIIRENLKQWGS.RSIADLTKFLDVFAFRKQQNNQKQQQTLGFNFYGMSQVQDSIYAHS:179

A_suum      NFLDVFWILRKECFEALDENQKTKTFRDFLDTTQYTDESIRAYEWIFGDNFISPGGYDEN:214
C_elegans   NFLDFIFVFRKKVFAPTTD..ATITFRDFLDKTQYTNTGIDAYEWMFGVNFISPGGYDEN:212
M_javanica  NFLDVFWSLTTAIEVRLYDD.KLATFREFLDKTQYTEDNVASYEWIFGTDFISPGGVNEN:238

A_suum      LEVLKRFGDLKPDCKMLDIGVGIGGGARQAAREFGALVLGMDISANMLSIAMDRLQNEKD:274
C_elegans   LKIIKRFGDFKPGQTMLDIGVGIGGGARQVADEFGVHVHGIDLSSNMLAIALERLHEEKD:272
M_javanica  RRVLKYFRHLRPGQQMLDIGVGIGGGARQAAREFGLQVLGCDLSSNMIQHAFDRNQRDKD:298

A_suum      TRVRYQISDALEYEFPANSFDYVFSRDGLHHNERIDIVMRKIFHWLKPGGKVLITVYGMG:334
C_elegans   SRVKYSITDALVYQFEDNSFDYVFSRDCIQHIPDTEKLFSRIYKALKPGGKVLITMYGKG:332
M_javanica  HRVEYQIADAMVYRYESNAFDIVFSRDCIQHIKDTKRLFRNIYTWLKPGGQVLVTMYGKG:358

A_suum      HGTLSAKFQAYVEKRKYFLKTLEEMVEITEAAGFENVQGTNLTKRFRDILLDERTKTLNR:394
C_elegans   YGEQSDKFKTYVAQRAYFLKNLKEIADIANKTGFVNVQTENMTPRFKEILLEERGHLEQN:392
M_javanica  HGVLSPKFHEYVRKRQYALKTLEEYREIAHNVGLTTIYTENMTKRLREILVIERDRAVEN:418

A_suum      KNEFLEKFDEGTFNSLLNGWNDKIGFIDDDNHNWNQIFATKPL............:437
C_elegans   EAEFMSKFTQRERDSLISGWTDKLGYIEKDNHNWNFFLAQKPFPK.........:437
M_javanica  KEEFIQKFSEKLYSKLIEGWADKLQFIDEDNQNWLLLRAEKPVHPHAYLTEAGA:472
```

FIGURE 8

```
SEQUENCE LISTING

<160> NUMBER OF SEQ ID NOS: 46

<210> SEQ ID NO 1
<211> LENGTH: 1786
<212> TYPE: DNA
<213> ORGANISM: Ascaris suum

<400> SEQUENCE: 1
gggtttaatt acccaagttt gagagaataa aaggtgaata atgaccgaag caattcgacg     60
ctcttctttc aaaaatttct ggtcgaaatt ttcgcatcgt tgtgataata cagtaatgat    120
gttgaataaa agcgccgatg aatttgaagc cgatgatcgt gcagatatta tatcttcatt    180
acccgatcta catggcaagg atattgtcga tattggcgct ggaattggac gtttcacgac    240
aattttcgca catgatgcac gtcatgtact atcatgcgat tttatcgaaa gtttcatggc    300
aaaaaataaa gaacggaatg cgcatttctc taatatctct tatcaggttg gcgatgcggt    360
acatttacaa ctcgatccaa acagtgtaga ccttgtgttc acgaactggc tcatgatgta    420
cctcagcgat gatgaagtta ttcgctttct tctcaacgca ctccgatggc ttcgtcctaa    480
cggctatttg caccttcgag agtcatgcag ccaaccgtca accgcacgag ttggaggaac    540
```

```
gatgcataat agtacagaga taaatccaac cagctatcga ctatcctctg agtatataaa    600
attgctaagg aatattcgtt atcgtgaatt agatggcaca ttatttcgct tcgaagtgca    660
ttgggcttgt tcagtgccca cttatatcgt cgtgcaaaat aattggcgtc aagttcattg    720
gttaacgcaa aaagttcgat gcaacgatga tgcgataatg tctatcgaac accttctcgg    780
acattttagt acactatgga aggtggagca acaaaagtgg gatcgttacc tcgacaatga    840
atcctattgc tggactgatg aggtgtttgg ctatgcgtta atgaaggaaa cgattgagag    900
tatgcccgca gtattggcat ataatcctcg caaattggcc tatcatttgc atataaatgc    960
gcatcgcatt tctgagatgt acattgtaa tgttgtatgg aatgtggaga taaatgaatt    1020
tttctatcgg acatcattaa cgaaagcaaa tcgcctcaaa gatcaacgag ttcgatttgg    1080
atggaatgct acgcttgaat cgtcgctgaa ttattggaaa gaacgtggtg ctctcttcga    1140
tatttttatc gccactgaat ttttcaccga tctcgatgaa agtaccatcg ataagctctc    1200
cgtggtatta aaagcggatg cacctctaat tctgctggag ccatttgacg aatcagctta    1260
tgatgagaaa tacatcatga agttgttatc acgttatcaa caaatttcta tcgaggatat    1320
cactgagatg tgcacagaag cgattcataa atatctaagc gaaagagatt tagagaataa    1380
tattggaaca aaagtatgga aattaataaa agcgcatatg tgattgaatt tttacgaaaa    1440
aaacgacgac gacgatgatt cctatgaatg ttttatctg acgctgcaaa cgatgaatat    1500
acgattgtca taaattgaga atatgagaat attgtcggct taatgcatat attggcaaca    1560
tataaactgt gtgttttata aaaaaaaaaa aaaaaagta ctagtcgacg cgtggccaag    1620
ggcgaattct gcagatatcc atcacactgg cggccgctcg agcatgcatc tagagggccc    1680
aattcgccct atagtgagtc gtattacaat tcactggccg tcgttttaca acgtcgtgac    1740
tgggaaaacc ctggcgttac ccaacttaat tcgccttgca gcacat                  1786

<210> SEQ ID NO 2
<211> LENGTH: 1669
<212> TYPE: DNA
<213> ORGANISM: Haemonchus contortus

<400> SEQUENCE: 2
ggttttaacc cagtatctca agagcaatga cggctgaggt gcgacgggat tccttcaaga    60
cgttctggga caagtactca gataaacccg acactaattc gatgatgctc aaccagactg   120
cacaagatct ggaagctagc gatagagcag atatcctctc cagcctacct cacctaacca   180
acaaagacgt ggtcgatatt ggcgctgaa tcgggcgctt cactactgtg ctagcagaaa   240
ctgctcgatg ggttctttca acggatttca tcgaatcgtt catcgaaaaa aatcaagaac   300
gaaatgctca catgggtaac atcagttatc aaataggaga cgcagtccat ttgcaaatgg   360
acgagaaaag cgtggatctc gttttttacga attggttgat gatgtatctc tccgatcgtg   420
aagtcattga atttctgctg aatgctatgc gatggttgag agcggacgga tacattcatc   480
tcagagaaag ctgctccgag ccaagcacgg gccgtctgaa gaccgccaca atgcactcag   540
ccgttgacgc caacccaaca cattaccgtt tctcatcgct gtatatcaag cttcttcgag   600
caatccgata cggggacagt gatggaaaaa tgtggaaatt tgatgtgcag tggagctgct   660
cggtgcccac ctacatacgg aggtgcaata actggcgtca agtgcattgg ttgacgaaga   720
aggtaccggc agttggcgac gaagagactt cagtcgacga tttgctcaac ttgttcagcc   780
agatctggcc agccgaacaa aagacgtggg atgaaaaact agacaatgaa aaatacagtt   840
ggactgataa gatattctcg aatgcgatcg atgatgaagt ggtgccaaag aacagtaccg   900
```

-continued

| | |
|---|---|
| cctatgtctt cacaccaagg caacgatccc ccttcttgca cgtcaactcg cacctttgg | 960 |
| cagagaagtt cacatgcaat gtatggaatg ttgaaacaaa agagtatttg tatcgtactt | 1020 |
| cgttgacgaa ggcaaacaac cagaaggacc aacgagtgcg cttcggttgg aacgagtcct | 1080 |
| tgtcttcgcc catcgactac tggaatcaga gggacgcttc atttgactgc atggtagcaa | 1140 |
| ctgaacttct cgcgacttgt gatgatgaga gcgtaaagag tattgcgagc attatgaaac | 1200 |
| cagaagcgaa ggtggtgctc ctcgaaccag ttagcggaat tgacgagacg tccgttaggc | 1260 |
| agcgaatgac tacttgtggg ttcaaaaaca ttaccatcgt cgatgttaca caggagtcct | 1320 |
| tgaacgccga ggtttctttc attaaggacc acaacttgga cgtcgaactc tctggttgta | 1380 |
| attacctact gatcaaggct tcactttaat gcaacatagt aaggaacgga tgatttcttt | 1440 |
| ttatacgtca ctttatgaa ataagccttt ggacattgat tacggtgttg tgagattttt | 1500 |
| ctgctgcatt tgtcatctgt atggttttga ttttactgaa gttatttgtc caactcattt | 1560 |
| gaaattgtaa aaataacccc ctcaatcgaa gaaatttgta ccggtgactt aataaaactt | 1620 |
| ttttctcgct caaaaaaaaa aaaaaaaag tactagtcga cgcgtggcc | 1669 |

<210> SEQ ID NO 3
<211> LENGTH: 1472
<212> TYPE: DNA
<213> ORGANISM: Meloidogyne incognita

<400> SEQUENCE: 3

| | |
|---|---|
| gggtttaatt acccaagttt gagcaattga atatatgcgg atgcgactgg agcacgagga | 60 |
| cactgacatg gactggaggc aaatttatca ctccttttgg aacaaatttt ccgataggc | 120 |
| tgacaataca tccatgcttt taaatgcgga tgctgataaa tttgaagctc ttgacagagc | 180 |
| cgaaattatc ggaatgttgc cctcttttaa aaataaattt gttgtggata ttggggcggg | 240 |
| tattggaaga ttcacaacag aatttgccaa aaaggcaaga gaagtggtct caacagattt | 300 |
| tgtagctagc tttatcgaga aaaatcggga aacaaatata gcctttaata acattgaatg | 360 |
| gagagttggt gatgctgtaa gattagattt tgaagagggg agtattgata tagtctttac | 420 |
| caattggctt ttgatgtatt tagtggatga agaagttgtt caattttga ttaatgccat | 480 |
| taaatggctc aggcctggcg gttatttaca tttgagagag tcctgctctg aacctagcag | 540 |
| caaaaaatct aataattcgc tacattccaa ttcggatagt atcaatccaa ctaaatatcg | 600 |
| cttttcatcc gcatatattc aattgctcaa atcaattaat tttaaaagcg gagatggaac | 660 |
| cgtttggggg tttaaaatcc actgggctag ctctgttaat gtttatattc aaaaaaatgc | 720 |
| aaattggaga caagtgcatt ggttagtaag caaggttcct aaaaaggaaa aatttatgcc | 780 |
| aaatttgggt acactgcttg gagagaagtg gcctgaagag cagaaggaat gggacaataa | 840 |
| acttgacttg gctttgaatg agaatcagaa tatcacctca actctagcca gttatctttt | 900 |
| atctagtggg attggaacaa attcagttat acttgttttc gacttgagaa atagtgaaaa | 960 |
| tcagcccagt attaatgttc acacattggc taacagatta aattcaaata tttggtctgt | 1020 |
| ttccctcaat cctttctgct tccgtcattc attaacccctt gctaataata accaagatcg | 1080 |
| acggattaga cactcttggc atgaggatat tgaaagcgct ttccactttt tgggtgaaca | 1140 |
| aatatccggc aaagagaaaa atatcagcag attatttgat gtgattattg gtattggttt | 1200 |
| gttagaaaaa attaaaaaaa tgaaggacgc tagcgagaaa gttgagaaaa tccttggccg | 1260 |
| ttatttgtta agtattgaaa caggcgaagg agatgatata cgaaggaaa aaagaatga | 1320 |
| ggacattgta gaatatttcc catcagaact atttacaaaa caaacaatag aattcaaagc | 1380 |

| | |
|---|---|
| agataatgga tttaatcagc ttgattagaa ttggaaaaag agaaaaattg tgaacaaaaa | 1440 |
| aaaaaaaaaa aagtactagt cgacgcgtgg cc | 1472 |

<210> SEQ ID NO 4
<211> LENGTH: 1580
<212> TYPE: DNA
<213> ORGANISM: Strongyloides stercoralis

<400> SEQUENCE: 4

| | |
|---|---|
| tttataaaac ccagtttgag taccgttttt attattttaa gatggagggt gaaaatgata | 60 |
| gacagaattt tcttgaatat tggagacaat ttggcaatat agctaatatc aatggtatga | 120 |
| tgcttaatgc taatgcttct ttaattgaga aaaatgatag gcatgatgta tgtctattac | 180 |
| ttcctgattt aaaaggaaaa actgttttag atgctggtgc tggaattgga cgttttactg | 240 |
| ctgaacttgc tgaaagggct gaaaaagttt atgcatcaga ttttatttct gaatatgtta | 300 |
| ctaaattaca agaacttagt gctgaagcgt taaaaaatgg aaaaattatt gatgttacag | 360 |
| tagcagatgc tacatgtctt tcttatccag agaatagtta tttccttgtt tttactaatt | 420 |
| ggttgtttat gtattttaat aatactgaat gtgtacgttt tactgtaaat gcattaaaat | 480 |
| ggttagaaga aggtggatat tttaaattaa gagaatcatg ttctgaacca tcaacaagaa | 540 |
| gagttggaaa tagaaatgaa acttctcttc atgctgccgt tcaatcaaat ccaactgaat | 600 |
| atagattttc atctgtttat cttaaattaa ttgaagcagc tagatacgtt gattcaaata | 660 |
| atcaaaaatg gaaattcgaa atagaaattt gtggttctat tccaacatac attttaaatg | 720 |
| gtaatacttg gagacaagta cagttaattg ctaaaaaagt aaaagcagat gataatgatg | 780 |
| ttgttttatc ccaagatgag ttgaaaaatt taatgactaa tgattggata atggaacaaa | 840 |
| aaaagactga ttctattgtt gatggtagag tacaatattt tgctgataaa attttgcta | 900 |
| atgaattatc aaatattgat atgactaata ctgaatccat ttcatcaata tttgttttcc | 960 |
| aatcttcatt taatccatgg tacaaaagaa ttttcccatt ttctttagca tcaaataaat | 1020 |
| attgccatgt ctggacaaat gagggtaatc gtgaactttt tagatgttca ttaacttcag | 1080 |
| ctaatgaaga aagaaatatt ggaatgtttt ttacctattc aaaagacaat gttttaatg | 1140 |
| ccttagatta cgttaaaaaa agaaactttt tattaaacag ttttctagct attgactatt | 1200 |
| taaataatca tgaagttaat tttattgaat catttaataa tattgcttct caagatgcta | 1260 |
| aaattctcct tcttgaatca ttttcaaatg aggatgaaaa aaatttaaaa ttaagtaaac | 1320 |
| ttaataagca atacacagta aagtgcgtaa cagaaaacgt tcataatgaa gttaaaaatg | 1380 |
| tacatcaaga tgaagaaatt gtatgtgacg ttacatcgaa aaaatggatg cttatcaatg | 1440 |
| taaaccatta atatcattca tcaagtaatg ttatctaaca acgtaatttt ttttattgac | 1500 |
| tcttaaaatt cattatttt tttaattaaa atattatttt acaaaaaaaa tggcttaata | 1560 |
| tttctttta ataaattaag | 1580 |

<210> SEQ ID NO 5
<211> LENGTH: 1533
<212> TYPE: DNA
<213> ORGANISM: Ascaris suum

<400> SEQUENCE: 5

| | |
|---|---|
| gggtttaatt acccaagttt gagggtggtg cagcgaacta cgcagccata acggtgaga | 60 |
| tgcctgcggc agagcgtgaa ctaatcagtg cattattcga cgttacaccg aaagatgctc | 120 |
| ttacaagtgt actcttggtc acctctgccc aatcagagga aagcaattca tcactggttg | 180 |

-continued

| | |
|---|---|
| cactctttga ggacagagca attaacgtaa ccatcgttga gcgtcttgag ggattgcaaa | 240 |
| gcactcgagc tgacgcatat gacgccatta tcagcaataa attgatcgtc gagaactgtt | 300 |
| taatcaataa accatcagat ctcgatacat tcgtcgcatc ggctctaaaa gaagaaggtg | 360 |
| tactcatcgt tcgtgaagac ctaaatggtt gttctgcgtg tgagaaggtc gctcagctaa | 420 |
| cgcatttctt tgatctgttt cgaacaactc tgaacggcgt tacgattggc ttcaaattct | 480 |
| attcactcaa gcaagtcaat gcctcaattc ataccgaagg aaactttctg gatgtcttct | 540 |
| ggatattgcg gaaagaatgt ttcgaagcgc tggacgagaa ccaaaaaaca aaaacctttc | 600 |
| gtgattttct cgatactacg caatacactg acgagagcat acgtgcatat gaatggatct | 660 |
| tcggcgataa cttcatcagt ccgggcggtt atgacgaaaa cttagaagtt ctgaagcgat | 720 |
| tcggtgatct aaaaccggat tgtaaaatgc tcgacatcgg tgttgggatc ggtggaggtg | 780 |
| cccgccaggc tgctagggaa ttcggagcgc tggttctcgg tatggatatt agtgcgaata | 840 |
| tgcttttcaat agcgatggat cgcctacaga atgagaaaga cactcgcgtt cgttatcaaa | 900 |
| tatccgacgc tctcgaatat gagtttccag ccaactcgtt tgattacgtt ttcagtcgtg | 960 |
| acggtttaca tcataacgag cgcatcgaca tcgtaatgcg aaagattttc cactggttga | 1020 |
| aacctggtgg gaaagtgctc atcacggtgt atggcatggg ccatgggaca ttaagcgcga | 1080 |
| aattccaagc ctatgtggaa aagaggaaat attttctgaa gacactcgaa gagatggttg | 1140 |
| agataactga agctgctgga ttcgaaaatg tgcaagggac aaacctcacc aagcgattcc | 1200 |
| gcgatatact gctcgacgag cggacaaaaa cgctgaaccg aaaaaacgaa ttccttgaga | 1260 |
| aattcgatga aggaacattc aacagcctct tgaacggatg gaatgataag atcggcttta | 1320 |
| tcgacgacga taaccataat tggaatcaga tcttcgcaac aaaaccactt tagaagttcc | 1380 |
| tctttttttg accggttgat cgacgtcaac agcagcgctt gaacaacact caactatgtc | 1440 |
| ttctactaaa tgctgcaaat tcttgcatgg ggcagtgctg tccgttcatc acttgcaggt | 1500 |
| tattaaaact ttgtaaagtt aaatatagct tgt | 1533 |

<210> SEQ ID NO 6
<211> LENGTH: 1534
<212> TYPE: DNA
<213> ORGANISM: Meloidogyne javanica

<400> SEQUENCE: 6

| | |
|---|---|
| gggtttaatt acccaagttt gagatttttt tttcaaaaaa ttttaaaata ataaaatgag | 60 |
| tgcattatct tgtgaattag cttatgcact tcaaaatcat ccaaatgcac caaaaatgg | 120 |
| cgaaactgtt ctcttattaa ttaacgatca agatgttaat gaaggaatt taaattctga | 180 |
| tctaagaaat ttattcgaag ataaatttaa tttggaggag atggatattg gagagttgat | 240 |
| aaatatatca gaacgtttag ataaagaaga taatgacaac gaagaagaga atttagaaac | 300 |
| acgttttgat gctgctattt gctctaattt atttattgga caaggaattg taaatgaccg | 360 |
| tcatcgtatt gctcaagtat taggattact tcttcgttta atacggacag atggagttgt | 420 |
| aattattaga gaaaatctaa agcaatgggg ttctcgttca attgctgatt taactaaatt | 480 |
| tcttgatgtt tttgcttttc gaaaacaaca aaataatcaa aacaacaac aaacacttgg | 540 |
| atttaattt tatggaatga gccaagtaca ggacagcatt tatgcacatt ctaattttct | 600 |
| tgacgttttt tggagcttaa caacagctat tgaagttaga ttatatgatg ataaattagc | 660 |
| tacttttagg gaattttgg ataaaacaca gtatactgag gacaacgttg ctagttatga | 720 |
| gtggatattt gggacagatt ttatcagccc aggtggagtg aatgaaaata gaagagtact | 780 |

-continued

```
aaaatatttc cgtcatttac gtccaggaca acaaatgctt gatattggtg ttggaattgg    840
tggaggagct agacaagctg ctagggagtt tggtcttcaa gtacttggtt gtgatctttc    900
ttcaaatatg attcaacatg cttttgatcg taatcaacgt gacaaagatc atcgtgttga    960
atatcaaatt gctgatgcta tggtttatcg ttatgaatct aatgcttttg atattgtatt   1020
tagtagagat tgtattcaac atattaaaga tacaaaaaga ttatttagaa atatttatac   1080
ttggcttaaa ccaggtggac aagtacttgt tacaatgtat gggaaaggac atggagttct   1140
ctcgccaaaa tttcatgaat atgttcgtaa acggcaatat gcactaaaaa ctttagaaga   1200
atatagagaa attgctcata atgttggttt aacaactatt tacacagaaa atatgactaa   1260
acgtttgaga gaaattttag taattgaacg tgatagagca gttgaaaata agaagaatt    1320 tattcaaaaa tttagtgaaa aactttattc aaaattaatt gagggttggg cagataaatt   1380
acaatttatt gatgaagata accaaaattg gttgttactt cgtgcggaga aaccggtgca   1440
tccgcatgct tatttaactg aagctggagc ttaaaacaaa ttatttaaga caagaaaata   1500
aagagaagaa aattttttta attttttat atca                                1534
```

<210> SEQ ID NO 7
<211> LENGTH: 460
<212> TYPE: PRT
<213> ORGANISM: Ascaris suum

<400> SEQUENCE: 7

```
Met Thr Glu Ala Ile Arg Arg Ser Ser Phe Lys Asn Phe Trp Ser Lys
  1               5                  10                  15

Phe Ser His Arg Cys Asp Asn Thr Val Met Met Leu Asn Lys Ser Ala
             20                  25                  30

Asp Glu Phe Glu Ala Asp Arg Ala Asp Ile Ile Ser Ser Leu Pro
         35                  40                  45

Asp Leu His Gly Lys Asp Ile Val Asp Ile Gly Ala Gly Ile Gly Arg
     50                  55                  60

Phe Thr Thr Ile Phe Ala His Asp Ala Arg His Val Leu Ser Cys Asp
 65                  70                  75                  80

Phe Ile Glu Ser Phe Met Ala Lys Asn Lys Glu Arg Asn Ala His Phe
                 85                  90                  95

Ser Asn Ile Ser Tyr Gln Val Gly Asp Ala Val His Leu Gln Leu Asp
            100                 105                 110

Pro Asn Ser Val Asp Leu Val Phe Thr Asn Trp Leu Met Met Tyr Leu
        115                 120                 125

Ser Asp Asp Glu Val Ile Arg Phe Leu Leu Asn Ala Leu Arg Trp Leu
    130                 135                 140

Arg Pro Asn Gly Tyr Leu His Leu Arg Glu Ser Cys Ser Gln Pro Ser
145                 150                 155                 160

Thr Ala Arg Val Gly Gly Thr Met His Asn Ser Thr Glu Ile Asn Pro
                165                 170                 175

Thr Ser Tyr Arg Leu Ser Ser Glu Tyr Ile Lys Leu Leu Arg Asn Ile
            180                 185                 190

Arg Tyr Arg Glu Leu Asp Gly Thr Leu Phe Arg Phe Glu Val His Trp
        195                 200                 205

Ala Cys Ser Val Pro Thr Tyr Ile Val Val Gln Asn Asn Trp Arg Gln
    210                 215                 220

Val His Trp Leu Thr Gln Lys Val Arg Cys Asn Asp Asp Ala Ile Met
225                 230                 235                 240

Ser Ile Glu His Leu Leu Gly His Phe Ser Thr Leu Trp Lys Val Glu
```

-continued

```
                245                 250                 255
Gln Gln Lys Trp Asp Arg Tyr Leu Asp Asn Glu Ser Tyr Cys Trp Thr
            260                 265                 270

Asp Glu Val Phe Gly Tyr Ala Leu Met Lys Glu Thr Ile Glu Ser Met
        275                 280                 285

Pro Ala Val Leu Ala Tyr Asn Pro Arg Lys Leu Ala Tyr His Leu His
    290                 295                 300

Ile Asn Ala His Arg Ile Ser Glu Met Leu His Cys Asn Val Val Trp
305                 310                 315                 320

Asn Val Glu Ile Asn Glu Phe Phe Tyr Arg Thr Ser Leu Thr Lys Ala
                325                 330                 335

Asn Arg Leu Lys Asp Gln Arg Val Arg Phe Gly Trp Asn Ala Thr Leu
            340                 345                 350

Glu Ser Ser Leu Asn Tyr Trp Lys Glu Arg Gly Ala Leu Phe Asp Ile
        355                 360                 365

Phe Ile Ala Thr Glu Phe Phe Thr Asp Leu Asp Glu Ser Thr Ile Asp
    370                 375                 380

Lys Leu Ser Val Val Leu Lys Ala Asp Ala Pro Leu Ile Leu Leu Glu
385                 390                 395                 400

Pro Phe Asp Glu Ser Ala Tyr Asp Glu Lys Tyr Ile Met Lys Leu Leu
                405                 410                 415

Ser Arg Tyr Gln Gln Ile Ser Ile Glu Asp Ile Thr Glu Met Cys Thr
            420                 425                 430

Glu Ala Ile His Lys Tyr Leu Ser Glu Arg Asp Leu Glu Asn Asn Ile
        435                 440                 445

Gly Thr Lys Val Trp Lys Leu Ile Lys Ala His Met
    450                 455                 460

<210> SEQ ID NO 8
<211> LENGTH: 460
<212> TYPE: PRT
<213> ORGANISM: Haemonchus contortus

<400> SEQUENCE: 8

Met Thr Ala Glu Val Arg Arg Asp Ser Phe Lys Thr Phe Trp Asp Lys
1               5                   10                  15

Tyr Ser Asp Lys Pro Asp Thr Asn Ser Met Met Leu Asn Gln Thr Ala
            20                  25                  30

Gln Asp Leu Glu Ala Ser Asp Arg Ala Asp Ile Leu Ser Ser Leu Pro
        35                  40                  45

His Leu Thr Asn Lys Asp Val Val Asp Ile Gly Ala Gly Ile Gly Arg
    50                  55                  60

Phe Thr Thr Val Leu Ala Glu Thr Ala Arg Trp Val Leu Ser Thr Asp
65                  70                  75                  80

Phe Ile Glu Ser Phe Ile Glu Lys Asn Gln Glu Arg Asn Ala His Met
                85                  90                  95

Gly Asn Ile Ser Tyr Gln Ile Gly Asp Ala Val His Leu Gln Met Asp
            100                 105                 110

Glu Lys Ser Val Asp Leu Val Phe Thr Asn Trp Leu Met Met Tyr Leu
        115                 120                 125

Ser Asp Arg Glu Val Ile Glu Phe Leu Leu Asn Ala Met Arg Trp Leu
    130                 135                 140

Arg Ala Asp Gly Tyr Ile His Leu Arg Glu Ser Cys Ser Glu Pro Ser
145                 150                 155                 160

Thr Gly Arg Leu Lys Thr Ala Thr Met His Ser Ala Val Asp Ala Asn
```

```
                      165                 170                 175
Pro Thr His Tyr Arg Phe Ser Ser Leu Tyr Ile Lys Leu Leu Arg Ala
            180                 185                 190

Ile Arg Tyr Gly Asp Ser Asp Gly Lys Met Trp Lys Phe Asp Val Gln
            195                 200                 205

Trp Ser Cys Ser Val Pro Thr Tyr Ile Arg Arg Cys Asn Asn Trp Arg
            210                 215                 220

Gln Val His Trp Leu Thr Lys Lys Val Pro Ala Val Gly Asp Glu Glu
225                 230                 235                 240

Thr Ser Val Asp Asp Leu Leu Asn Leu Phe Ser Gln Ile Trp Pro Ala
                245                 250                 255

Glu Gln Lys Thr Trp Asp Glu Lys Leu Asp Asn Glu Lys Tyr Ser Trp
            260                 265                 270

Thr Asp Lys Ile Phe Ser Asn Ala Ile Asp Asp Glu Val Val Pro Lys
            275                 280                 285

Asn Ser Thr Ala Tyr Val Phe Thr Pro Arg Gln Arg Ser Pro Phe Leu
            290                 295                 300

His Val Asn Ser His Leu Leu Ala Glu Lys Phe Thr Cys Asn Val Trp
305                 310                 315                 320

Asn Val Glu Thr Lys Glu Tyr Leu Tyr Arg Thr Ser Leu Thr Lys Ala
                325                 330                 335

Asn Asn Gln Lys Asp Gln Arg Val Arg Phe Gly Trp Asn Glu Ser Leu
            340                 345                 350

Ser Ser Pro Ile Asp Tyr Trp Asn Gln Arg Asp Ala Ser Phe Asp Cys
            355                 360                 365

Met Val Ala Thr Glu Leu Leu Ala Thr Cys Asp Asp Glu Ser Val Lys
            370                 375                 380

Ser Ile Ala Ser Ile Met Lys Pro Glu Ala Lys Val Val Leu Leu Glu
385                 390                 395                 400

Pro Val Ser Gly Ile Asp Glu Thr Ser Val Arg Gln Arg Met Thr Thr
                405                 410                 415

Cys Gly Phe Lys Asn Ile Thr Ile Val Asp Val Thr Gln Glu Ser Leu
            420                 425                 430

Asn Ala Glu Val Ser Phe Ile Lys Asp His Asn Leu Asp Val Glu Leu
            435                 440                 445

Ser Gly Cys Asn Tyr Leu Leu Ile Lys Ala Ser Leu
            450                 455                 460

<210> SEQ ID NO 9
<211> LENGTH: 457
<212> TYPE: PRT
<213> ORGANISM: Meloidogyne incognita

<400> SEQUENCE: 9

Met Arg Met Arg Leu Glu His Glu Asp Thr Asp Met Asp Trp Arg Gln
1               5                   10                  15

Ile Tyr His Ser Phe Trp Asn Lys Phe Ser Asp Arg Ala Asp Asn Thr
            20                  25                  30

Ser Met Leu Leu Asn Ala Asp Ala Asp Lys Phe Glu Ala Leu Asp Arg
        35                  40                  45

Ala Glu Ile Ile Gly Met Leu Pro Ser Phe Lys Asn Lys Phe Val Val
    50                  55                  60

Asp Ile Gly Ala Gly Ile Gly Arg Phe Thr Thr Glu Phe Ala Lys Lys
65                  70                  75                  80

Ala Arg Glu Val Val Ser Thr Asp Phe Val Ala Ser Phe Ile Glu Lys
```

```
            85                  90                  95
Asn Arg Glu Thr Asn Ile Ala Phe Asn Ile Glu Trp Arg Val Gly
            100                 105                 110

Asp Ala Val Arg Leu Asp Phe Glu Glu Gly Ser Ile Asp Ile Val Phe
            115                 120                 125

Thr Asn Trp Leu Leu Met Tyr Leu Val Asp Glu Val Val Gln Phe
            130                 135                 140

Leu Ile Asn Ala Ile Lys Trp Leu Arg Pro Gly Gly Tyr Leu His Leu
145                 150                 155                 160

Arg Glu Ser Cys Ser Glu Pro Ser Ser Lys Lys Ser Asn Asn Ser Leu
                    165                 170                 175

His Ser Asn Ser Asp Ser Ile Asn Pro Thr Lys Tyr Arg Phe Ser Ser
                180                 185                 190

Ala Tyr Ile Gln Leu Leu Lys Ser Ile Asn Phe Lys Ser Gly Asp Gly
                195                 200                 205

Thr Val Trp Gly Phe Lys Ile His Trp Ala Ser Ser Val Asn Val Tyr
            210                 215                 220

Ile Gln Lys Asn Ala Asn Trp Arg Gln Val His Trp Leu Val Ser Lys
225                 230                 235                 240

Val Pro Lys Lys Glu Lys Phe Met Pro Asn Leu Gly Thr Leu Leu Gly
                245                 250                 255

Glu Lys Trp Pro Glu Glu Gln Lys Glu Trp Asp Asn Lys Leu Asp Leu
                260                 265                 270

Ala Leu Asn Glu Asn Gln Asn Ile Thr Ser Thr Leu Ala Ser Tyr Leu
                275                 280                 285

Leu Ser Ser Gly Ile Gly Thr Asn Ser Val Ile Leu Val Phe Asp Leu
            290                 295                 300

Arg Asn Ser Glu Asn Gln Pro Ser Ile Asn Val His Thr Leu Ala Asn
305                 310                 315                 320

Arg Leu Asn Ser Asn Ile Trp Ser Val Ser Leu Asn Pro Phe Cys Phe
                325                 330                 335

Arg His Ser Leu Thr Leu Ala Asn Asn Asn Gln Asp Arg Arg Ile Arg
                340                 345                 350

His Ser Trp His Glu Asp Ile Glu Ser Ala Phe His Phe Leu Gly Glu
            355                 360                 365

Gln Ile Ser Gly Lys Glu Lys Asn Ile Ser Arg Leu Phe Asp Val Ile
            370                 375                 380

Ile Gly Ile Gly Leu Leu Glu Lys Ile Lys Lys Met Lys Asp Ala Ser
385                 390                 395                 400

Glu Lys Val Glu Lys Ile Leu Gly Arg Tyr Leu Leu Ser Ile Glu Thr
                405                 410                 415

Gly Glu Gly Asp Asp Ile Arg Lys Glu Lys Lys Asn Glu Asp Ile Val
                420                 425                 430

Glu Tyr Phe Pro Ser Glu Leu Phe Thr Lys Gln Thr Ile Glu Phe Lys
                435                 440                 445

Ala Asp Asn Gly Phe Asn Gln Leu Asp
    450                 455

<210> SEQ ID NO 10
<211> LENGTH: 469
<212> TYPE: PRT
<213> ORGANISM: Strongyloides stercoralis

<400> SEQUENCE: 10

Met Glu Gly Glu Asn Asp Arg Gln Asn Phe Leu Glu Tyr Trp Arg Gln
```

-continued

```
  1               5              10              15
Phe Gly Asn Ile Ala Asn Ile Asn Gly Met Met Leu Asn Ala Asn Ala
                 20              25              30

Ser Leu Ile Glu Lys Asn Asp Arg His Asp Val Cys Leu Leu Leu Pro
         35              40              45

Asp Leu Lys Gly Lys Thr Val Leu Asp Ala Gly Ala Gly Ile Gly Arg
 50              55              60

Phe Thr Ala Glu Leu Ala Glu Arg Ala Glu Lys Val Tyr Ala Ser Asp
 65              70              75              80

Phe Ile Ser Glu Tyr Val Thr Lys Leu Gln Glu Leu Ser Ala Glu Ala
                 85              90              95

Leu Lys Asn Gly Lys Ile Ile Asp Val Thr Val Ala Asp Ala Thr Cys
                100             105             110

Leu Ser Tyr Pro Glu Asn Ser Tyr Phe Leu Val Phe Thr Asn Trp Leu
                115             120             125

Phe Met Tyr Phe Asn Asn Thr Glu Cys Val Arg Phe Thr Val Asn Ala
                130             135             140

Leu Lys Trp Leu Glu Glu Gly Gly Tyr Phe Lys Leu Arg Glu Ser Cys
145             150             155             160

Ser Glu Pro Ser Thr Arg Arg Val Gly Asn Arg Asn Glu Thr Ser Leu
                165             170             175

His Ala Ala Val Gln Ser Asn Pro Thr Glu Tyr Arg Phe Ser Ser Val
                180             185             190

Tyr Leu Lys Leu Ile Glu Ala Arg Tyr Val Asp Ser Asn Asn Gln
                195             200             205

Lys Trp Lys Phe Glu Ile Glu Ile Cys Gly Ser Ile Pro Thr Tyr Ile
                210             215             220

Leu Asn Gly Asn Thr Trp Arg Gln Val Gln Leu Ile Ala Lys Lys Val
225             230             235             240

Lys Ala Asp Asp Asn Asp Val Val Leu Ser Gln Asp Glu Leu Lys Asn
                245             250             255

Leu Met Thr Asn Asp Trp Ile Met Glu Gln Lys Lys Thr Asp Ser Ile
                260             265             270

Val Asp Gly Arg Val Gln Tyr Phe Ala Asp Lys Ile Phe Ala Asn Glu
                275             280             285

Leu Ser Asn Ile Asp Met Thr Asn Thr Glu Ser Ile Ser Ser Ile Phe
                290             295             300

Val Phe Gln Ser Ser Phe Asn Pro Trp Tyr Lys Arg Ile Phe Pro Phe
305             310             315             320

Ser Leu Ala Ser Asn Lys Tyr Cys His Val Trp Thr Asn Glu Gly Asn
                325             330             335

Arg Glu Leu Phe Arg Cys Ser Leu Thr Ser Ala Asn Glu Glu Arg Asn
                340             345             350

Ile Gly Met Phe Phe Thr Tyr Ser Lys Asp Asn Val Phe Asn Ala Leu
                355             360             365

Asp Tyr Val Lys Lys Arg Asn Phe Leu Leu Asn Ser Phe Leu Ala Ile
                370             375             380

Asp Tyr Leu Asn Asn His Glu Val Asn Phe Ile Glu Ser Phe Asn Asn
385             390             395             400

Ile Ala Ser Gln Asp Ala Lys Ile Leu Leu Leu Glu Ser Phe Ser Asn
                405             410             415

Glu Asp Glu Lys Asn Leu Lys Leu Ser Lys Leu Asn Lys Gln Tyr Thr
                420             425             430
```

Val Lys Cys Val Thr Glu Asn Val His Asn Glu Val Lys Asn Val His
    435                 440                 445

Gln Asp Glu Glu Ile Val Cys Asp Val Thr Ser Lys Lys Trp Met Leu
450                 455                 460

Ile Asn Val Asn His
465

<210> SEQ ID NO 11
<211> LENGTH: 437
<212> TYPE: PRT
<213> ORGANISM: Ascaris suum

<400> SEQUENCE: 11

Met Pro Ala Ala Glu Arg Glu Leu Ile Ser Ala Leu Phe Asp Val Thr
1               5                   10                  15

Pro Lys Asp Ala Leu Thr Ser Val Leu Leu Val Thr Ser Ala Gln Ser
            20                  25                  30

Glu Glu Ser Asn Ser Ser Leu Val Ala Leu Phe Glu Asp Arg Ala Ile
        35                  40                  45

Asn Val Thr Ile Val Glu Arg Leu Gly Leu Gln Ser Thr Arg Ala
50                  55                  60

Asp Ala Tyr Asp Ala Ile Ile Ser Asn Lys Leu Ile Val Glu Asn Cys
65                  70                  75                  80

Leu Ile Asn Lys Pro Ser Asp Leu Asp Thr Phe Val Ala Ser Ala Leu
                85                  90                  95

Lys Glu Glu Gly Val Leu Ile Val Arg Glu Asp Leu Asn Gly Cys Ser
            100                 105                 110

Ala Cys Glu Lys Val Ala Gln Leu Thr His Phe Phe Asp Leu Phe Arg
        115                 120                 125

Thr Thr Leu Asn Gly Val Thr Ile Gly Phe Lys Phe Tyr Ser Leu Lys
130                 135                 140

Gln Val Asn Ala Ser Ile His Thr Glu Gly Asn Phe Leu Asp Val Phe
145                 150                 155                 160

Trp Ile Leu Arg Lys Glu Cys Phe Glu Ala Leu Asp Glu Asn Gln Lys
                165                 170                 175

Thr Lys Thr Phe Arg Asp Phe Leu Asp Thr Thr Gln Tyr Thr Asp Glu
            180                 185                 190

Ser Ile Arg Ala Tyr Glu Trp Ile Phe Gly Asp Asn Phe Ile Ser Pro
        195                 200                 205

Gly Gly Tyr Asp Glu Asn Leu Glu Val Leu Lys Arg Phe Gly Asp Leu
210                 215                 220

Lys Pro Asp Cys Lys Met Leu Asp Ile Gly Val Gly Ile Gly Gly
225                 230                 235                 240

Ala Arg Gln Ala Ala Arg Glu Phe Gly Ala Leu Val Leu Gly Met Asp
                245                 250                 255

Ile Ser Ala Asn Met Leu Ser Ile Ala Met Asp Arg Leu Gln Asn Glu
            260                 265                 270

Lys Asp Thr Arg Val Arg Tyr Gln Ile Ser Asp Ala Leu Glu Tyr Glu
        275                 280                 285

Phe Pro Ala Asn Ser Phe Asp Tyr Val Phe Ser Arg Asp Gly Leu His
290                 295                 300

His Asn Glu Arg Ile Asp Ile Val Met Arg Lys Ile Phe His Trp Leu
305                 310                 315                 320

Lys Pro Gly Gly Lys Val Leu Ile Thr Val Tyr Gly Met Gly His Gly
                325                 330                 335

```
Thr Leu Ser Ala Lys Phe Gln Ala Tyr Val Glu Lys Arg Lys Tyr Phe
                340                 345                 350

Leu Lys Thr Leu Glu Glu Met Val Glu Ile Thr Glu Ala Ala Gly Phe
            355                 360                 365

Glu Asn Val Gln Gly Thr Asn Leu Thr Lys Arg Phe Arg Asp Ile Leu
        370                 375                 380

Leu Asp Glu Arg Thr Lys Thr Leu Asn Arg Lys Asn Glu Phe Leu Glu
385                 390                 395                 400

Lys Phe Asp Glu Gly Thr Phe Asn Ser Leu Leu Asn Gly Trp Asn Asp
                405                 410                 415

Lys Ile Gly Phe Ile Asp Asp Asn His Asn Trp Asn Gln Ile Phe
            420                 425                 430

Ala Thr Lys Pro Leu
        435

<210> SEQ ID NO 12
<211> LENGTH: 472
<212> TYPE: PRT
<213> ORGANISM: Meloidogyne javanica

<400> SEQUENCE: 12

Met Ser Ala Leu Ser Cys Glu Leu Ala Tyr Ala Leu Gln Asn His Pro
1               5                   10                  15

Asn Ala Pro Lys Asn Gly Glu Thr Val Leu Leu Ile Asn Asp Gln
            20                  25                  30

Asp Val Asn Glu Arg Asn Leu Asn Ser Asp Leu Arg Asn Leu Phe Glu
        35                  40                  45

Asp Lys Phe Asn Leu Glu Glu Met Asp Ile Gly Glu Leu Ile Asn Ile
50                  55                  60

Ser Glu Arg Leu Asp Lys Glu Asp Asn Asp Asn Glu Glu Asn Leu
65                  70                  75                  80

Glu Thr Arg Phe Asp Ala Ala Ile Cys Ser Asn Leu Phe Ile Gly Gln
                85                  90                  95

Gly Ile Val Asn Asp Arg His Arg Ile Ala Gln Val Leu Gly Leu Leu
            100                 105                 110

Leu Arg Leu Ile Arg Thr Asp Gly Val Val Ile Arg Glu Asn Leu
        115                 120                 125

Lys Gln Trp Gly Ser Arg Ser Ile Ala Asp Leu Thr Lys Phe Leu Asp
        130                 135                 140

Val Phe Ala Phe Arg Lys Gln Gln Asn Gln Lys Gln Gln Gln Thr
145                 150                 155                 160

Leu Gly Phe Asn Phe Tyr Gly Met Ser Gln Val Gln Asp Ser Ile Tyr
                165                 170                 175

Ala His Ser Asn Phe Leu Asp Val Phe Trp Ser Leu Thr Thr Ala Ile
            180                 185                 190

Glu Val Arg Leu Tyr Asp Asp Lys Leu Ala Thr Phe Glu Phe Leu
        195                 200                 205

Asp Lys Thr Gln Tyr Thr Glu Asp Asn Val Ala Ser Tyr Glu Trp Ile
        210                 215                 220

Phe Gly Thr Asp Phe Ile Ser Pro Gly Gly Val Asn Glu Asn Arg Arg
225                 230                 235                 240

Val Leu Lys Tyr Phe Arg His Leu Arg Pro Gly Gln Gln Met Leu Asp
                245                 250                 255

Ile Gly Val Gly Ile Gly Gly Ala Arg Gln Ala Ala Arg Glu Phe
            260                 265                 270
```

```
Gly Leu Gln Val Leu Gly Cys Asp Leu Ser Ser Asn Met Ile Gln His
        275                 280                 285
Ala Phe Asp Arg Asn Gln Arg Asp Lys Asp His Arg Val Glu Tyr Gln
    290                 295                 300
Ile Ala Asp Ala Met Val Tyr Arg Tyr Glu Ser Asn Ala Phe Asp Ile
305                 310                 315                 320
Val Phe Ser Arg Asp Cys Ile Gln His Ile Lys Asp Thr Lys Arg Leu
                325                 330                 335
Phe Arg Asn Ile Tyr Thr Trp Leu Lys Pro Gly Gln Val Leu Val
            340                 345                 350
Thr Met Tyr Gly Lys Gly His Gly Val Leu Ser Pro Lys Phe His Glu
        355                 360                 365
Tyr Val Arg Lys Arg Gln Tyr Ala Leu Lys Thr Leu Glu Glu Tyr Arg
    370                 375                 380
Glu Ile Ala His Asn Val Gly Leu Thr Thr Ile Tyr Thr Glu Asn Met
385                 390                 395                 400
Thr Lys Arg Leu Arg Glu Ile Leu Val Ile Glu Arg Asp Arg Ala Val
                405                 410                 415
Glu Asn Lys Glu Glu Phe Ile Gln Lys Phe Ser Glu Lys Leu Tyr Ser
            420                 425                 430
Lys Leu Ile Glu Gly Trp Ala Asp Lys Leu Gln Phe Ile Asp Glu Asp
        435                 440                 445
Asn Gln Asn Trp Leu Leu Leu Arg Ala Glu Lys Pro Val His Pro His
    450                 455                 460
Ala Tyr Leu Thr Glu Ala Gly Ala
465                 470

<210> SEQ ID NO 13
<211> LENGTH: 1380
<212> TYPE: DNA
<213> ORGANISM: Ascaris suum

<400> SEQUENCE: 13
atgaccgaag caattcgacg ctcttctttc aaaaatttct ggtcgaaatt ttcgcatcgt      60
tgtgataata cagtaatgat gttgaataaa agcgccgatg aatttgaagc cgatgatcgt     120
gcagatatta tatcttcatt acccgatcta catggcaagg atattgtcga tattggcgct     180
ggaattggac gtttcacgac aattttcgca catgatgcac gtcatgtact atcatgcgat     240
tttatcgaaa gtttcatggc aaaaaataaa gaacggaatg cgcatttctc taatatctct     300
tatcaggttg gcgatgcggt acatttacaa ctcgatccaa acagtgtaga ccttgtgttc     360
acgaactggc tcatgatgta cctcagcgat gatgaagtta ttcgctttct tctcaacgca     420
ctccgatggc ttcgtcctaa cggctatttg caccttcgag agtcatgcag ccaaccgtca     480
accgcacgag ttggaggaac gatgcataat agtacagaga taaatccaac cagctatcga     540
ctatcctctg agtatataaa attgctaagg aatattcgtt atcgtgaatt agatggcaca     600
ttatttcgct tcgaagtgca ttgggcttgt tcagtgccca cttatatcgt cgtgcaaaat     660
aattggcgtc aagttcattg gttaacgcaa aaagttcgat gcaacgatga tcgataatg     720
tctatcgaac accttctcgg acattttagt acactatgga aggtggagca acaaaagtgg     780
gatcgttacc tcgacaatga atcctattgc tggactgatg aggtgtttgg ctatgcgtta     840
atgaaggaaa cgattgagag tatgcccgca gtattggcat ataatcctcg caaattggcc     900
tatcatttgc atataaatgc gcatcgcatt tctgagatgt acattgtaa tgttgtatgg     960
aatgtggaga taaatgaatt tttctatcgg acatcattaa cgaaagcaaa tcgcctcaaa    1020
```

```
gatcaacgag ttcgatttgg atggaatgct acgcttgaat cgtcgctgaa ttattggaaa   1080
gaacgtggtg ctctcttcga tatttttatc gccactgaat ttttcaccga tctcgatgaa   1140
agtaccatcg ataagctctc cgtggtatta aaagcggatg cacctctaat tctgctggag   1200
ccatttgacg aatcagctta tgatgagaaa tacatcatga agttgttatc acgttatcaa   1260
caaatttcta tcgaggatat cactgagatg tgcacagaag cgattcataa atatctaagc   1320
gaaagagatt tagagaataa tattggaaca aaagtatgga attaataaa agcgcatatg   1380
```

<210> SEQ ID NO 14
<211> LENGTH: 1380
<212> TYPE: DNA
<213> ORGANISM: Haemonchus contortus

<400> SEQUENCE: 14

```
atgacggctg aggtgcgacg ggattccttc aagacgttct gggacaagta ctcagataaa     60
cccgacacta attcgatgat gctcaaccag actgcacaag atctggaagc tagcgataga    120
gcagatatcc tctccagcct acctcaccta accaacaaag acgtggtcga tattggcgct    180
ggaatcgggc gcttcactac tgtgctagca gaaactgctc gatgggttct ttcaacggat    240
ttcatcgaat cgttcatcga aaaaaatcaa gaacgaaatg ctcacatggg taacatcagt    300
tatcaaatag gagacgcagt ccatttgcaa atggacgaga aaagcgtgga tctcgttttt    360
acgaattggt tgatgatgta tctctccgat cgtgaagtca ttgaatttct gctgaatgct    420
atgcgatggt tgagagcgga cggatacatt catctcagag aaagctgctc cgagccaagc    480
acgggccgtc tgaagaccgc cacaatgcac tcagccgttg acgccaaccc aacacattac    540
cgtttctcat cgctgtatat caagcttctt cgagcaatcc gatacgggga cagtgatgga    600
aaaatgtgga atttgatgt gcagtggagc tgctcggtgc ccacctacat acggaggtgc    660
aataactggc gtcaagtgca ttggttgacg aagaaggtac cggcagttgg cgacgaagag    720
acttcagtcg acgatttgct caacttgttc agccagatct ggccagccga acaaaagacg    780
tgggatgaaa aactagacaa tgaaaaatac agttggactg ataagatatt ctcgaatgcg    840
atcgatgatg aagtggtgcc aaagaacagt accgcctatg tcttcacacc aaggcaacga    900
tcccccttct tgcacgtcaa ctcgcacctt ttggcagaga agttcacatg caatgtatgg    960
aatgttgaaa caaagagta tttgtatcgt acttcgttga cgaaggcaaa caaccagaag   1020
gaccaacgag tgcgcttcgg ttggaacgag tccttgtctt cgcccatcga ctactggaat   1080
cagagggacg cttcatttga ctgcatggta gcaactgaac ttctcgcgac ttgtgatgat   1140
gagagcgtaa agagtattgc gagcattatg aaaccagaag cgaaggtggt gctcctcgaa   1200
ccagttagcg gaattgacga acgtccgtt aggcagcgaa tgactacttg tgggttcaaa   1260
aacattacca tcgtcgatgt tacacaggag tccttgaacg ccgaggtttc tttcattaag   1320
gaccacaact tggacgtcga actctctggt tgtaattacc tactgatcaa ggcttcactt   1380
```

<210> SEQ ID NO 15
<211> LENGTH: 1371
<212> TYPE: DNA
<213> ORGANISM: Meloidogyne incognita

<400> SEQUENCE: 15

```
atgcggatgc gactggagca cgaggacact gacatggact ggaggcaaat ttatcactcc     60
ttttggaaca aattttccga tagggctgac aatacatcca tgcttttaaa tgcggatgct    120
gataaatttg aagctcttga cagagccgaa attatcggaa tgttgccctc ttttaaaaat    180
```

```
aaatttgttg tggatattgg ggcgggtatt ggaagattca caacagaatt tgccaaaaag      240
gcaagagaag tggtctcaac agattttgta gctagcttta tcgagaaaaa tcgggaaaca      300
aatatagcct ttaataacat tgaatggaga gttggtgatg ctgtaagatt agattttgaa      360 gagggagta ttgatatagt ctttaccaat tggcttttga tgtatttagt ggatgaagaa       420
gttgttcaat ttttgattaa tgccattaaa tggctcaggc ctggcggtta tttacatttg      480
agagagtcct gctctgaacc tagcagcaaa aaatctaata attcgctaca ttccaattcg      540
gatagtatca atccaactaa atatcgcttt tcatccgcat atattcaatt gctcaaatca      600
attaatttta aaagcggaga tggaaccgtt tgggggttta aaatccactg gctagctct       660 gttaatgttt atattcaaaa aaatgcaaat tggagacaag tgcattggtt agtaagcaag      720
gttcctaaaa aggaaaaatt tatgccaaat ttgggtacac tgcttggaga gaagtggcct     780
gaagagcaga aggaatggga caataaactt gacttggctt tgaatgagaa tcagaatatc     840
acctcaactc tagccagtta tcttttatct agtgggattg gaacaaattc agttatactt      900
gttttcgact tgagaaatag tgaaaatcag cccagtatta tgttcacac attggctaac      960 agattaaatt caaatatttg gtctgtttcc ctcaatcctt tctgcttccg tcattcatta     1020
acccttgcta ataataacca agatcgacgg attagacact cttggcatga ggatattgaa    1080
agcgctttcc acttttggg tgaacaaata tccggcaaag agaaaaatat cagcagatta    1140
tttgatgtga ttattggtat tggtttgtta gaaaaaatta aaaaaatgaa ggacgctagc    1200
gagaaagttg agaaaatcct tggccgttat ttgttaagta ttgaaacagg cgaaggagat   1260
gatatacgaa aggaaaaaaa gaatgaggac attgtagaat atttcccatc agaactattt    1320
acaaaacaaa caatagaatt caaagcagat aatggattta atcagcttga t             1371
```

<210> SEQ ID NO 16
<211> LENGTH: 1407
<212> TYPE: DNA
<213> ORGANISM: Strongyloides stercoralis

<400> SEQUENCE: 16

```
atggagggtg aaaatgatag acagaatttt cttgaatatt ggagacaatt tggcaatata      60
gctaatatca atggtatgat gcttaatgct aatgcttctt taattgagaa aaatgatagg     120
catgatgtat gtctattact tcctgattta aaaggaaaaa ctgttttaga tgctggtgct    180
ggaattggac gttttactgc tgaacttgct gaaagggctg aaaagtttta tgcatcagat    240
tttatttctg aatatgttac taaattacaa gaacttagtg ctgaagcgtt aaaaaatgga    300
aaaattattg atgttacagt agcagatgct acatgtcttt cttatccaga gaatagttat    360
ttccttgttt ttactaattg gttgtttatg tattttaata atactgaatg tgtacgtttt     420
actgtaaatg cattaaaatg gttagaagaa ggtggatatt ttaaattaag agaatcatgt   480
tctgaaccat caacaagaag agttggaaat agaaatgaaa cttctcttca tgctgccgtt    540
caatcaaatc caactgaata tagattttca tctgttttatc ttaaattaat tgaagcagct    600
agatacgttg attcaaataa tcaaaaatgg aaattcgaaa tagaaatttg tggttctatt    660
ccaacataca ttttaaatgg taatacttgg agacaagtac agttaattgc taaaaaagta    720
aaagcagatg ataatgatgt tgtttttatcc caagatgagt tgaaaatttt aatgactaat    780
gattggataa tggaacaaaa aaagactgat tctattgttg atggtagagt acaatatttt    840
gctgataaaa ttttttgctaa tgaattatca aatattgata tgactaatac tgaatccatt    900
tcatcaatat ttgttttcca atcttcattt aatccatggt acaaaagaat tttcccattt     960
```

```
tctttagcat caaataaata ttgccatgtc tggacaaatg agggtaatcg tgaactttt       1020 agatgttcat taacttcagc taatgaagaa agaaatattg gaatgttttt tacctattca      1080
aaagacaatg tttttaatgc cttagattac gttaaaaaaa gaaacttttt attaaacagt      1140
tttctagcta ttgactattt aaataatcat gaagttaatt ttattgaatc atttaataat     1200
attgcttctc aagatgctaa aattctcctt cttgaatcat tttcaaatga ggatgaaaaa     1260
aatttaaaat taagtaaact aataagcaa tacacagtaa agtgcgtaac agaaaacgtt      1320
cataatgaag ttaaaaatgt acatcaagat gaagaaattg tatgtgacgt tacatcgaaa     1380
aaatggatgc ttatcaatgt aaaccat                                         1407
```

<210> SEQ ID NO 17
<211> LENGTH: 1311
<212> TYPE: DNA
<213> ORGANISM: Ascaris suum

<400> SEQUENCE: 17

```
atgcctgcgg cagagcgtga actaatcagt gcattattcg acgttacacc gaaagatgct      60
cttacaagtg tactcttggt cacctctgcc caatcagagg aaagcaattc atcactggtt      120
gcactctttg aggacagagc aattaacgta accatcgttg agcgtcttga gggattgcaa      180
agcactcgag ctgacgcata tgacgccatt atcagcaata aattgatcgt cgagaactgt      240
ttaatcaata aaccatcaga tctcgataca ttcgtcgcat cggctctaaa agaagaaggt      300
gtactcatcg ttcgtgaaga cctaaatggt tgttctgcgt gtgagaaggt cgctcagcta      360
acgcatttct ttgatctgtt tcgaacaact ctgaacggcg ttacgattgg cttcaaattc      420
tattcactca gcaagtcaa tgcctcaatt cataccgaag gaaactttct ggatgtcttc      480
tggatattgc ggaaagaatg tttcgaagcg ctggacgaga accaaaaaac aaaaaccttt     540
cgtgattttc tcgatactac gcaatacact gacgagagca tacgtgcata tgaatggatc     600
ttcggcgata acttcatcag tccgggcggt tatgacgaaa acttagaagt tctgaagcga      660
ttcggtgatc taaaaccgga ttgtaaaatg ctcgacatcg tgttgggat cggtggaggt      720 gcccgccagg ctgctaggga attcggagcg ctggttctcg gtatggatat tagtgcgaat      780 atgcttttcaa tagcgatgga tcgcctacag aatgagaaag acactcgcgt tcgttatcaa    840
atatccgacg ctctcgaata tgagtttcca gccaactcgt tgattacgt tttcagtcgt      900 gacggttac atcataacga gcgcatcgac atcgtaatgc gaaagatttt ccactgttg       960 aaacctggtg ggaaagtgct catcacggtg tatggcatgg ccatgggac attaagcgcg     1020 aaattccaag cctatgtgga aaagaggaaa tattttctga agacactcga agagatggtt     1080
gagataactg aagctgctgg attcgaaat gtgcaaggga caacctcac caagcgattc       1140 cgcgatatac tgctcgacga gcggacaaaa acgctgaacc gaaaaaacga attccttgag     1200
aaattcgatg aaggaacatt caacagcctc ttgaacggat ggaatgataa gatcggcttt     1260
atcgacgacg ataaccataa ttggaatcag atcttcgcaa caaaaccact t               1311
```

<210> SEQ ID NO 18
<211> LENGTH: 1416
<212> TYPE: DNA
<213> ORGANISM: Meloidogyne javanica

<400> SEQUENCE: 18

```
atgagtgcat tatcttgtga attagcttat gcacttcaaa atcatccaaa tgcacccaaa      60
aatggcgaaa ctgttctctt attaattaac gatcaagatg ttaatgaaag gaatttaaat      120
```

```
tctgatctaa gaaatttatt cgaagataaa tttaatttgg aggagatgga tattggagag      180
ttgataaata tatcagaacg tttagataaa gaagataatg acaacgaaga agagaattta      240
gaaacacgtt ttgatgctgc tatttgctct aatttattta ttggacaagg aattgtaaat      300
gaccgtcatc gtattgctca agtattagga ttacttcttc gtttaatacg gacagatgga      360
gttgtaatta ttagagaaaa tctaaagcaa tggggttctc gttcaattgc tgatttaact      420
aaatttcttg atgtttttgc ttttcgaaaa caacaaaata atcaaaaaca acaacaaaca      480
cttggattta attttatgg aatgagccaa gtacaggaca gcatttatgc acattctaat      540
tttcttgacg ttttttggag cttaacaaca gctattgaag ttagattata tgatgataaa      600
ttagctactt ttagggaatt tttgataaaa acacagtata ctgaggacaa cgttgctagt      660
tatgagtgga tatttgggac agattttatc agcccaggtg gagtgaatga aatagaaga       720 gtactaaaat atttccgtca tttacgtcca ggacaacaaa tgcttgatat tggtgttgga      780
attggtggag gagctagaca agctgctagg gagtttggtc ttcaagtact tggttgtgat      840
ctttcttcaa atatgattca acatgctttt gatcgtaatc aacgtgacaa agatcatcgt      900
gttgaatatc aaattgctga tgctatggtt tatcgttatg aatctaatgc ttttgatatt      960
gtatttagta gagattgtat tcaacatatt aaagatacaa aaagattatt tagaaatatt     1020
tatacttggc ttaaaccagg tggacaagta cttgttacaa tgtatgggaa aggacatgga     1080
gttctctcgc caaaatttca tgaatatgtt cgtaaacggc aatatgcact aaaaacttta     1140
gaagaatata gagaaattgc tcataatgtt ggtttaacaa ctatttacac agaaaatatg     1200
actaaacgtt tgagagaaat tttagtaatt gaacgtgata gagcagttga aaataaagaa     1260
gaatttattc aaaaatttag tgaaaaactt tattcaaaat taattgaggg ttgggcagat     1320
aaattacaat ttattgatga agataaccaa aattggttgt tacttcgtgc ggagaaaccg     1380
gtgcatccgc atgcttattt aactgaagct ggagct                              1416
```

<210> SEQ ID NO 19
<211> LENGTH: 475
<212> TYPE: PRT
<213> ORGANISM: Caenorhabditis elegans

<400> SEQUENCE: 19

```
Met Ser Thr Asp Gln Gln Ser Ser Val Glu Asp Gln Thr Val Ala Met
 1               5                  10                  15

Val Asn Val Arg Arg Ala Asn Phe Lys Ser Phe Trp Asp Lys Tyr Ser
                20                  25                  30

Asp Lys Pro Asp Thr Asn Ser Met Met Leu Asn His Ser Ala Glu Glu
            35                  40                  45

Leu Glu Ser Ser Asp Arg Ala Asp Ile Leu Ala Ser Leu Pro Leu Leu
        50                  55                  60

His Asn Lys Asp Val Val Asp Ile Gly Ala Gly Ile Gly Arg Phe Thr
    65                  70                  75                  80

Thr Val Leu Ala Glu Thr Ala Arg Trp Val Leu Ser Thr Asp Phe Ile
                85                  90                  95

Asp Ser Phe Ile Lys Lys Asn Gln Glu Arg Asn Ala His Leu Gly Asn
            100                 105                 110

Ile Asn Tyr Gln Val Gly Asp Ala Val Gly Leu Lys Met Glu Ser Asn
        115                 120                 125

Ser Val Asp Leu Val Phe Thr Asn Trp Leu Met Met Tyr Leu Ser Asp
    130                 135                 140
```

Glu Glu Thr Val Glu Phe Ile Phe Asn Cys Met Arg Trp Leu Arg Ser
145                 150                 155                 160

His Gly Ile Val His Leu Arg Glu Ser Cys Ser Glu Pro Ser Thr Gly
                165                 170                 175

Arg Ser Lys Ala Lys Ser Met His Asp Thr Ala Asn Ala Asn Pro Thr
            180                 185                 190

His Tyr Arg Phe Ser Ser Leu Tyr Ile Asn Leu Leu Arg Ala Ile Arg
        195                 200                 205

Tyr Arg Asp Val Asp Asn Lys Leu Trp Arg Phe Asn Val Gln Trp Ser
    210                 215                 220

Cys Ser Val Pro Thr Tyr Ile Lys Arg Ser Asn Asn Trp Arg Gln Val
225                 230                 235                 240

His Trp Leu Ala Glu Lys Val Pro Ala Glu Asp Gly Ala Lys Gly Thr
                245                 250                 255

Ser Phe Asn Glu Leu Val Glu Leu Ile Lys Asn Thr Trp Gln Asn Glu
            260                 265                 270

Gln Glu Ala Trp Asp Ala Lys Leu Asp Asp Glu Lys Tyr Val Trp Thr
        275                 280                 285

Asp Lys Val Phe Ser Ser Ala Leu Thr Ser Leu Pro Ser Asn Ser Thr
    290                 295                 300

Phe Phe Leu Tyr Thr Pro Arg Thr Val Ser Pro Tyr Cys His Ile Asn
305                 310                 315                 320

Ala His Thr Leu Ala Glu Thr Phe Asn Ala Asn Val Trp Asn Thr Glu
                325                 330                 335

Ile Ile Pro Glu Tyr Tyr Arg Thr Ser Leu Thr Lys Ser Asn Asn Leu
            340                 345                 350

Lys Asp Gln Arg Val Arg Phe Gly Trp Asn Gln Ser Leu Thr Asp Ser
        355                 360                 365

Val Thr Tyr Trp Gln Gln Lys Asp Ala Leu Phe Asp Val Phe Val Ala
    370                 375                 380

Thr Glu Phe Leu Ser Thr Val Asp Asp Glu Thr Ile Arg Gln Leu Pro
385                 390                 395                 400

Asn Val Met Ser Asp Gly Ala Lys Phe Ile Thr Leu Glu Pro Val Asp
                405                 410                 415

Glu Val Asn Glu Ala Glu Met Lys Gln Arg Ile Gln Glu Leu Gly Tyr
            420                 425                 430

Thr Leu Lys Ser Phe Thr Asp Val Thr Asp Gln Cys Ile Glu Ala Gln
        435                 440                 445

Glu Gln Tyr Phe Lys Asp His Glu Gln Leu Arg Asp Glu Lys Val Ile
    450                 455                 460

Arg Lys Asn Trp Val Leu Leu Glu Leu Thr His
465                 470                 475

<210> SEQ ID NO 20
<211> LENGTH: 484
<212> TYPE: PRT
<213> ORGANISM: Caenorhabditis elegans

<400> SEQUENCE: 20

Met Asp Arg Tyr Ser Pro Tyr Asp Lys Thr Val Phe Leu Ile Phe Cys
1               5                   10                  15

Thr Ala Tyr Ile Leu Gln Lys Ala Met Val Asn Val Arg Arg Ala Asn
            20                  25                  30

Phe Lys Ser Phe Trp Asp Lys Tyr Ser Asp Lys Pro Asp Thr Asn Ser
        35                  40                  45

```
Met Met Leu Asn His Ser Ala Glu Glu Leu Glu Ser Ser Asp Arg Ala
     50                  55                  60

Asp Ile Leu Ala Ser Leu Pro Leu Leu His Asn Lys Asp Val Val Asp
 65              70                  75                      80

Ile Gly Ala Gly Ile Gly Arg Phe Thr Thr Val Leu Ala Glu Thr Ala
                     85                  90                  95

Arg Trp Val Leu Ser Thr Asp Phe Ile Asp Ser Phe Ile Lys Lys Asn
             100                 105                 110

Gln Glu Arg Asn Ala His Leu Gly Asn Ile Asn Tyr Gln Val Gly Asp
         115                 120                 125

Ala Val Gly Leu Lys Met Glu Ser Asn Ser Val Asp Leu Val Phe Thr
     130                 135                 140

Asn Trp Leu Met Met Tyr Leu Ser Asp Glu Thr Val Glu Phe Ile
145                 150                 155                 160

Phe Asn Cys Met Arg Trp Leu Arg Ser His Gly Ile Val His Leu Arg
                 165                 170                 175

Glu Ser Cys Ser Glu Pro Ser Thr Gly Arg Ser Lys Ala Lys Ser Met
             180                 185                 190

His Asp Thr Ala Asn Ala Asn Pro Thr His Tyr Arg Phe Ser Ser Leu
         195                 200                 205

Tyr Ile Asn Leu Leu Arg Ala Ile Arg Tyr Arg Asp Val Asp Asn Lys
     210                 215                 220

Leu Trp Arg Phe Asn Val Gln Trp Ser Cys Ser Val Pro Thr Tyr Ile
225                 230                 235                 240

Lys Arg Ser Asn Asn Trp Arg Gln Val His Trp Leu Ala Glu Lys Val
                 245                 250                 255

Pro Ala Glu Asp Gly Ala Lys Gly Thr Ser Phe Asn Glu Leu Val Glu
             260                 265                 270

Leu Ile Lys Asn Thr Trp Gln Asn Glu Gln Glu Ala Trp Asp Ala Lys
         275                 280                 285

Leu Asp Asp Glu Lys Tyr Val Trp Thr Asp Lys Val Phe Ser Ser Ala
     290                 295                 300

Leu Thr Ser Leu Pro Ser Asn Ser Thr Phe Phe Leu Tyr Thr Pro Arg
305                 310                 315                 320

Thr Val Ser Pro Tyr Cys His Ile Asn Ala His Thr Leu Ala Glu Thr
                 325                 330                 335

Phe Asn Ala Asn Val Trp Asn Thr Glu Ile Ile Pro Glu Tyr Tyr Arg
             340                 345                 350

Thr Ser Leu Thr Lys Ser Asn Asn Leu Lys Asp Gln Arg Val Arg Phe
         355                 360                 365

Gly Trp Asn Gln Ser Leu Thr Asp Ser Val Thr Tyr Trp Gln Gln Lys
     370                 375                 380

Asp Ala Leu Phe Asp Val Phe Val Ala Thr Glu Phe Leu Ser Thr Val
385                 390                 395                 400

Asp Asp Glu Thr Ile Arg Gln Leu Pro Asn Val Met Ser Asp Gly Ala
                 405                 410                 415

Lys Phe Ile Thr Leu Glu Pro Val Asp Glu Val Asn Glu Ala Glu Met
             420                 425                 430

Lys Gln Arg Ile Gln Glu Leu Gly Tyr Thr Leu Lys Ser Phe Thr Asp
         435                 440                 445

Val Thr Asp Gln Cys Ile Glu Ala Gln Glu Gln Tyr Phe Lys Asp His
     450                 455                 460

Glu Gln Leu Arg Asp Glu Lys Val Ile Arg Lys Asn Trp Val Leu Leu
465                 470                 475                 480
```

Glu Leu Thr His

<210> SEQ ID NO 21
<211> LENGTH: 437
<212> TYPE: PRT
<213> ORGANISM: Caenorhabditis elegans

<400> SEQUENCE: 21

Met Ser Ser Leu Ser Ile Pro Arg Gln Ser Leu Tyr Tyr Val Asn Lys
  1               5                  10                  15

Val Thr Glu Gly Arg Ser Val Ser Asn Val Gln Val Ser Pro Cys
             20                  25                  30

Gln Lys Gln Gly Gln Thr Tyr Val Thr Ala Phe Thr Pro Leu Thr Ser
             35                  40                  45

Asn Val Gln Val His Thr Ser Leu Glu Gln Leu Ser Thr Ile Arg Asn
 50                  55                  60

Ala Asp Val Leu Ile Phe Asn Asn Ala Leu Ser Gln Ile Ile Thr Asn
 65                  70                  75                  80

Ala Asp Leu Leu Thr Asp Phe Leu Lys Asn Ala Thr Asn Ala Thr Ala
             85                  90                  95

Ile Gly Gly Thr Val Ile Ile Arg Glu Asp Leu Lys Asp Cys Ser Asp
            100                 105                 110

Lys Arg Gln Val Ala Arg Leu Thr Asp Tyr Phe Asp Val Phe Arg Thr
            115                 120                 125

Thr Asp Ser Asp Gly Asn Asn Thr Gly Leu Asp Leu Tyr Thr Val Asp
130                 135                 140

Gln Val Glu His Ser Asn Tyr Val Glu Gln Asn Phe Leu Asp Phe Ile
145                 150                 155                 160

Phe Val Phe Arg Lys Lys Val Phe Ala Pro Thr Thr Asp Ala Thr Ile
                165                 170                 175

Thr Phe Arg Asp Phe Leu Asp Lys Thr Gln Tyr Thr Asn Thr Gly Ile
            180                 185                 190

Asp Ala Tyr Glu Trp Met Phe Gly Val Asn Phe Ile Ser Pro Gly Gly
            195                 200                 205

Tyr Asp Glu Asn Leu Lys Ile Ile Lys Arg Phe Gly Asp Phe Lys Pro
210                 215                 220

Gly Gln Thr Met Leu Asp Ile Gly Val Gly Ile Gly Gly Gly Ala Arg
225                 230                 235                 240

Gln Val Ala Asp Glu Phe Gly Val His Val His Gly Ile Asp Leu Ser
            245                 250                 255

Ser Asn Met Leu Ala Ile Ala Leu Glu Arg Leu His Glu Glu Lys Asp
            260                 265                 270

Ser Arg Val Lys Tyr Ser Ile Thr Asp Ala Leu Val Tyr Gln Phe Glu
            275                 280                 285

Asp Asn Ser Phe Asp Tyr Val Phe Ser Arg Asp Cys Ile Gln His Ile
            290                 295                 300

Pro Asp Thr Glu Lys Leu Phe Ser Arg Ile Tyr Lys Ala Leu Lys Pro
305                 310                 315                 320

Gly Gly Lys Val Leu Ile Thr Met Tyr Gly Lys Gly Tyr Gly Glu Gln
            325                 330                 335

Ser Asp Lys Phe Lys Thr Tyr Val Ala Gln Arg Ala Tyr Phe Leu Lys
            340                 345                 350

Asn Leu Lys Glu Ile Ala Asp Ile Ala Asn Lys Thr Gly Phe Val Asn
            355                 360                 365

Val Gln Thr Glu Asn Met Thr Pro Arg Phe Lys Glu Ile Leu Leu Glu
    370                 375                 380

Glu Arg Gly His Leu Glu Gln Asn Glu Ala Glu Phe Met Ser Lys Phe
385                 390                 395                 400

Thr Gln Arg Glu Arg Asp Ser Leu Ile Ser Gly Trp Thr Asp Lys Leu
                405                 410                 415

Gly Tyr Ile Glu Lys Asp Asn His Asn Trp Asn Phe Phe Leu Ala Gln
                420                 425                 430

Lys Pro Phe Pro Lys
        435

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
gtaatacgac tcactatagg gc                                          22

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
aattaaccct cactaaaggg                                             20

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
gatttaggtg acactatag                                              19

<210> SEQ ID NO 25
<211> LENGTH: 17
<212> TYPE: DNA
<213> ORGANISM: Artificial Sequence
<220> FEATURE:
<223> OTHER INFORMATION: primer

<400> SEQUENCE: 25
atgcctgcgg cagagcg                                                17

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
ggccacgcgt cgactagtac                                             20

<210> SEQ ID NO 27
<211> LENGTH: 22
<212> TYPE: DNA
<213> ORGANISM: Artificial Sequence

```
<220> FEATURE:
<223> OTHER INFORMATION: primer

<400> SEQUENCE: 27
gggtttaatt acccaagttt ga                                        22

<210> SEQ ID NO 28
<211> LENGTH: 37
<212> TYPE: DNA
<213> ORGANISM: Artificial Sequence
<220> FEATURE:
<223> OTHER INFORMATION: primer

<400> SEQUENCE: 28
ggccacgcgt cgactagtac tttttttttt tttttt                         37

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
atggtgaacg ttcgtcgtgc                                           20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
catacgtatt tctcatcatc                                           20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
ccagattatt accaacgccg                                           20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tgaacttaca tagattcttg                                           20

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
gcaattgaat atatgcggat g                                         21
```

```
<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
ctatccgaat tggaatgtag cg                                              22

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
cattccaatt cggatagtat c                                               21

<210> SEQ ID NO 36
<211> LENGTH: 23
<212> TYPE: DNA
<213> ORGANISM: Artificial Sequence
<220> FEATURE:
<223> OTHER INFORMATION: primer

<400> SEQUENCE: 36
cgactggagc acgaggacac tga                                             23

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
ggacactgac atggactgaa ggagta                                          26

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
caacggattt catcgaatcg                                                 20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
ccacgtcttt gttggttagg                                                 20

<210> SEQ ID NO 40
<211> LENGTH: 44
<212> TYPE: DNA
<213> ORGANISM: Artificial Sequence
<220> FEATURE:
<223> OTHER INFORMATION: primer

<400> SEQUENCE: 40
```

```
cgacuggagc acgaggacac ugacauggac ugaaggagua gaaa         44
```

<210> SEQ ID NO 41
<211> LENGTH: 22
<212> TYPE: DNA
<213> ORGANISM: Artificial Sequence
<220> FEATURE:
<223> OTHER INFORMATION: primer

<400> SEQUENCE: 41

```
ggttttaacc cagtatctca ag                                 22
```

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42

```
gcatcagcaa tttgatattc                                    20
```

<210> SEQ ID NO 43
<211> LENGTH: 18
<212> TYPE: DNA
<213> ORGANISM: Artificial Sequence
<220> FEATURE:
<223> OTHER INFORMATION: primer

<400> SEQUENCE: 43

```
ccgcaatatc cagaagac                                      18
```

<210> SEQ ID NO 44
<211> LENGTH: 18
<212> TYPE: DNA
<213> ORGANISM: Artificial Sequence
<220> FEATURE:
<223> OTHER INFORMATION: primer

<400> SEQUENCE: 44

```
cagatctcga tacattcg                                      18
```

<210> SEQ ID NO 45
<211> LENGTH: 19
<212> TYPE: DNA
<213> ORGANISM: Artificial Sequence
<220> FEATURE:
<223> OTHER INFORMATION: primer

<400> SEQUENCE: 45

```
gttctgaacc atcaacaag                                     19
```

<210> SEQ ID NO 46
<211> LENGTH: 19
<212> TYPE: DNA
<213> ORGANISM: Artificial Sequence
<220> FEATURE:
<223> OTHER INFORMATION: primer

<400> SEQUENCE: 46

```
gctgaagtta atgaacatc                                     19
```

NEMATODE PHOSPHOETHANOLAMINE N-METHYLTRANSFERASE-LIKE SEQUENCES

CLAIM OF PRIORITY

This application is a divisional of U.S. application Ser. No. 10/602,268, filed on Jun. 23, 2003, now U.S. Pat. No. 7,442,533, which claims priority to U.S. Provisional Patent Application Ser. No. 60/390,490, filed on Jun. 21, 2002, all of which are hereby incorporated by reference.

BACKGROUND

Nematodes (derived from the Greek word for thread) are active, flexible, elongate, organisms that live on moist surfaces or in liquid environments, including films of water within soil and moist tissues within other organisms. While only 20,000 species of nematode have been identified, it is estimated that 40,000 to 10 million actually exist. Some species of nematodes have evolved to be very successful parasites of both plants and animals and are responsible for significant economic losses in agriculture and livestock and for morbidity and mortality in humans (Whitehead (1998) *Plant Nematode Control*. CAB International, New York).

Nematode parasites of plants can inhabit all parts of plants, including roots, developing flower buds, leaves, and stems. Plant parasites are classified on the basis of their feeding habits into the broad categories: migratory ectoparasites, migratory endoparasites, and sedentary endoparasites. Sedentary endoparasites, which include the root knot nematodes (*Meloidogyne*) and cyst nematodes (*Globodera* and *Heterodera*) induce feeding sites and establish long-term infections within roots that are often very damaging to crops (Whitehead, supra). It is estimated that parasitic nematodes cost the horticulture and agriculture industries in excess of $78 billion worldwide a year, based on an estimated average 12% annual loss spread across all major crops. For example, it is estimated that nematodes cause soybean losses of approximately $3.2 billion annually worldwide (Barker et al. (1994) *Plant and Soil Nematodes: Societal Impact and Focus for the Future*. The Committee on National Needs and Priorities in Nematology. Cooperative State Research Service, US Department of Agriculture and Society of Nematologists). Several factors make the need for safe and effective nematode controls urgent. Continuing population growth, famines, and environmental degradation have heightened concern for the sustainability of agriculture, and new government regulations may prevent or severely restrict the use of many available agricultural anthelmintic agents.

There are a very small array of chemicals available to control nematodes (Becker (1999) *Agricultural Research Magazine* 47(3):22-24; U.S. Pat. Nos. 6,048,714). Nevertheless, the application of chemical nematicides remains the major means of nematode control. In general, chemical nematicides are highly toxic compounds known to cause substantial environmental damage and are increasingly restricted in the amounts and locations in which then can be used. For example, the soil fumigant methyl bromide which has been used effectively to reduce nematode infestations in a variety of specialty crops, is regulated under the U.N. Montreal Protocol as an ozone-depleting substance and is scheduled for elimination in 2005 in the US (Carter (2001) *California Agriculture*, 55(3):2). It is expected that strawberry and other commodity crop industries will be significantly impacted if a suitable replacement for methyl bromide is not found. Similarly, broad-spectrum nematicides such as Telone (various formulations of 1,3-dichloropropene) have significant restrictions on their use because of toxicological concerns (Carter (2001) *California Agriculture*, Vol. 55(3):12-18).

The macrocyclic lactones (e.g., avermectins and milbemycins) and delta-toxins from *Bacillus thuringiensis* (Bt) are chemicals that in principle provide excellent specificity and efficacy and should allow environmentally safe control of plant parasitic nematodes. Unfortunately, in practice, these two nematicidal agents have proven less effective in agricultural applications against root pathogens. Although certain avermectins show exquisite activity against plant parasitic nematodes these chemicals are hampered by poor bioavailability due to their light sensitivity, degradation by soil microorganisms and tight binding to soil particles (Lasota & Dybas (1990) *Acta Leiden* 59(1-2):217-225; Wright & Perry (1998) Musculature and Neurobiology. In: The Physiology and Biochemistry of Free-Living and Plant-parasitic Nematodes (eds R. N. Perry & D. J. Wright), CAB International 1998). Consequently despite years of research and extensive use against animal parasitic nematodes, mites and insects (plant and animal applications), macrocyclic lactones (e.g., avermectins and milbemycins) have never been commercially developed to control plant parasitic nematodes in the soil.

Bt delta toxins must be ingested to affect their target organ, the brush border of midgut epithelial cells (Marroquin et al. (2000) *Genetics*. 155(4):1693-1699). Consequently they are not anticipated to be effective against the dispersal, non-feeding, juvenile stages of plant parasitic nematodes in the field. Because juvenile stages only commence feeding when a susceptible host has been infected, nematicides may need to penetrate the plant cuticle to be effective. Transcuticular uptake of a 65-130 kDa protein—the size of typical Bt delta toxins—is unlikely. Furthermore, soil mobility is expected to be relatively poor. Even transgenic approaches are hampered by the size of Bt delta toxins because delivery in planta is likely to be constrained by the exclusion of large particles by the feeding tubes of certain plant parasitic nematodes such as *Heterodera* (Atkinson et al. (1998) Engineering resistance to plant-parasitic nematodes. In: The Physiology and Biochemistry of Free-Living and Plant-parasitic Nematodes (eds R. N. Perry & D. J. Wright), CAB International 1998).

Fatty acids are a class of natural compounds that have been investigated as alternatives to the toxic, non-specific organophosphate, carbamate and fumigant pesticides (Stadler et al. (1994) *Planta Medica* 60(2):128-132; U.S. Pat. Nos. 5,192,546; 5,346,698; 5,674,897; 5,698,592; 6,124,359). It has been suggested that fatty acids derive their pesticidal effects by adversely interfering with the nematode cuticle or hypodermis via a detergent (solubilization) effect, or through direct interaction of the fatty acids and the lipophilic regions of target plasma membranes (Davis et al. (1997) *Journal of Nematology* 29(4S):677-684). In view of this predicted mode of action it is not surprising that fatty acids are used in a variety of pesticidal applications including as herbicides (e.g., SCYTHE by Dow Agrosciences is the C9 saturated fatty acid pelargonic acid), bactericides and fungicides (U.S. Pat. Nos. 4,771,571; 5,246,716) and insecticides (e.g., SAFER INSECTICIDAL SOAP by Safer, Inc.).

The phytotoxicity of fatty acids has been a major constraint on their general use in post-plant agricultural applications (U.S. Pat. No. 5,093,124) and the mitigation of these undesirable effects while preserving pesticidal activity is a major area of research. Post-plant applications are desirable because of the relatively short half-life of fatty acids under field conditions.

The esterification of fatty acids can significantly decrease their phytotoxicity (U.S. Pat. Nos. 5,674,897; 5,698,592;

6,124,359). Such modifications can however lead to loss of nematicidal activity as is seen for linoleic, linolenic and oleic acid (Stadler et al. (1994) *Planta Medica* 60(2):128-132) and it may be impossible to completely decouple the phytotoxicity and nematicidal activity of pesticidal fatty acids because of their non-specific mode of action. Perhaps not surprisingly, the nematicidal fatty acid pelargonic acid methyl ester (U.S. Pat. Nos. 5,674,897; 5,698,592; 6,124,359) shows a relatively small "therapeutic window" between the onset of pesticidal activity and the observation of significant phytotoxicity (Davis et al. (1997) *J Nematol* 29(4S):677-684). This is the expected result if both the phytotoxicity and the nematicidial activity derive from the non-specific disruption of plasma membrane integrity.

Ricinoleic acid, the major component of castor oil, has been shown to have an inhibitory effect on water and electrolyte absorption using everted hamster jejunal and ileal segments (Gaginella et al. (1975) *J Pharmacol Exp Ther* 195(2): 355-61) and to be cytotoxic to isolated intestinal epithelial cells (Gaginella et al. (1977) *J Pharmacol Exp Ther* 201(1): 259-66). These features are likely the source of the laxative properties of castor oil which is given as a purgative in humans and livestock (e.g., castor oil is a component of some de-worming protocols because of its laxative properties). In contrast, the methyl ester of ricinoleic acid is ineffective at suppressing water absorption in the hamster model (Gaginella et al. (1975) *J Pharmacol Exp Ther* 195(2):355-61).

Many plant species are known to be highly resistant to nematodes. The best documented of these include marigolds (*Tagetes* spp.), rattlebox (*Crotalaria spectabilis*), chrysanthemums (*Chrysanthemum* spp.), castor bean (*Ricinus communis*), margosa (*Azardiracta indica*), and many members of the family Asteraceae (family Compositae) (Hackney & Dickerson. (1975) *J Nematol* 7(1):84-90). In the case of the Asteraceae, the photodynamic compound alpha-terthienyl has been shown to account for the strong nematicidal activity of the roots. Castor beans are plowed under as a green manure before a seed crop is set. However, a significant drawback of the castor plant is that the seed contains toxic compounds (such as ricin) that can kill humans, pets, and livestock and is also highly allergic. In many cases however, the active principle(s) for plant nematicidal activity has not been discovered and it remains difficult to derive commercially successful nematicidal products from these resistant plants or to transfer the resistance to agronomically important crops such as soybeans and cotton.

Genetic resistance to certain nematodes is available in some commercial cultivars (e.g., soybeans), but these are restricted in number and the availability of cultivars with both desirable agronomic features and resistance is limited. The production of nematode resistant commercial varieties by conventional plant breeding based on genetic recombination through sexual crosses is a slow process and is often further hampered by a lack of appropriate germplasm.

There remains an urgent need to develop environmentally safe, target-specific ways of controlling plant parasitic nematodes. In the specialty crop markets, economic hardship resulting from nematode infestation is highest in strawberries, bananas, and other high value vegetables and fruits. In the high-acreage crop markets, nematode damage is greatest in soybeans and cotton. There are however, dozens of additional crops that suffer from nematode infestation including potato, pepper, onion, citrus, coffee, sugarcane, greenhouse ornamentals and golf course turf grasses.

Nematode parasites of vertebrates (e.g., humans, livestock and companion animals) include gut roundworms, hookworms, pinworms, whipworms, and filarial worms. They can be transmitted in a variety of ways, including by water contamination, skin penetration, biting insects, or by ingestion of contaminated food.

In domesticated animals, nematode control or "de-worming" is essential to the economic viability of livestock producers and is a necessary part of veterinary care of companion animals. Parasitic nematodes cause mortality in animals (e.g., heartworm in dogs and cats) and morbidity as a result of the parasites' inhibiting the ability of the infected animal to absorb nutrients. The parasite-induced nutrient deficiency leads to disease and stunted growth in livestock and companion animals. For instance, in cattle and dairy herds, a single untreated infection with the brown stomach worm can permanently restrict an animal's ability to convert feed into muscle mass or milk.

Two factors contribute to the need for novel anthelmintics and vaccines to control animal parasitic nematodes. First, some of the more prevalent species of parasitic nematodes of livestock are building resistance to the anthelmintic drugs available currently, meaning that these products will eventually lose their efficacy. These developments are not surprising because few effective anthelmintic drugs are available and most have been used continuously. Some parasitic species have developed resistance to most of the anthelmintics (Geents et al. (1997) *Parasitology Today* 13:149-151; Prichard (1994) *Veterinary Parasitology* 54:259-268). The fact that many of the anthelmintic drugs have similar modes of action complicates matters, as the loss of sensitivity of the parasite to one drug is often accompanied by side resistance—that is, resistance to other drugs in the same class (Sangster & Gill (1999) *Parasitology Today* 15(4):141-146). Secondly, there are some issues with toxicity for the major compounds currently available.

Infections by parasitic nematode worms result in substantial human mortality and morbidity, especially in tropical regions of Africa, Asia, and the Americas. The World Health Organization estimates 2.9 billion people are infected, and in some areas, 85% of the population carries worms. While mortality is rare in proportion to infections, morbidity is substantial and rivals diabetes and lung cancer in worldwide disability adjusted life year (DALY) measurements.

Examples of human parasitic nematodes include hookworms, filarial worms, and pinworms. Hookworms (1.3 billion infections) are the major cause of anemia in millions of children, resulting in growth retardation and impaired cognitive development. Filarial worm species invade the lymphatics, resulting in permanently swollen and deformed limbs (elephantiasis), and the eyes, causing African river blindness. The large gut roundworm *Ascaris lumbricoides* infects more than one billion people worldwide and causes malnutrition and obstructive bowel disease. In developed countries, pinworms are common and often transmitted through children in daycare.

Even in asymptomatic parasitic infections, nematodes can still deprive the host of valuable nutrients and increase the ability of other organisms to establish secondary infections. In some cases, infections can cause debilitating illnesses and can result in anemia, diarrhea, dehydration, loss of appetite, or death.

Despite some advances in drug availability and public health infrastructure and the near elimination of one tropical nematode (the water-borne Guinea worm), most nematode diseases have remained intractable problems. Treatment of hookworm diseases with anthelmintic drugs, for instance, has not provided adequate control in regions of high incidence because rapid re-infection occurs after treatment. In fact, over the last 50 years, while nematode infection rates have fallen in the United States, Europe, and Japan, the overall number of infections worldwide has kept pace with the growing world population. Large scale initiatives by regional governments, the World Health Organization, foundations, and pharmaceutical companies are now underway attempting to control nematode infections with currently available tools, including three programs for control of Onchocerciasis (river blindness) in Africa and the Americas using ivermectin and vector control; The Global Alliance to Eliminate Lymphatic Filariasis using DEC, albendazole, and ivermectin; and the highly successful Guinea Worm Eradication Program. Until safe and effective vaccines are discovered to prevent parasitic nematode infections, anthelmintic drugs will continue to be used to control and treat nematode parasitic infections in both humans and domestic animals.

Finding effective compounds and vaccines against parasitic nematodes has been complicated by the fact that the parasites have not been amenable to culturing in the laboratory. Parasitic nematodes are often obligate parasites (i.e., they can only survive in their respective hosts, such as in plants, animals, and/or humans) with slow generation times. Thus, they are difficult to grow under artificial conditions, making genetic and molecular experimentation difficult or impossible. To circumvent these limitations, scientists have used *Caenorhabidits elegans* as a model system for parasitic nematode discovery efforts.

*C. elegans* is a small free-living bacteriovorous nematode that for many years has served as an important model system for multicellular animals (Burglin (1998) *Int. J. Parasitol.* 28(3):395-411). The genome of *C. elegans* has been completely sequenced and the nematode shares many general developmental and basic cellular processes with vertebrates (Ruvkin et al. (1998) *Science* 282:2033-41). This, together with its short generation time and ease of culturing, has made it a model system of choice for higher eukaryotes (Aboobaker et al. (2000) *Ann. Med.* 32:23-30).

Although *C. elegans* serves as a good model system for vertebrates, it is an even better model for study of parasitic nematodes, as *C. elegans* and other nematodes share unique biological processes not found in vertebrates. For example, unlike vertebrates, nematodes produce and use chitin, have gap junctions comprised of innexin rather than connexin and contain glutamate-gated chloride channels rather than glycine-gated chloride channels (Bargmann (1998) *Science* 282: 2028-33). The latter property is of particular relevance given that the avermectin class of drugs is thought to act at glutamate-gated chloride receptors and is highly selective for invertebrates (Martin (1997) *Vet. J.* 154:11-34).

A subset of the genes involved in nematode-specific processes will be conserved in nematodes and absent or significantly diverged from homologues in other phyla. In other words, it is expected that at least some of the genes associated with functions unique to nematodes will have restricted phylogenetic distributions. The completion of the *C. elegans* genome project and the growing database of expressed sequence tags (ESTs) from numerous nematodes facilitate identification of these "nematode-specific" genes. In addition, conserved genes involved in nematode-specific processes are expected to retain the same or very similar functions in different nematodes. This functional equivalence has been demonstrated in some cases by transforming *C. elegans* with homologous genes from other nematodes (Kwa et al. (1995) *J. Mol. Biol.* 246:500-10; Redmond et al. (2001) *Mol. Biochem. Parasitol.* 112:125-131). This sort of functional conservations has also been shown in cross phyla comparisons for conserved genes and is expected to be more robust among species within a phylum. Consequently, *C. elegans* and other free-living nematode species are likely excellent surrogates for parasitic nematodes with respect to conserved nematode processes.

Many expressed genes in *C. elegans* and certain genes in other free-living nematodes can be "knocked out" genetically by a process referred to as RNA interference (RNAi), a technique that provides a powerful experimental tool for the study of gene function in nematodes (Fire et al. (1998) *Nature* 391(6669):806-811; Montgomery et al. (1998) *Proc. Natl. Acad Sci USA* 95(26):15502-15507). Treatment of a nematode with double-stranded RNA of a selected gene can destroy expressed sequences corresponding to the selected gene thus reducing expression of the corresponding protein. By preventing the translation of specific proteins, their functional significance and essentiality to the nematode can be assessed. Determination of essential genes and their corresponding proteins using *C. elegans* as a model system will assist in the rational design of anti-parasitic nematode control products.

SUMMARY

The invention features nucleic acid molecules encoding *Ascaris suum, Haemonchus contortus, Meloidogyne incognita, Meloidogyne javanica* and *Strongyloides stercoralis* phosphoethanolamine n-methyltransferase-like (PEAMT-like) proteins. *A. suum* is the large roundworm of pigs and is closely related to *Ascaris lumbricoides*, a major human pathogen. *H. contortus* is a parasite of ruminants (sheep, goats, cattle and other wild ruminants) leading to emaciation, anemia and in certain cases death. As such it represents a major economic scourge. *M. javanica* and *M. incognita* are Root Knot Nematodes that cause substantial damage to several crops, including cotton, tobacco, pepper, and tomato. *S. stercoralis* is a nematode parasite that infects humans, primates, and dogs. It is one of the few nematodes that can multiply within its host and can multiply unchecked in immunosuppressed individuals.

The PEAMT-like nucleic acids and polypeptides of the invention allow for the identification of nematode species. The nucleic acids and polypeptides of the invention also allow for the identification of compounds that bind to or alter the activity of PEAMT-like polypeptides. Such compounds may provide a means for combating diseases and infestations caused by nematodes, particularly those caused by *A. suum* in pigs, *A. lumbricoides* in humans and other ascarid species in a variety of animals, *H. contortus* in ruminants, *M. javanica* and *M. incognita* (e.g., in tobacco, cotton, pepper, or tomato plants) and *S. stercoralis* (e.g., in humans, primates and dogs).

The invention is based, in part, on the identification of a cDNA encoding *A. suum* PEAMT1 (SEQ ID NO: 1). This 1786 nucleotide cDNA has a 1380 nucleotide open reading frame (SEQ ID NO: 13) encoding a 460 amino acid polypeptide (SEQ ID NO: 7).

The invention is also based, in part, on the identification of a cDNA encoding *H. contortus* PEAMT1 (SEQ ID NO: 2). This 1669 nucleotide cDNA has a 1380 nucleotide open reading frame (SEQ ID NO: 14) encoding a 460 amino acid polypeptide (SEQ ID NO: 8).

The invention is also based, in part, on the identification of a cDNA encoding *M. incognita* PEAMT1 (SEQ ID NO: 3). This 1472 nucleotide cDNA has a 1371 nucleotide open reading frame (SEQ ID NO: 15) encoding a 457 amino acid polypeptide (SEQ ID NO: 9).

The invention is based, in part, on the identification of a cDNA encoding *S. stercoralis* PEAMT1 (SEQ ID NO: 4). This 1580 nucleotide cDNA has a 1407 nucleotide open reading frame (SEQ ID NO: 16) encoding a 469 amino acid polypeptide (SEQ ID NO: 10).

The invention is also based, in part, on the identification of a cDNA encoding *A. suum* PEAMT2 (SEQ ID NO: 5). This 1533 nucleotide cDNA has a 1311 nucleotide open reading frame (SEQ ID NO: 17) encoding a 437 amino acid polypeptide (SEQ ID NO: 11).

The invention is based, in part, on the identification of a cDNA encoding *M. javanica* PEAMT2 (SEQ ID NO: 6). This 1534 nucleotide cDNA has a 1416 nucleotide open reading frame (SEQ ID NO: 18) encoding a 472 amino acid polypeptide (SEQ ID NO: 12).

In one aspect, the invention features novel nematode phosphoethanolamine n-methyltransferase-like polypeptides. Such polypeptides include purified polypeptides having the amino acid sequences set forth in SEQ ID NO: 7, 8, 9, 10, 11 or 12. Also included are polypeptides having an amino acid sequence that is at least about 60%, 70%, 75%, 80%, 85%, 90%, 95%, or 98% identical to SEQ ID NO: 7, 8, 9, 10, 11 and/or 12 as well as polypeptides having a sequence that differs from that of SEQ ID NO: 7, 8, 9, 10, 11 or 12 at 20, 15, 10, 9, 8, 7, 6, 5, 4, 3, 2, or 1 residues (amino acids). The purified polypeptides can be encoded by a nematode gene, e.g., a nematode gene other than *C. elegans*. For example, the purified polypeptide has a sequence other than SEQ ID NO: 19, 20 or 21 (*C. elegans* PEAMT1-like or PEAMT2-like proteins). The purified polypeptides can further include a heterologous amino acid sequence, e.g., an amino-terminal or carboxy-terminal sequence. Also featured are purified polypeptide fragments of the aforementioned PEAMT-like polypeptides, e.g., a fragment of at least about 20, 30, 40, 50, 75, 85, 104, 106, 113 150, 200, 250, 300, 350, 400, 450 or 470 amino acids. Non-limiting examples of such fragments include: fragments from about amino acid 1 to 50, 1 to 75, 1 to 89, 1 to 91, 1 to 99, 1 to 100, 1 to 125, 51 to 113, 93 to 104, 99 to 113, 93 to 106, 228 to 262, 250 to 280, 290 to 322, and 317 to 352 of SEQ ID NO: 7, 8, 9, 10, 11 and 12. The polypeptide or fragment thereof can be modified, e.g., processed, truncated, modified (e.g. by glycosylation, phosphorylation, acetylation, myristylation, prenylation, palmitoylation, amidation, addition of glycerophosphatidyl inositol), or any combination of the above. Certain PEAMT-like polypeptides comprise a sequence of 400, 425, 450, 475, 500 amino acids or fewer.

The invention also features polypeptides comprising, consisting essentially of or consisting of such polypeptides.

In another aspect, the invention features novel isolated nucleic acid molecules encoding nematode PEAMT-like polypeptides. Such isolated nucleic acid molecules include nucleic acids comprising, consisting essentially of or consisting of the nucleotide sequence set forth in SEQ ID NO: 1, 2, 3, 4, 5 and 6 or SEQ ID NO: 13, 14, 15, 16, 17 and 18. Also included are isolated nucleic acid molecules having the same sequence as or encoding the same polypeptide as a nematode phosphoethanolamine n-methyltransferase-like gene (other than *C. elegans* PEAMT-like genes).

Also featured are: 1) isolated nucleic acid molecules having a strand that hybridizes under low stringency conditions to a single stranded probe of the sequences of SEQ ID NO: 1, 2, 3, 4, 5 and/or 6, or their complements and, optionally, encodes polypeptides of between 400 and 500 amino acids; 2) isolated nucleic acid molecules having a strand that hybridizes under high stringency conditions to a single stranded probe of the sequence of SEQ ID NO: 1, 2, 3, 4, 5 and/or 6 or their complements and, optionally, encodes polypeptides of between 400 and 500 amino acids; 3) isolated nucleic acid fragments of a PEAMT-like nucleic acid molecule, e.g., a fragment of SEQ ID NO: 1, 2, 3, 4, 5 and/or 6 that is about 500, 750, 1000, 1250, 1500, 1750 or more nucleotides in length or ranges between such lengths; and 4) oligonucleotides that are complementary to a PEAMT-like nucleic acid molecule or a PEAMT-like nucleic acid complement, e.g., an oligonucleotide of about 10, 15, 18, 20, 22, 24, 28, 30, 35, 40, 50, 60, 70, 80, or more nucleotides in length. Exemplary oligonucleotides are oligonucleotides which anneal to a site located between nucleotides about 1 to 24, 1 to 48, 1 to 60, 1 to 120, 24 to 48, 24 to 60, 49 to 60, 61 to 180, 381 to 420, 421 to 480, 451 to 466, 451 to 489, 451 to 516, 500 to 1450 of SEQ ID NO: 1, 2, 3, 4, 5 and/or 6. Nucleic acid fragments include the following non-limiting examples: nucleotides about 1 to 200, 100 to 300, 200 to 400, 300 to 500, 300 to 466, 300 to 516, 300 to 489, 489 to 1450 of SEQ ID NO: 1, 2, 3, 4, 5 and/or 6. Also within the invention are nucleic acid molecules that hybridize under stringent conditions to nucleic acid molecule consisting of SEQ ID NO: 1, 2, 3, 4, 5 or 6 and comprise 3,000, 2,000, 1,000 or fewer nucleotides. The isolated nucleic acid can further include a heterologous promoter or other sequences required for transcription or translation of the nucleic acid molecule in a cell, e.g., a mammalian or eukaryotic or prokaryotic cell, operably linked to the PEAMT-like nucleic acid molecule. The isolated nucleic acid molecule can encode a polypeptide having PEAMT enzymatic activity. Thus, as explained in greater detail below, a polypeptide having PEAMT1 enzymatic activity can catalyze the conversion of ethanolamine to monomethylethanolamine, and a polypeptide having PEAMT2 enzymatic catalyzes the converstion of monomethylethanolamine to dimethylethanolamine and the conversion of dimethylethanolamine to choline A molecule featured herein can be from a nematode of the class Araeolaimida, Ascaridida, Chromadorida, Desmodorida, Diplogasterida, Monhysterida, Mononchida, Oxyurida, Rhigonematida, Spirurida, Enoplia, Desmoscolecidae, Rhabditida, or Tylenchida. Alternatively, the molecule can be from a species of the class Rhabditida, particularly a species other than *C. elegans* or *C. briggsae*.

In another aspect, the invention features a vector, e.g., a vector containing an aforementioned nucleic acid. The vector can further include one or more regulatory elements, e.g., a heterologous promoter or elements required for translation. The regulatory elements can be operably linked to the phosphoethanolamine n-methyltransferase-like nucleic acid molecules in order to express a PEAMT-like nucleic acid molecule. In yet another aspect, the invention features a transgenic cell or transgenic organism having in its genome a transgene containing an aforementioned PEAMT-like nucleic acid molecule and a heterologous nucleic acid, e.g., a heterologous promoter.

In still another aspect, the invention features an antibody, e.g., an antibody, antibody fragment, or derivative thereof that binds specifically to an aforementioned polypeptide. Such antibodies can be polyclonal or monoclonal antibodies. The antibodies can be modified, e.g., humanized, rearranged as a single-chain, or CDR-grafted. The antibodies may be directed against a fragment, a peptide, or a discontinuous epitope from a PEAMT-like polypeptide.

In another aspect, the invention features a method of screening for a compound that binds to a nematode PEAMT-like polypeptide, e.g., an aforementioned polypeptide. The method includes providing the nematode polypeptide; contacting a test compound to the polypeptide; and detecting binding of the test compound to the nematode polypeptide. In one embodiment, the method further includes contacting the test compound to a mammalian PEAMT-like polypeptide and detecting binding of the test compound to the mammalian PEAMT-like polypeptide. A test compound that binds the nematode PEAMT-like polypeptide with at least 2-fold, 5-fold, 10-fold, 20-fold, 50-fold, or 100-fold affinity greater relative to its affinity for the mammalian (e.g., a human) PEAMT-like polypeptide can be identified.

The invention also features methods for identifying compounds that alter (increase or decrease) the activity of a nematode phosphoethanolamine n-methyltransferase-like polypeptide. The method includes contacting the test compound to the nematode PEAMT-like polypeptide and detecting a PEAMT-like activity. A decrease in the level of PEAMT-like activity of the polypeptide relative to the level of PEAMT-like activity of the polypeptide in the absence of the test compound is an indication that the test compound is an inhibitor of the PEAMT-like activity. In still another embodiment, the method further includes contacting a test compound such as an allosteric inhibitor or other types of inhibitors that prevent binding of the PEAMT-like polypeptide to other molecules or proteins. Such inhibitory compounds are potential selective agents for reducing the viability of a nematode expressing a PEAMT-like polypeptide, e.g., *A. suum, H. contortus, M. incognita M. javanica* and/or *S. stercoralis*. These methods can also include contacting the compound with a plant (e.g., a spinach) phosphoethanolamine n-methyltransferase polypeptide; and detecting a PEAMT-like activity. A compound that decreases nematode phosphoethanolamine n-methyltransferase activity to a greater extent than it decreases plant PEAMT-like polypeptide activity could be useful as a selective inhibitor of the nematode polypeptide. A desirable compound can exhibit 2-fold, 5-fold, 10-fold, 20-fold, 50-fold, 100-fold or greater selective activity against the nematode polypeptide.

Another featured method is a method of screening for a compound that alters (increases or decreases) an activity of a phosphoethanolamine n-methyltransferase-like polypeptide or alters binding or regulation of other polypeptides by PEAMT. The method includes providing the polypeptide; contacting a test compound to the polypeptide; and detecting an PEAMT-like activity or the activity of polypeptides bound or regulated by the PEAMT, wherein a change in activity of PEAMT-like polypeptides or other downstream polypeptides relative to the PEAMT-like activity of the polypeptide or downstream polypeptides in the absence of the test compound is an indication that the test compound alters the activity of the polypeptide(s). The method can further include contacting the test compound to a plant (e.g., a spinach) phosphoethanolamine n-methyltransferase polypeptide and measuring the methyltransferase activity of the plant PEAMT polypeptide. A test compound that alters the activity of the nematode PEAMT-like polypeptide at a given concentration and that does not substantially alter the activity of the plant methyltransferase polypeptide or downstream polypeptides at the given concentration can be identified. An additional method includes screening for both binding to a PEAMT-like polypeptide and for an alteration in the activity of a PEAMT-like polypeptide. Yet another featured method is a method of screening for a compound that alters (increases or decreases) the viability or fitness of a transgenic cell or organism or nematode. The transgenic cell or organism has a transgene that expresses a phosphoethanolamine n-methyltransferase-like polypeptide. The method includes contacting a test compound to the transgenic cell or organism and detecting changes in the viability or fitness of the transgenic cell or organism. This alteration in viability or fitness can be measured relative to an otherwise identical cell or organism that does not harbor the transgene.

Also featured is a method of screening for a compound that alters the expression of a nematode nucleic acid encoding a phosphoethanolamine n-methyltransferase-like polypeptide, e.g. a nucleic acid encoding a *A. suum, H. contortus M. incognita M. javanica* and/or *S. stercoralis* PEAMT-like polypeptide. The method includes contacting a cell, e.g., a nematode cell, with a test compound and detecting expression of a nematode nucleic acid encoding a PEAMT-like polypeptide, e.g., by hybridization to a probe complementary to the nematode nucleic acid encoding a PEAMT-like polypeptide or by contacting polypeptides isolated from the cell with a compound, e.g., antibody that binds a PEAMT-like polypeptide. Compounds identified by the method are also within the scope of the invention.

In yet another aspect, the invention features a method of treating a disorder (e.g., an infection) caused by a nematode, e.g., *A. suum, H. contortus, M. incognita, M. javanica* and/or *S. stercoralis*, in a subject, e.g., a host plant or host animal. The method includes administering to the subject an effective amount of an inhibitor of a PEAMT-like polypeptide activity or an inhibitor of expression of a PEAMT-like polypeptide. Non-limiting examples of such inhibitors include: an antisense nucleic acid (or PNA) to an PEAMT-like nucleic acid, an antibody to a PEAMT-like polypeptide, or a small molecule identified as a PEAMT-like polypeptide inhibitor by a method described herein.

A "purified polypeptide", as used herein, refers to a polypeptide that has been separated from other proteins, lipids, and nucleic acids with which it is naturally associated. The polypeptide can constitute at least 10, 20, 50 70, 80 or 95% by dry weight of the purified preparation.

An "isolated nucleic acid" is a nucleic acid, the structure of which is not identical to that of any naturally occurring nucleic acid, or to that of any fragment of a naturally occurring genomic nucleic acid spanning more than three separate genes. The term therefore covers, for example: (a) a DNA which is part of a naturally occurring genomic DNA molecule but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of different (i) DNA molecules, (ii) transfected cells, or (iii) cell clones in a DNA library such as a cDNA or genomic DNA library. Isolated nucleic acid molecules according to the present invention further include molecules produced synthetically, as well as any nucleic acids that have been altered chemically and/or that have modified backbones.

Although the phrase "nucleic acid molecule" primarily refers to the physical nucleic acid molecule and the phrase "nucleic acid sequence" refers to the sequence of the nucleotides in the nucleic acid molecule, the two phrases can be used interchangeably.

The term "substantially pure" as used herein in reference to a given polypeptide means that the polypeptide is substantially free from other biological macromolecules. The substantially pure polypeptide is at least 75% (e.g., at least 80, 85, 95, or 99%) pure by dry weight. Purity can be measured by any appropriate standard method, for example, by column chromatography, polyacrylamide gel electrophoresis, or HPLC analysis.

The "percent identity" of two amino acid sequences or of two nucleic acids is determined using the algorithm of Karlin and Altschul (1990) *Proc. Natl. Acad. Sci.* USA 87:2264-2268, modified as in Karlin and Altschul (1993) *Proc. Natl. Acad. Sci.* USA 90:5873-5877. Such an algorithm is incorporated into the Blastall (BLASTP, BLASTX, TBLASTN, TBLASTX) or Bl2seq programs (version 2.x and later) of Altschul et al. (1990). *J. Mol. Biol.* 215:403-10. Bl2seq performs a comparison between the subject sequence and a target sequence using either the BLASTN (used to compare nucleic acid sequences) or BLASTP (used to compare amino acid sequences) algorithm. Typically, the default parameters of a BLOSUM62 scoring matrix, gap existence cost of 11 and extension cost of 1, a word size of 3, an expect value of 10, a per residue cost of 1 and a lambda ratio of 0.85 are used when performing amino acid sequence alignments. The output file contains aligned regions of homology between the target sequence and the subject sequence. Once aligned, a length is determined by counting the number of consecutive nucleotides or amino acid residues (i.e., excluding gaps) from the target sequence that align with sequence from the subject sequence starting with any matched position and ending with any other matched position. A matched position is any position where an identical nucleotide or amino acid residue is present in both the target and subject sequence. Gaps of one or more residues can be inserted into a target or subject sequence to maximize sequence alignments between structurally conserved domains (e.g., α-helices, β-sheets, and loops).

The percent identity over a particular length is determined by counting the number of matched positions over that particular length, dividing that number by the length and multiplying the resulting value by 100. For example, if (i) a 500 amino acid target sequence is compared to a subject amino acid sequence, (ii) the Bl2seq program presents 200 amino acids from the target sequence aligned with a region of the subject sequence where the first and last amino acids of that 200 amino acid region are matches, and (iii) the number of matches over those 200 aligned amino acids is 180, then the 500 amino acid target sequence contains a length of 200 and a sequence identity over that length of 90% (i.e., 180÷200×100=90).

It will be appreciated that a nucleic acid or amino acid target sequence that aligns with a subject sequence can result in many different lengths with each length having its own percent identity. It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

The identification of conserved regions in a template, or subject, polypeptide can facilitate homologous polypeptide sequence analysis. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the Internet at sanger.ac.uk/Pfam/ and genome.wustl.edu/Pfam/. A description of the information included in the Pfam database is described in Sonnhammer et al. (1998) *Nucl. Acids Res.* 26: 320-322; Sonnhammer et al. (1997) *Proteins* 28:405-420; and Bateman et al. (1999) *Nucl. Acids Res.* 27:260-262. From the Pfam database, consensus sequences of protein motifs and domains can be aligned with the template polypeptide sequence to determine conserved region(s).

As used herein, the term "transgene" means a nucleic acid sequence (encoding, e.g., one or more subject polypeptides), which is partly or entirely heterologous, i.e., foreign, to the transgenic plant, animal, or cell into which it is introduced, or, is homologous to an endogenous gene of the transgenic plant, animal, or cell into which it is introduced, but which is designed to be inserted, or is inserted, into the plant's genome in such a way as to alter the genome of the cell into which it is inserted (e.g., it is inserted at a location which differs from that of the natural gene or its insertion results in a knockout). A transgene can include one or more transcriptional regulatory sequences and other nucleic acid sequences, such as introns, that may be necessary for optimal expression of the selected nucleic acid, all operably linked to the selected nucleic acid, and may include an enhancer sequence.

As used herein, the term "transgenic cell" refers to a cell containing a transgene.

As used herein, a "transgenic plant" is any plant in which one or more, or all, of the cells of the plant includes a transgene. The transgene can be introduced into the cell, directly or indirectly by introduction into a precursor of the cell, by way of deliberate genetic manipulation, such as by T-DNA mediated transfer, electroporation, or protoplast transformation. The transgene may be integrated within a chromosome, or it may be extrachromosomally replicating DNA.

As used herein, the term "tissue-specific promoter" means a DNA sequence that serves as a promoter, i.e., regulates expression of a selected DNA sequence operably linked to the promoter, and which affects expression of the selected DNA sequence in specific cells of a tissue, such as a leaf, root, or stem.

As used herein, the terms "hybridizes under stringent conditions" and "hybridizes under high stringency conditions" refer to conditions for hybridization in 6× sodium chloride/sodium citrate (SSC) buffer at about 45° C., followed by two washes in 0.2×SSC buffer, 0.1% SDS at 60° C. or 65° C. As used herein, the term "hybridizes under low stringency conditions" refers to conditions for hybridization in 6×SSC buffer at about 45° C., followed by two washes in 6×SSC buffer, 0.1% (w/v) SDS at 50° C.

A "heterologous promoter", when operably linked to a nucleic acid sequence, refers to a promoter which is not naturally associated with the nucleic acid sequence.

As used herein, an agent with "anthelminthic or anthelmintic or antihelminthic activity" is an agent, which when tested, has measurable nematode-killing activity or results in infertility or sterility in the nematodes such that unviable or no offspring result. In the assay, the agent is combined with nematodes, e.g., in a well of microtiter dish having agar media or in the soil containing the agent. Staged adult nematodes are placed on the media. The time of survival, viability of offspring, and/or the movement of the nematodes are measured. An agent with "anthelminthic or anthelmintic or antihelminthic activity" reduces the survival time of adult nematodes relative to unexposed similarly staged adults, e.g., by about 20%, 40%, 60%, 80%, or more. In the alternative, an agent with "anthelminthic or anthelmintic or antihelminthic activity" may also cause the nematodes to cease replicating, regenerating, and/or producing viable progeny, e.g., by about 20%, 40%, 60%, 80%, or more.

As used herein, the term "binding" refers to the ability of a first compound and a second compound that are not covalently linked to physically interact. The apparent dissociation constant for a binding event can be 1 mM or less, for example, 10 nM, 1 nM, 0.1 nM or less.

As used herein, the term "binds specifically" refers to the ability of an antibody to discriminate between a target ligand and a non-target ligand such that the antibody binds to the target ligand and not to the non-target ligand when simultaneously exposed to both the given ligand and non-target ligand, and when the target ligand and the non-target ligand are both present in molar excess over the antibody.

As used herein, the term "altering an activity" refers to a change in level, either an increase or a decrease in the activity, (e.g., an increase or decrease in the ability of the polypeptide to bind or regulate other polypeptides or molecules) particularly a PEAMT-like or PEAMT activity. The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value, is less than 0.05.

In part, the nematode phosphoethanolamine n-methyltransferase proteins and nucleic acids described herein are novel targets for anti-nematode vaccines, pesticides, and drugs. Inhibition of these molecules can provide means of inhibiting nematode metabolism and/or the nematode lifecycle.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 depicts the cDNA sequence of *A. summ* phosphoethanolamine n-methyltransferase (PEAMT1) (SEQ ID NO: 1), its corresponding encoded amino acid sequence (SEQ ID NO: 7), and its open reading frame (SEQ ID NO: 13).

FIG. 2 depicts the cDNA sequence of *H. contortus* phosphoethanolamine n-methyltransferase (PEAMT1) (SEQ ID NO: 2), its corresponding encoded amino acid sequence (SEQ ID NO: 8), and its open reading frame (SEQ ID NO: 14).

FIG. 3 depicts the cDNA sequence of *M. incognita* phosphoethanolamine n-methyltransferase (PEAMT1) (SEQ ID NO: 3), its corresponding encoded amino acid sequence (SEQ ID NO: 9), and its open reading frame (SEQ ID NO: 15).

FIG. 4 depicts the cDNA sequence of *S. stercoralis* phosphoethanolamine n-methyltransferase (PEAMT1) (SEQ ID NO: 4), its corresponding encoded amino acid sequence (SEQ ID NO: 10), and its open reading frame (SEQ ID NO: 16).

FIG. 5 depicts the cDNA sequence of *A. summ* phosphoethanolamine n-methyltransferase (PEAMT2) (SEQ ID NO: 5), its corresponding encoded amino acid sequence (SEQ ID NO: 11), and its open reading frame (SEQ ID NO: 17).

FIG. 6 depicts the cDNA sequence of *M. javanica* phosphoethanolamine n-methyltransferase (PEAMT2) (SEQ ID NO: 6), its corresponding encoded amino acid sequence (SEQ ID NO: 12), and its open reading frame (SEQ ID NO: 18).

FIG. 7 is an alignment of the sequences of *A. summ, H. contortus, M. incognita* and *S. stercoralis* phosphoethanolamine n-methyltransferase-like polypeptides (SEQ ID NO: 7, 8, 9 and 10) and *C. elegans* PEAMT1-like polypeptides (SEQ ID NO: 19 and 20).

FIG. 8 is an alignment of the sequences of *A. summ* and *M. javanica* phosphoethanolamine n-methyltransferase-like polypeptides (SEQ ID NO: 11 and 12) and *C. elegans* PEAMT2-like polypeptide (SEQ ID NO: 21).

DETAILED DESCRIPTION

Choline (Cho) plays a number of important roles in biological systems. In bacteria, fungi, plants and animals, phosphatidylcholine is a major component of membrane phospholipids and the free base is a precursor to the neurotransmitter acetylcholine in animals. Choline is also an intermediate in glycine betaine (a compound that increases tolerance to osmotic stresses) synthesis in plants (McNeil et al. (2001) *Proc Natl Acad Sci USA* 98:10001-5). Choline is an essential nutrient in humans and other animals, and also plays a critical role in brain development in humans (Sheard et al. (1986) *Am J Clin Nutr.* 1986 43:219-24; Tayek et al. (1990) *J Am Coll Nut* 9:76-83). Most organisms can incorporate choline into phosphatidylcholine using a pathway that transfers a choline moiety from CDP-choline to diacylglycerol. In similar fashion, choline precursors such as ethanolamine (EA), monomethylethanolamine (MME) and dimethylethanolamine (DME) can also be incorporated into phospholipids via the CPD-choline or Kennedy pathway. Rhizobacteria have an additional Kennedy-independent pathway that also allows the incorporation of choline excreted from plant roots directly into phospholipids (Rudder et al. (1999) *J Biol Chem.* 274: 20011-6; Lopez-Lara & Geiger (2001) *J Biotechnol* 91:211-21).

Among those organisms that can synthesize choline, different biosynthetic pathways are used to make choline from ethanolamine via the successive addition of methyl groups using S-adenosyl methionine (SAM) as the methyl donor. These pathways differ in whether they use the free base (ethanolamine), the phosphobase (phosphoethanolamine), or the phosphatidyl base (phosphatidylethanolamine) as the methylation substrate. Plants are unusual in that they can methylate the free base, phosphobase or phosphatidylbase (phospholipid substrate) (Bolognese & McGraw (2000) *Plant Physiol.* 124(4):1800-13; Nuccio et al. (2000) *J Biol Chem* 275(19): 14095-101; Charron et al. (2002). *Plant Physiol.* 129(1):363-73). However, the conversion of phosphatidylethanolamine to phosphatidylmonomethylethanolamine has not been demonstrated in plants, so the first methylation reaction must occur at either the free base or the phosphobase level. It is now thought that in many plants the major flux occurs at the phosphobase level, catalyzed by the phosphoethanolamine N-methyltransferase enzyme (PEAMT) (i.e., pEA⇒ pMME).

In contrast, in most other organisms, methylation is carried out primarily at the phospholipid level. The complete reaction (i.e., Ptd-EA⇒Ptd-MME⇒Ptd-DME⇒PtdCho) requires a single enzyme in bacteria and mammals and two separate enzymes in fungi (Kanipes & Henry. (1997) *Biochim Biophys Acta.* 1348(1-2):134-41; Vance et al. (1997) *Biochim Biophys Acta.* 1348(1-2):142-50; Hanada et al. (2001) *Biosci Biotechnol Biochem.* 65(12):2741-8). Mammalian nerve cells are reported to have additional phopho-base methylation activity and three distinct enzymes appear to be involved (Andriamampandry et al. (1992) *Biochem J.* 288 (1):267-72; Mukherjee et al. (1995) *Neurochem Res.* 20(10):1233-7).

Plant methyltransferases from spinach and *Arabidopsis* have been cloned by complementation of choline biosynthetic mutants in fission and budding yeast, respectively (Bolognese & McGraw (2000) *Plant Physiol.* 124(4):1800-13; Nuccio et al. (2000) *J Biol Chem.* 275(19): 14095-101). In contrast to yeast methyltransferases, which act on the phosphatidylethanolamine, these plant enzymes have been shown to act on phosphoethanolamine. A similar gene has recently been cloned from chilled wheat tissues (Charron et al. (2002). *Plant Physiol.* 129(1):363-73). The plant enzymes are predicted to encode soluble proteins of approximately 55 kDa that have two domains containing separate SAM binding sites. Each domain contains motifs—termed I, post-I, II, and III—that are conserved among SAM-dependent methyltransferases. cDNA clones encompassing partial sequence from both SAM binding sites have been isolated from numerous plants, including *Oryza sativa, Brassica napus, Gossypium hirsutum*, and *Hordeum vulgare*. The plant methyltransferase structure is thought to have arisen from a gene duplication event, since prokaryotic and animal methyltransferases are approximately half the size of the plant enzymes and have only one methyltransferase domain.

Some basic kinetic characteristics of the spinach methyltransferase have been determined from enzyme preparations isolated from fission yeast overexpressing it. Enzyme activity is dependent on SAM and phosphoethanolamine concentrations. In the presence of these substrates, methyltransferase-containing extracts catalyze the formation of monomethyl- and dimethylphosphoethanolamine as well as phosphocholine. The appearance of these intermediates suggests that they are precursors to phosphocholine. A truncated version of the spinach enzyme lacking the second SAM binding site can accomplish the first methylation converting phosphoethanolamine to monomethylphosphoethanolamine, but cannot perform the second and third methylation steps. It is presumed that the C-terminal half can carry out the second and third methylation reactions.

The *C. elegans* genome contains two PEAMT-like genes and several homologs are found in other nematode EST datasets suggesting that these genes are widely distributed in *Nematoda*. The nematode proteins and plant homologs are all presumably localized in the cytosol as in the case of the wheat PEAMT as they lack secretion leaders (analyzed by methods available on the Internet at cbs.dtu.dk/services/TargetP) or transmembrane regions (analyzed by available on the Internet at cbs.dtu.dk/services/TNHMM).

One of the *C. elegans* PEAMT genes (PEAMT2) encodes a polypeptide which is 437 amino acids long (accession number AABO4824.1, wormbase locus F54D11.1) and shows significant similarity to the C-terminal half of the spinach phosphoethanolamine n-methyltransferase and other plant homologs with two SAM binding domains. The second *C. elegans* PEAMT gene appears to encode at least to two different splice variants (PEAMT1a and PEAMT1b). PEAMT1a and b are 495 and 484 amino acids long, respectively (accession number AAA81102.1, wormbase locus ZK622.3a and ZK622.3b) and are most similar to the N-terminal half of the plant PEAMTs. A PFAM analysis (available on the Internet at pfam.wustl.edu) supports the blast predictions that whereas the plant PEAMTs contain two canonical methyltransferase domains, the nematode proteins contain an N-terminal MT domain in PEAMT1 and a C-terminal MT domain in PEAMT2. PEAMT1 and PEAMT2 have 30-40% amino acid identity to their plant homologs in the regions that align. The similarity between PEAMT1 and PEAMT2 is low (22% amino acid identity) and is restricted to a small 127 amino acid region in their C-terminal domains.

Given the similarity of PEAMT1 and PEAMT2 to the N- and C-terminal domains of the plant phosphoethanolamine N-methyltransferases (e.g. spinach and *Arabidopsis*) respectively, their similar larval lethal RNAi phenotypes and the observation that the N-terminal half of the spinach enzyme is only capable of the first methylation reaction, we predicted that PEAMT1 would catalyze the conversion of pEA to pMME (the first methylation) and PEAMT2 would catalyze the conversion of pMME to pDME and pDME to pCHO. This hypothesis was confirmed by chemical complementation of the *C. elegans* PEAMT1 or PEAMT2 RNAi phenotypes with EA, MME, DME or Cho (see Table 1). As predicted, the PEAMT1 larval lethal RNAi phenotype is suppressed by MME, DME and Cho but not by EA whereas the PEAMT2 RNAi is rescued only by Cho and not by MME, DME, or EA singly or in combination.

This invention describes a novel class of nematode genes related to *C. elegans* proteins ZK622.3a (gi|28275069|gb|AAO38583.1|[28275069]), ZK622.3b (gi|15487647|gb|AAL00881.1|U39998_4[15487647]) and F54D11.1(gi|1458245|gb|AABO4824.1|[1458245]). The nematode genes can be shown by a BLAST bioinformatics analysis and phylogenetic tree building to be related to the plant phosphoethanolamine n-methyltransferase gene family. This gene family appears to be wide spread in plants and nematodes but not in arthropods, vertebrates, fungi or bacteria. We have identified additional homologs in the nematodes *A. suum, H. contortus, M. incognita, M. javanica* and *S. stercoralis*. Importantly, we have shown that these proteins are essential for the viability of *C. elegans* using RNAi, which together with the redundancy of choline synthesis in plants and absence of clear homologs in vertebrates suggests that these proteins are promising targets for anti-parasitic compounds.

The nematode proteins and plant homologs are all presumably localized in the cytosol as in the case of the wheat PEAMT as they lack secretion leaders (analyzed by methods available on the Internet at cbs.dtu.dk/services/Target P) (http://www.cbs.dtu.dk/services/TargetP/) or transmembrane regions (analyzed by available on the Internet at cbs.dtu.dk/services.TMHMM).

The present invention provides nucleic acid sequences from nematodes encoding phosphoethanolamine n-methyltransferase-like polypeptides. The *A. suum* nucleic acid molecule (SEQ ID NO: 1) and the encoded PEAMT1-like polypeptide (SEQ ID NO: 7) are depicted in FIG. 1. The *H. contortus* nucleic acid molecule (SEQ ID NO: 2) and the PEAMT1-like polypeptide (SEQ ID NO: 8) are depicted in FIG. 2. The *M. incognita* nucleic acid molecule (SEQ ID NO: 3) and the encoded PEAMT1-like polypeptide (SEQ ID NO: 9) are depicted in FIG. 3. The *S. stercoralis* nucleic acid molecule (SEQ ID NO: 4) and the PEAMT1-like polypeptide (SEQ ID NO: 10) are depicted in FIG. 4. The *A. suum* nucleic acid molecule (SEQ ID NO: 5) and the encoded PEAMT2-like polypeptide (SEQ ID NO: 11) are depicted in FIG. 5. The *M. javanica* nucleic acid molecule (SEQ ID NO: 6) and the PEAMT2-like polypeptide (SEQ ID NO: 12) are depicted in FIG. 6. Certain sequence information for the PEAMT-like genes described herein is summarized in Table 1, below.

TABLE 1

| Species | CDNA | ORF | Polypeptide | FIG. |
|---|---|---|---|---|
| A. suum | SEQ ID NO: 1 | SEQ ID NO: 7 | SEQ ID NO: 13 | FIG. 1 |
| H. contortus | SEQ ID NO: 2 | SEQ ID NO: 8 | SEQ ID NO: 14 | FIG. 2 |
| M. incognita | SEQ ID NO: 3 | SEQ ID NO: 9 | SEQ ID NO: 15 | FIG. 3 |
| S. stercoralis | SEQ ID NO: 4 | SEQ ID NO: 10 | SEQ ID NO: 16 | FIG. 4 |
| A. suum | SEQ ID NO: 5 | SEQ ID NO: 11 | SEQ ID NO: 17 | FIG. 5 |
| M. javanica | SEQ ID NO: 6 | SEQ ID NO: 12 | SEQ ID NO: 18 | FIG. 6 |

The invention is based, in part, on the discovery of PEAMT-like sequences from *A. suum, H. contortus, M. incognita, M. javanica* and *S. stercoralis*. The following examples are, therefore, to be construed as merely illustrative, and not limitative of the remainder of the disclosure in any way whatsoever. All of the publications cited herein are hereby incorporated by reference in their entirety.

EXAMPLES

A TBLASTN query with the *C. elegans* genes ZK622.3a (gi|1055130|gb|AAA81102.1|[1055130]) and F54D11.1 (gi|1458245|gb|AABO4824.1|[1458245]) identified multiple expressed sequence tags (ESTs are short nucleic acid fragment sequences from single sequencing reads) in dbest that are predicted to encode a portion of PEAMT-like enzymes in multiple nematode species.

PEAMT1-like ESTs identified as similar to *C. elegans* AAA81102.1 included *Ancylostoma caninum* (GenBank® Identification No: 15766091), *Ascaris suum* (GenBank® Identification No: 17993264), *Strongyloides stercoralis* (GenBank® Identification No: 12714760), *Haemonchus contortus* (GenBank® Identification No: 27590930), multiple from *Pristionchus pacificus* (GenBank® Identification Nos: 6067811, 15339937, 6081336, 5816211), and *Meloidogyne incognita* (GenBank®Identification No: 21652426), all from McCarter, et al. (1999) Washington University Nematode EST Project.

PEAMT2-like ESTs identified as similar to *C. elegans* AAB04824.1 included *Meloidogyne javanica* (GenBank® Identification No: 14624708); *Meloidogyne incognita* (GenBank® Identification No: 9033918); *Globodera rostochiensis* (GenBank® Identification No: 18080101); and multiple from *Ascaris suum* (GenBank® Identification Nos: 15498087, 17991691, 18688588, 17992674, 18688567, 18054078, 18828817, 18688268, 18053654, 17992401, 17991763, 17992578, 18689591, 18688755, 18688890, 18686360, 17993455, 17992123).

Full-Length Phosphoethanolamine n-Methyltransferase 1-Like cDNA Sequences

Plasmid clone, Div2728, corresponding to the *S. stercoralis* EST sequence (GenBank® Identification No: 12714760) was obtained from the Genome Sequencing Center (St. Louis, Mo.). The cDNA insert in the plasmid was sequenced in its entirety. Unless otherwise indicated, all nucleotide sequences determined herein were sequenced with an automated DNA sequencer (such as model 373 from Applied Biosystems, Inc.) using processes well-known to those skilled in the art. Primers used are listed in Table 2 (see below). Full sequence data for the *S. stercoralis* PEAMT1 was obtained from Div2728, including nucleotide sequence for codons 1-469 and additional 5' and 3' untranslated sequences.

TABLE 2

| Name | Sequence | SEQ ID NO: | Homology to |
|---|---|---|---|
| T7 | gtaatacgactcactatagggc | 22 | vector polylinker primer |
| T3 | aattaaccctcactaaaggg | 23 | vector polylinker primer |
| SP6 | gatttaggtgacactatag | 24 | vector polylinker primer |
| MTas-1 | atgcctgcggcagagcg | 25 | As PEAMT1 (codons 71-76) |
| AUAP | ggccacgcgtcgactagtac | 26 | abridged universal primer |
| SL1 | gggtttaattacccaagtttga | 27 | nematode transpliced leader |
| Oligo dT | ggccacgcgtcgactagtacttttttttttttttttt | 28 | universal primer to poly A tail |
| MU19-A | atggtgaacgttcgtcgtgc | 29 | Ce PEAMT1$_a$ (genomic) |
| MU19-B | catacgtatttctcatcatc | 30 | Ce PEAMT1$_a$ (genomic) |
| MU21-A | ccagattattaccaacgccg | 31 | Ce PEAMT2 (genomic) |
| MU21-B | tgaacttacatagattcttg | 32 | Ce PEAMT2 (genomic) |
| MTmi-9 | gcaattgaatatatgcggatg | 33 | Mi PEAMT1 (codons 192-197) |
| MTmi-8 | ctatccgaattggaatgtagcg | 34 | Mi PEAMT1 (codons 176-181) |
| MTmi-4 | cattccaattcggatagtatc | 35 | Mi PEAMT1 (codons 177-183) |

TABLE 2-continued

| Name | Sequence | SEQ ID NO: | Homology to |
|---|---|---|---|
| GeneRacer | cgactggagcacgaggacactga | 36 | GeneRacer kit component |
| GeneRacer ne | ggacactgacatggactgaaggagta | 37 | GeneRacer kit component |
| MThc-1 | caacggatttcatcgaatcg | 38 | Hc PEAMT1 (codons 79-84) |
| MThc-4 | ccacgtctttgttggttagg | 39 | Hc PEAMT1 (codons 50-55) |
| RNA oligo | cgacuggagcacgaggacacugacauggacugaagga | 40 | GeneRacer kit component |
| SL2 | ggttttaacccagtatctcaag | 41 | Haemonchus transpliced leader |
| Met12 | gcatcagcaatttgatattc | 42 | Mj PEAMT2 (codons 302-308) |
| Met28 | ccgcaatatccagaagac | 43 | As PEAMT2 (codons 159-164) |
| Met39 | cagatctcgatacattcg | 44 | As PEAMT2 (codons 67-73) |
| D2728-seqF1 | gttctgaaccatcaacaag | 45 | Ss PEAMT1 (codons 161-165) |
| D2728-seqR1 | gctgaagttaatgaacatc | 46 | Ss PEAMT1 (codons 342-346) |

Plasmid clone, Div3020, corresponding to the *A. suum* EST sequence (GenBank® Identification No: 17993264) was obtained from the Genome Sequencing Center (St. Louis, Mo.). The cDNA insert in the plasmid was sequenced in its entirety. Partial sequence data for the *A. suum* PEAMT1 was obtained from Div3020, including nucleotide sequence for codons 1-88 and additional 5' untranslated sequence. The available sequence lacked the last 372 codons of the *A. suum* PEAMT1, as well as 3' untranslated sequence.

To obtain the missing 3' sequence of the *A. suum* PEAMT1 gene, the 3' RACE technique was applied. First strand cDNA synthesis from total *A. suum* RNA was performed using an oligo dT primer (SEQ ID NO: 28). The cDNA was then directly PCR amplified using a gene specific primer (MTas-1; SEQ ID NO: 25) designed from the known sequence that anneals within the cDNA molecule of interest, and the AUAP primer, which is homologous to the 3' end of all cDNAs amplified with the oligo dT primer (SEQ ID NO: 28). This procedure was performed to generate clone Div3465, which contains codons 71-460 in addition to 3' untranslated sequences. Taken together, clones Div3020 and Div3465 contain sequences comprising the complete open reading frame of PEAMT1 gene of *A. suum*.

Plasmid clone, Div3440, corresponding to the *M. incognita* EST sequence (GenBank® Identification No: 21652426) was obtained from the Genome Sequencing Center (St. Louis, Mo.). The cDNA insert in the plasmid was sequenced in its entirety. Partial sequence data for the *M. incognita* PEAMT1 was obtained from Div3440, including nucleotide sequence for codons 14-227. The available sequence lacked the first 13 codons and the last 366 codons, as well as both the 5' and 3' untranslated sequences.

To obtain the missing 3' end of the *M. incognita* PEAMT1 gene, the 3' RACE technique was applied. First strand cDNA synthesis from total *M. incognita* RNA was performed using an oligo dT primer (SEQ ID NO: 28). The cDNA was then directly PCR amplified using a gene specific primer (MTmi-4; SEQ ID NO: 35) designed from the known sequence that anneals within the cDNA molecule of interest, and the AUAP primer, which is homologous to the 3' end of all cDNAs amplified with the oligo dT primer (SEQ ID NO: 28). This procedure was performed to generate clone Div3640, which contains codons 177-457 in addition to 3' untranslated sequences.

To obtain the missing 5' sequence of the *M. incognita* PEAMT1 gene, the 5' oligo-capped RACE method (GeneRacer™ kit from Invitrogen Life Technologies) was applied. This technique results in the selective ligation of an RNA oligonucleotide (SEQ ID NO: 40) to the 5' ends of decapped mRNA using T4 RNA ligase. First strand cDNA synthesis from total *M. incognita* oligo-capped RNA was performed using an internal gene specific primer (MTmi-9; SEQ ID NO: 33) designed from the known sequence that anneals within the cDNA molecule of interest. The first strand cDNA was then directly PCR amplified using a nested gene specific primer (MTmi-8; SEQ ID NO: 34) designed from known sequence that anneals within the cDNA molecule of interest, and the GeneRacer™ 5' nested oligo (SEQ ID NO: 37), which is homologous to the 5' end of all cDNAs amplified with the GeneRacer™ oligo-capped RNA method. This procedure was performed to generate clone Div3845, which contains codons 1-13 in addition to 5' untranslated sequences. The missing nucleotide sequence encoding codons 92-176 for the *M. incognita* PEAMT1 gene was obtained by the 5' oligo capped RACE method (GeneRacer™ kit from Invitrogen Life Technologies) as described previously. First strand cDNA synthesis from total *M. incognita* oligo-capped RNA was performed using an internal gene specific primer (MTmi-9; SEQ ID NO: 33) designed from the known sequence that anneals within the cDNA molecule of interest. The first strand cDNA was then directly PCR amplified using a nested gene specific primer (MTmi-8; SEQ ID NO: 34) designed from known sequence that anneals within the cDNA molecule of interest, and the GeneRacer™5' nested oligo (SEQ ID NO: 37), which is homologous to the 5' end of all cDNAs amplified with the GeneRacer™ oligo-capped RNA method. This procedure was performed to generate clone Div3846, which contains codons 1-181. Taken together, clones Div3440, Div3845, Div3846, and Div3640 contain sequences comprising the complete open reading frame of PEAMT1 gene of *M. incognita*.

Partial sequence data for the *H. contortus* PEAMT1 was obtained from the *H. contortus* EST (GenBank® Identification No: 27590930), including nucleotide sequence for codons 3-86. The available sequence lacked the first 2 codons and the last 374 codons of the *H. contortus* PEAMT1, as well as the 5' and 3' untranslated regions.

To obtain the 5' sequence of the *H. contortus* PEAMT1 gene, the 5' RACE technique was applied, and SL2 PCR was performed using first strand cDNA from *H. contortus* as a template (cDNA synthesis explained above). The first strand cDNA was directly PCR amplified using a gene specific primer (MThc-4; SEQ ID NO: 39) designed from known EST sequence that anneals to a site located within the cDNA of interest, and the SL2 primer (SEQ ID NO: 41), which is homologous to the 5' end of many *H. contortus* cDNAs. Amplified PCR products were then cloned into a suitable vector for DNA sequence analysis. This procedure was performed to obtain clone Div3676. This clone contains codons 1-55 in addition to 5' untranslated sequences. To obtain the 3' sequence of the *H. contortus* PEAMT1 gene, the 3' RACE technique was applied. First strand cDNA synthesis from *H. contortus* RNA was performed as described previously. The first strand cDNA was directly PCR amplified using a gene specific primer (MThc-1; SEQ ID NO: 38) designed from the known sequence that anneals within the first strand cDNA molecule of interest, and the AUAP primer (SEQ ID NO: 26), which is homologous to the 3' end of the cDNA molecule of interest. This procedure was performed to generate clone Div3650, which contains codons 79-460 in addition to 3' untranslated sequences. Taken together, clones Div3650, Div3676, and the known EST sequence contain sequences comprising the complete open reading frame of the PEAMT1 gene of *H. contortus*.

Full-Length Phosphoethanolamine n-Methyltransferase2-Like cDNA Sequences

Plasmid clone, Div2562, corresponding to the *M. javanica* EST sequence (GenBank® Identification No: 14624708) was obtained from the Genome Sequencing Center (St. Louis, Mo.). The cDNA insert in the plasmid was sequenced in its entirety. Unless otherwise indicated, all nucleotide sequences determined herein were sequenced with an automated DNA sequencer (such as model 373 from Applied Biosystems, Inc.) using processes well-known to those skilled in the art. Primers used for sequencing are listed in Table 2 (see below). Partial sequence data for the *M. javanica* PEAMT2 was obtained from Div2562, including nucleotide sequence for codons 285-472 and additional 3' untranslated sequence. The clone lacked the first 284 codons of the *M. javanica* PEAMT2, as well as the 5' untranslated region.

To obtain the missing 5' sequence of the *M. javanica* PEAMT2 gene, the 5' RACE technique was applied, and SL1 PCR was performed using first strand cDNA from *M. javanica* as a template. Briefly, SL1 PCR utilizes the observation, that unlike most eukaryotic mRNAs, many nematode mRNA molecules contain a common leader sequence (5' gggtttaattacccaagtttga 3') (SEQ ID NO: 27) transpliced to their 5' ends. If this sequence is present on the 5' end of the cDNA, that cDNA can be amplified using PCR with a primer that binds to the SL1 transpliced leader and a gene-specific primer near the 3' end of the cDNA.

Briefly, following the instructions provided by Life Technologies cDNA synthesis kit, first strand cDNA synthesis was performed on total nematode RNA using SuperScript™ II Reverse Transcriptase and an oligo-dT primer (which anneals to the natural poly A tail found on the 3' end of all eukaryotic mRNA). RNase H was then used to degrade the original mRNA template. Following degradation of the original mRNA template, the first strand cDNA was directly PCR amplified without further purification using Taq DNA polymerase, a gene specific primer (Met12, SEQ ID NO: 42) designed from known sequence to the cDNA of interest, and the SL1 primer (SEQ ID NO: 27), which is homologous to the 5' end of many nematode cDNAs. Amplified PCR products were then cloned into a suitable vector for DNA sequence analysis. This procedure was performed to obtain clone Div2474. Div2474 contains codons 1-308 in addition to 5' untranslated sequences. Taken together, clones Div2562 and Div2474 contain sequences comprising the complete open reading frame of the PEAMT2 gene from *M. javanica*.

Partial sequence data for the *A. suum* PEAMT2 was obtained from the *A. suum* EST (GenBank® Identification No: 15498087), including nucleotide sequence for codons 35-205. The available sequence lacked the first 34 codons and the last 232 codons of the *A. suum* PEAMT2, as well as the 5' and 3' untranslated regions.

To obtain the 5' sequence of the *A. suum* PEAMT2 gene, the 5' RACE technique was applied, and SL1 PCR was performed using first strand cDNA from *A. suum* as a template (cDNA synthesis explained above). The first strand cDNA was directly PCR amplified using a gene specific primer (Met28; SEQ ID NO: 43) designed from the known EST sequence that anneals to a site located within the cDNA of interest, and the SL1 primer (SEQ ID NO: 27), which is homologous to the 5' end of many nematode cDNAs. Amplified PCR products were then cloned into a suitable vector for DNA sequence analysis. This procedure was performed to obtain clone Div2715. This clone contained codons 1-164 in addition to 5' untranslated sequences. To obtain the 3' sequence of the *A. suum* PEAMT2 gene, the 3' RACE technique was applied. First strand cDNA synthesis from *A. suum* RNA was performed as described previously. The first strand cDNA was directly PCR amplified using a gene specific primer (Met39; SEQ ID NO: 44) designed from the known sequence that anneals within the first strand cDNA molecule of interest, and the AUAP primer (SEQ ID NO: 26), which is homologous to the 3' end of the cDNA of interest. This procedure was performed to generate clone Div2877, which contains codons 67-437 in addition to 3' untranslated sequences. Taken together, clones Div2715 and Div2877 contain sequences comprising the complete open reading frame of PEAMT2 gene of *A. suum*.

Characterization of Six Nematode Phosphoethanolamine n-Methyltransferases

The sequences of the four PEAMT1-like phosphoethanolamine n-methyltransferase-like nucleic acid molecules (*A. suum, H. contortus, M. incognita* and *S. stercoralis*) and two PEAMT2-like phosphoethanolamine n-methyltransferase-like nucleic acid molecules (*A. suum* and *M. javanica*) are depicted in FIG. 1, FIG. 2, FIG. 3, FIG. 4, FIG. 5 and FIG. 6 as SEQ ID NO: 1, SEQ ID NO: 2, SEQ ID NO: 3, SEQ ID NO: 4, SEQ ID NO: 5 and SEQ ID NO: 6. SEQ ID NO: 13 (*A. suum*) contains an open reading frame encoding a 460 amino acid polypeptide, SEQ ID NO: 14 (*H. contortus*) contains an open reading frame encoding a 460 amino acid polypeptide, SEQ ID NO: 15 (*M. incognita*) contains an open reading frame encoding a 457 amino acid polypeptide, SEQ ID NO: 16 (*S. stercoralis*) contains an open reading frame encoding a 469 amino acid polypeptide, SEQ ID NO: 17 (*A. suum*) contains an open reading frame encoding a 437 amino acid polypeptide and SEQ ID NO: 18 (*M. javanica*) contains an open reading frame encoding a 472 amino acid polypeptide.

The sequence of the *A. suum* PEAMT1-like nucleic acid molecule is recited in FIG. 1 as SEQ ID NO: 1. This nucleotide sequence contains an open reading frame encoding a 460 amino acid polypeptide. The *A. suum* PEAMT1-like-protein (depicted in FIG. 1 as SEQ ID NO 7) is approximately 52% identical (in the region of shared homology) to the *C. elegans* PEAMT1-like proteins (depicted in FIG. 7 as SEQ ID NO: 19 and 20). The similarity between the PEAMT1 proteins from *A. suum* and from *C. elegans* is presented as a multiple alignment generated by the Clustal X multiple alignment program.

The sequence of the *H. contortus* PEAMT1-like nucleic acid molecule is recited in FIG. 2 as SEQ ID NO: 2. This nucleotide sequence contains an open reading frame encoding a 460 amino acid polypeptide. The *H. contortus* PEAMT1-like protein (depicted in FIG. 2 as SEQ ID NO 8) is approximately 63% identical (in the region of shared homology) to the *C. elegans* PEAMT1-like proteins (depicted in FIG. 7 as SEQ ID NO: 19 and 20). The similarity between the PEAMT1 proteins from *H. contortus* and from *C. elegans* is presented as a multiple alignment generated by the Clustal X multiple alignment program.

The sequence of the *M. incognita* PEAMT1-like nucleic acid molecule is recited in FIG. 3 as SEQ ID NO: 3. This nucleotide sequence contains an open reading frame encoding a 457 amino acid polypeptide. The *M. incognita* PEAMT1-like protein (depicted in FIG. 3 as SEQ ID NO 9) is approximately 43% identical (in the region of shared homology) to the *C. elegans* PEAMT1-like proteins (depicted in FIG. 7 as SEQ ID NO: 19 and 20). The similarity between the PEAMT1 proteins from *M. incognita* and from *C. elegans* is presented as a multiple alignment generated by the Clustal X multiple alignment program.

The sequence of the *S. stercoralis* PEAMT1-like nucleic acid molecule is recited in FIG. 4 as SEQ ID NO: 4. This nucleotide sequence contains an open reading frame encoding a 469 amino acid polypeptide. The *S. stercoralis* PEAMT1-like protein (depicted in FIG. 4 as SEQ ID NO: 10) is approximately 36% identical (in the region of shared homology) to the *C. elegans* PEAMT1-like proteins (depicted in FIG. 7 as SEQ ID NO: 19 and 20). The similarity between the PEAMT1 proteins from *S. stercoralis* and from *C. elegans* is presented as a multiple alignment generated by the ClustaIX multiple alignment program.

The sequence of the *A. suum* PEAMT2-like nucleic acid molecule is recited in FIG. 5 as SEQ ID NO: 5. This nucleotide sequence contains an open reading frame encoding a 437 amino acid polypeptide. The *A. suum* PEAMT2-like protein (depicted in FIG. 5 as SEQ ID NO 11) is approximately 48% identical (in the region of shared homology) to the *C. elegans* PEAMT2-like proteins (depicted in FIG. 8 as SEQ ID NO: 21). The similarity between the PEAMT2 proteins from *A. suum* and from *C. elegans* is presented as a multiple alignment generated by the Clustal X multiple alignment program.

The sequence of the *M. javanica* PEAMT2-like nucleic acid molecule is recited in FIG. 6 as SEQ ID NO: 6. This nucleotide sequence contains an open reading frame encoding a 472 amino acid polypeptide. The *M. javanica* PEAMT2-likeprotein (depicted in FIG. 6 as SEQ ID NO 12) is approximately 50% identical (in the region of shared homology) to the *C. elegans* PEAMT2-like proteins (depicted in FIG. 8 as SEQ ID NO: 21). The similarity between the PEAMT2 proteins from *M. javanica* and from *C. elegans* is presented as a multiple alignment generated by the Clustal X multiple alignment program.

The similarity among the *A. suum, H. contortus, M. incognita, S. stercoralis,* and *C. elegans* PEAMT1-like polypeptides is presented as a multiple alignment generated by the Clustal X multiple alignment program (depicted in FIG. 7). The similarity among the *A. suum, M. javanica* and *C. elegans* PEAMT2-like polypeptides is presented as multiple alignment generated by the Clustal X multiple alignment program (depicted in FIG. 8)

S-adenosylmethionine (SAM)-dependent methyltransferase proteins contain four conserved motifs which define the SAM-binding site (Kagan & Clarke (1994) *Arch Biochem Biophys.* 310:417-427). The four domains are referred to as motif I, post I, motif II, and motif III. The four domains are present in all of the PEAMT1-like proteins shown in FIG. 7 and all of the PEAMT2-like proteins shown in FIG. 8. Their predicted amino acid positions in the PEAMT1-like and PEAMT2-like proteins are listed in Tables 3 and 4 respectively.

TABLE 3

Amino Acid positions of conserved SAM-binding motifs in Nematode PEAMT1-like proteins

| Nematode | Motif I | Post I | Motif II | Motif III |
|---|---|---|---|---|
| *A. suum* | 56-63 | 76-80 | 114-120 | 143-152 |
| *H. contortus* | 56-63 | 76-80 | 114-120 | 143-152 |
| *M. incognita* | 64-71 | 84-88 | 122-128 | 151-160 |
| *S. stercoralis* | 56-63 | 76-80 | 118-124 | 147-156 |
| *C. elegans$_a$* | 70-77 | 90-94 | 128-134 | 157-166 |
| *C. elegans$_b$* | 79-86 | 99-103 | 137-143 | 166-175 |

TABLE 4

Amino Acid positions of conserved SAM-binding motifs in Nematode PEAMT2-like proteins

| Nematode | Motif I | Post I | Motif II | Motif III |
|---|---|---|---|---|
| *A. suum* | 230-238 | 252-256 | 292-298 | 319-328 |
| *M. javanica* | 254-262 | 276-280 | 316-322 | 343-352 |
| *C. elegans* | 228-236 | 250-254 | 290-296 | 317-326 |

The similarity between *A. suum, H. contortus, M. incognita, M. javanica* and *S. stercoralis* PEAMT-like sequences and other sequences were also investigated by comparison to sequence databases using BLASTP analysis against nr (a non-redundant protein sequence database available at www.ncbi.nlm.nih.gov) and TBLASTN analysis against dbest (an EST sequence database available at www.ncbi.nlm.nih.gov; top 500 hits; E=1e−4). The "Expect (E) value" is the number of sequences that are predicted to align by chance to the query sequence with a score S or greater given the size of the database queried. This analysis was used to determine the potential number of plant and vertebrate homologs for each of the nematode PEAMT-like polypeptides described above. *A. suum* (SEQ ID NO: 1 and 5), *H. contortus* (SEQ ID NO:2), *M. incognita* (SEQ ID NO:3), *M. javanica* (SEQ ID NO: 6), *S. stercoralis* (SEQ ID NO:4) and *C. elegans* (SEQ ID NO:19, 20 and 21) PEAMT-like sequences had no high scoring vertebrate hits in nr or dbest having sufficient sequence similarity to meet the threshold E value of 1e−4 (this E value approximately corresponds to a threshold for removing sequences having a sequence identity of less than about 25% over approximately 100 amino acids). Accordingly, the *A. suum, H. contortus, M. incognita, M. javanica* and *S. stercoralis* PEAMT-like enzymes of this invention do not appear to share significant sequence similarity with common vertebrate methyltransferase enzymes such as the *Homo sapiens* (gi|13345056|gb|AAK19172.1|[13345056]) or the *Rattus norvegicus* (gi|310195|gb|AAA03154.1|[310195]) phosphatidylethanolamine n-methyltransferase.

On the basis of the lack of similarity to vertebrate methyltransferases and the redundancy of choline biosynthesis in plants, the *A. suum, H. contortus, M. incognita, M. javanica* and *S. stercoralis* PEAMT-like enzymes are useful targets of inhibitory compounds selective for some nematodes over their hosts (e.g., humans, animals, and plants).

Functional predictions were made using BLAST with the default parameters on the nr database. BLAST searches and multiple alignment construction with CLUSTALX demonstrated that the *C. elegans* genes ZK622.3a and F54D11.1 share strong homology with the plant PEAMT genes and are therefore related to the plant PEAMT family. Reciprocal blast searches and phylogenetic trees confirm that the nucleotide sequences from *A. suum, H. contortus, M. incognita, M. javanica* and *S. stercoralis* are orthologs of the *C. elegans* gene and are therefore likely PEAMT proteins. Protein localizations were predicted using TargetP and transmembrane domains with TMHMM. The *A. suum, H. contortus, M. incognita, M. javanica* and *S. stercoralis* PEAMT polypeptides (SEQ ID NO: 7, 8, 9, 10, 11 and 12, respectively) are likely localized in the cytoplasm as in the case of the wheat PEAMT homolog, as they lack secretion or strong mitochondrial localization predictions and have no predicted transmembrane regions.

RNA Mediated Interference (RNAi)

A double stranded RNA (dsRNA) molecule can be used to inactivate a phosphoethanolamine N-methyl transferase (PEAMT) gene in a cell by a process known as RNA mediated-interference (Fire et al. (1998) *Nature* 391:806-811, and Gonczy et al. (2000) *Nature* 408:331-336). The dsRNA molecule can have the nucleotide sequence of a PEAMT nucleic acid (preferably exonic) or a fragment thereof. For example, the molecule can comprise at least 50, at least 100, at least 200, at least 300, or at least 500 or more contiguous nucleotides of a PEAMT-like gene. The dsRNA molecule can be delivered to nematodes via direct injection, by soaking nematodes in aqueous solution containing concentrated dsRNA, or by raising bacteriovorous nematodes on *E. coli* genetically engineered to produce the dsRNA molecule (Kamath et al. (2000) *Genome Biol.* 2; Tabara et al. (1998) *Science* 282:430-431).

PEAMT RNAi by Feeding:

*C. elegans* can be grown on lawns of *E. coli* genetically engineered to produce double-stranded RNA (dsRNA) designed to inhibit PEAMT1 or PEAMT2 expression. Briefly, *E. coli* were transformed with genomic fragments encoding portions of the *C. elegans* PEAMT1 or the PEAMT2 gene. Specifically, a 960 nucleotide fragment was amplified from the PEAMT1 gene using oligo-nucleotide primers containing the sequences 5'-ATGGTGAACGT-TCGTCGTGC-3' SEQ ID NO:29 and 5'-CATACG-TATTTCTCATCATC-3' SEQ ID NO:30 respectively, or an 854 nucleotide fragment was amplified from the PEAMT2 gene using oligo-nucleotide primers containing the sequences 5'-CCAGATTATTACCAACGCCG-3' SEQ ID NO:31 and 5'-TGAACTTACATAGATTCTTG-3' SEQ ID NO:32 respectively. The PEAMT1 and PEAMT2 genomic fragments were cloned separately into an *E. coli* expression vector between opposing T7 polymerase promoters. The clone was then transformed into a strain of *E. coli* that carries an IPTG-inducible T7 polymerase. As a control, *E. coli* was transformed with a gene encoding the Green Fluorescent Protein (GFP). Feeding RNAi was initiated from *C. elegans* larvae at 23° C. on NGM plates containing IPTG and *E. coli* expressing the *C. elegans* PEAMT1 or PEAMT2, or GFP dsRNA. If the starting worm (the P0) was an L1, or a dauer larva, the phenotype of both the PEAMT1 and PEAMT2 RNAi-generated mutants was complete or almost complete sterility. One the other hand, if the P0 animal was an L4 larva, then the phenotype of both the PEAMT1 and PEAMT2 RNAi-generated mutants was L1/L2 larval arrested development and lethality. The sequence of the PEAMT1 and PEAMT2 genes is of sufficiently high complexity (i.e., unique) such that the RNAi is not likely to represent cross reactivity with other genes.

*C. elegans* cultures grown in the presence of *E. coli* expressing dsRNA from the PEAMT1 or the PEAMT2 gene were strongly impaired indicating that the PEAMT genes provide essential functions in nematodes and that dsRNA from the PEAMT-like genes is lethal when ingested by *C. elegans*. These results demonstrate that PEAMT's are important for the viability of *C. elegans* and suggest that they are useful targets for the development of compounds that reduce the viability of nematodes.

Chemical Rescue of the PEAMT1 and PEAMT2 RNAi-Generated Phenotype.

The experiments described below were designed to test whether the PEAMT1/PEAMT2 RNAi knockout phenotype can be rescued by providing *C. elegans* with the products downstream of the predicted PEAMT reaction catalyzed by the enzymes. The free bases (EA, MME, DME and Cho) were added to the bacterial medium and it was assumed that these would be taken up and converted to the corresponding phosphobases by the actions of ethanolamine/choline kinases.

*C. elegans* worms were fed bacteria expressing dsRNA homologous to PEAMT1, PEAMT2, actin, or GFP along with specific chemicals (EA, MME, DME or Cho). Chemicals were added to NGM plates at various concentrations and negative (GFP dsRNA) and positive (actin dsRNA) controls were performed for each chemical or chemical mixture at each concentration. Specifically, agar plates containing NGM and the chemicals specified in Table 1 (see below) were seeded with bacteria expressing double-stranded RNA homologous to either PEAMT1 or PEAMT2. In some experiments a single L1 or dauer larva was placed on each plate, and the P0 and the F1 were examined for the next 5 days. In other experiments, a single L4 *C. elegans* hermaphrodite was placed on each plate. The hermaphrodite was allowed to lay eggs for 24 hours and the phenotype of the F1 progeny was scored 48 hours after the initial 24-hour egg-laying period. At the time of scoring, 4 individual F1 progeny were cloned to separate plates containing the same chemical and bacteria they were grown on. The F1 and F2 progeny were examined over the next 4-5 days for the presence of a phenotype.

TABLE 5

C. elegans PEAMT1 and PEAMT2 RNAi feeding phenotypes
(starting with *C. elegans* L1, dauer, or L4 larva as the P0 animal).

| | Compounds added to the plate | F1 phenotype | |
|---|---|---|---|
| P0 | media | PEAMT1 dsRNA | PEAMT2 dsRNA |
| L1 | None | Sterility | Sterility |
| | 10 mM DME | Fertile adults | Sterility |
| Dauer | None | Partial sterility | Partial sterility |
| | 10 mM DME | Fertile adults | Sterility |
| L4 | None | L1/L2 arrest/lethality | L1/L2 arrest/lethality |
| | 10 mM ethanolamine (EA) | L1/L2 arrest/lethality | L1/L2 arrest/lethality |
| | 5 or 10 mM MME | Fertile adults | L1/L2 arrest/lethality |

TABLE 5-continued

C. elegans PEAMT1 and PEAMT2 RNAi feeding phenotypes
(starting with C. elegans L1, dauer, or L4 larva as the P0 animal).

| | Compounds added to the plate | F1 phenotype | |
|---|---|---|---|
| P0 | media | PEAMT1 dsRNA | PEAMT2 dsRNA |
| | 5 or 10 mM DME | Fertile adults | L1/L2 arrest/lethality |
| | 5 mM choline (Cho) | L1/L2 arrest/lethality | L1/L2 arrest/lethality |
| | 10 or 15 mM Cho | Sterile adults | L1/L2 arrest/lethality |
| | 25 mM or 30 mM Cho | Fertile adults | Fertile adults |
| | 5 mM each EA, MME | Fertile adults | L1/L2 arrest/lethality |
| | 5 mM each EA, DME | | |
| | 5 mM each EA, Cho | | |
| | 5 mM each MME, DME | | |
| | 5 mM each MME, Cho | | |
| | 5 mM each DME, Cho | | |
| | 5 mM each MME, DME, Cho | | |

The *C. elegans* phosphoethanolamine N-methyltransferase proteins PEAMT1 and PEAMT2 together catalyze the conversion of phosphoethanolamine to phosphocholine. The RNAi-generated mutants of PEAMT1 or PEAMT2 are both predicted to have decreased levels of choline which leads to sterility, or L1/L2 larval arrested development and death. Addition of 25 mM choline rescues the larval arrest associated with both PEAMT1 and PEAMT2 RNAi phenotypes. However, only the PEAMT1 mutants are rescued by the addition of 5 mM monomethylethanolamine (MME) or 5 mM dimethylethanolamine (DME) while the PEAMT2 mutants are not (see Table 5). These data are consistent with the prediction that PEAMT1 catalyzes the first methylation while PEAMT2 catalyzes the second and third methylations in the conversion of pEA to pCho:

Five mM DME rescues the sterility associated with PEAMT1 RNAi. The rescue by DME strongly suggests the sterility is due to a reduction in choline production and not due to other changes caused by the PEAMT mutations.

The data also demonstrate that when choline alone is used as the rescuing chemical, 25 mM choline is required to complement the PEAMT1 and PEAMT2 RNAi phenotypes. This suggests that chemicals that interfere with this pathway will not likely be counteracted by the amount of choline nematodes can acquire from the environment.

Nematicidal Activity of Small Molecules Structurally Similar to Ethanolamine against *Caenorhabditis elegans*

The structures of ethanolamine-like molecules tested against *C. elegans* for nematicidal activity are shown below.

TABLE 6

| COMPOUND | STRUCTURE |
|---|---|
| 2-(diisopropylamino)ethanol (N-substituted) | $\begin{array}{c} CH_3 \\ | \\ CH_3CH \\ \phantom{CH_3}\diagdown \\ \phantom{CH_3CH}N-CH_2CH_2OH \\ \phantom{CH_3}\diagup \\ CH_3CH \\ | \\ CH_3 \end{array}$ |

TABLE 6-continued

| COMPOUND | STRUCTURE |
|---|---|
| 2-(tert-butylamino)ethanol (N-substituted) | $CH_3-\underset{\underset{CH_3}{|}}{\overset{\overset{CH_3}{|}}{C}}-NHCH_2CH_2OH$ |
| D-phenylalaninol (C2-substituted) | $H_2N\diagdown\phantom{H}H$ <br> $CH_2\overset{\cdot}{C}CH_2OH$ <br> (phenyl ring) |
| 2-amino-1-phenylethanol (C1-substituted) | $H_2NCH_2CHOH$ <br> (phenyl ring) |
| N-(2-hydroxyethyl)aniline (N-substituted) | $NHCH_2CH_2OH$ <br> (phenyl ring) |

One approach to the development of chemicals that interfere with the function of an enzyme is to identify compounds that mimic substrate binding but that cannot be acted on by the enzyme. Therefore, several ethanolamine-derived compounds were tested for the ability to kill *C. elegans* in culture. Compounds with substitutions at various positions on ethanolamine were tested including some with substitutions on the nitrogen, the carbon adjacent to the nitrogen (C2), and on the carbon adjacent to the oxygen (C1).

A single *C. elegans* L4 larva (the P0 animal) was placed on a lawn of *E. coli* that had been spotted onto NGM plates containing various concentrations of the ethanolamine-like compounds. The growth and development of the P0 and its F1 progeny at 23° C. was monitored by visual observation over several days. Four of the compounds tested [2-(diisopropylamino)ethanol, 2-(tert-butylamino)ethanol, D-phenylalaminol and N-(2-hydroxyethyl)aniline], showed nematicidal activity against *C. elegans*. In addition, the phenotype of worms treated with the nematicidal ethanolamine-like compounds mimicked the RNAi-phenotype of PEAMT1 and PEAMT2. That is, the F1 progeny of the treated worm did not develop beyond the L1/L2 stage and died. Treatment of *C. elegans* with the C1-substituted compound 2-amino-1-phenylethanol showed no nematicidal effect.

TABLE 7

Nematicidal activity of ethanolamine-like compounds against *C. elegans*.

| COMPOUND | CONCENTRATION | F1 PHENOTYPE |
| --- | --- | --- |
| 2-(diisopropylamino)ethanol | 10 mM | L1/L2 arrest/lethality |
| 2-(tert-butylamino)ethanol | 10 mM | L1/L2 arrest/lethality |
| D-phenylalaninol | 10 mM | L1/L2 arrest/lethality |
| 2-amino-1-phenylethanol | 25 mM | Wild-type development |
| N-(2-hydroxyethyl)aniline | 10 mM | L1/L2 arrest/lethality |
| Control (no compound) | Not applicable | Wild-type development |

Nematicidal Activity of Ethanolamine-Like Compounds against Plant Parasites.

The ethanolamine-like compounds mentioned above are also nematicidal against the plant parasites *Meloidogyne incongnita* and *Meloidogyne javanica*. Between 25 and 50 J2 stage larvae were soaked in the compounds for 48 hours at the indicated concentrations. After the treatment, the larvae were moved to an agar plate containing NGM. Worms that crawl away from the application spot are scored as alive while those that remain at the application spot are scored as dead. The three compounds that were nematicidal against *C. elegans* were also nematicidal against *M. incognita* and *M. javanica*

TABLE 8

| COMPOUND | SPECIES | CONCENTRATION | % DEAD WORMS |
| --- | --- | --- | --- |
| di-isopropylethanolamine | *M. incognita* | 2.5 mM | 75 |
| | *M. javanica* | 2.5 mM | 70 |
| 2-(tert-butylamino)ethanol | *M. incognita* | 5 mM | 50 |
| | *M. javanica* | 15 mM | 50 |
| D-phenylalaninol | *M. incognita* | 25 mM | 100 |
| Control (no compound) | *M. incognita* | not applicable | 15 |

Nematicidal Activity of Ethanolamine-Like Compounds against Other Nematodes.

The ethanolamine-like compounds mentioned above are also nematicidal against *Acrobiloides ellesmerensis* and *Cephalobus* sp. Assays were done as those described for *C. elegans* L4 larvae. Three of the four compounds that were nematicidal against *C. elegans* were tested and were found to be nematicidal against *A. ellesmerensis* and *Cephalobus* sp.

TABLE 9

| COMPOUND | SPECIES | CONCENTRATION | F1 PHENOTYPE |
| --- | --- | --- | --- |
| diisopropylamino)ethanol | *A. ellesmerensis* | 10 mM | L1/L2 arrest/lethality |
| | *Cephalobus* sp. | 10 mM | L1/L2 arrest/lethality |
| 2-(tert-butylamino)ethanol | *A. ellesmerensis* | 10 mM | L1/L2 arrest/lethality |
| | *Cephalobus* sp. | 10 mM | L1/L2 arrest/lethality |
| D-phenylalaninol | *A. ellesmerensis* | 12.5 mM | L1/L2 arrest/lethality |
| | *Cephalobus* sp. | 12.5 mM | L1/L2 arrest/lethality |
| Control (no compound) | *Cephalobus* sp. | not applicable | Wild-type |

Sulfonic, phosphonic, or phosphate prodrugs based on the structures of the molecules discussed here will provide better activity than the parent molecules themselves. Enzymes like PEAMT1 and PEAMT2, which interact with phosphorylated substrates, bind more tightly to the phosphorylated forms of the substrate than to the non-phosphorylated forms. For example, in the case of SH2 domains, phosphorylated peptides exhibit binding four orders of magnitude greater than non-phosphorylated peptides (Bradshaw et al, (1999) *J. Mol. Biol.* 293(4):971-85). Therefore, the addition of a phosphate, or a phosphate mimic (e.g., phosphonate, sulfonate) to the ethanolamine-like compounds will increase the affinity for the enzyme making them more potent inhibitors of the PEAMT enzymes.

Identification of Additional Phosphoethanolamine n-Methyltransferase-Like Sequences A skilled artisan can utilize the methods provided in the example above to identify additional nematode phosphoethanolamine n-methyltransferase-like sequences, e.g., PEAMT-like sequence from nematodes other than *A. suum, H. contortus, M. incognita, M. javanica* and *S. stercoralis* and/or *C. elegans*. In addition, nematode PEAMT-like sequences can be identified by a variety of methods including computer-based database searches, hybridization-based methods, and functional complementation.

Database Identification. A nematode phosphoethanolamine n-methyltransferase-like sequence can be identified from a sequence database, e.g., a protein or nucleic acid database using a sequence disclosed herein as a query. Sequence comparison programs can be used to compare and analyze the nucleotide or amino acid sequences. One such software package is the BLAST suite of programs from the National Center for Biotechnology Institute (NCBI; Altschul et al. (1997) *Nucl. Acids Research* 25:3389-3402). A phosphoethanolamine n-methyltransferase-like sequence of the invention can be used to query a sequence database, such as nr, dbest (expressed sequence tag (EST) sequences), and htgs (high-throughput genome sequences), using a computer-based search, e.g., FASTA, BLAST, or PSI-BLAST search. Homologous sequences in other species (e.g., plants and animals) can be detected in a PSI-BLAST search of a database such as nr (E value=10, H value=1e-2, using, for example, four iterations; available at www.ncbi.nlm.nih.gov). Sequences so obtained can be used to construct a multiple alignment, e.g., a ClustalX alignment, and/or to build a phylogenetic tree, e.g., in ClustalX using the Neighbor-Joining method (Saitou et al. (1987) *Mol. Biol. Evol.* 4:406-425) and bootstrapping (1000 replicates; Felsenstein (1985) *Evolution* 39:783-791). Distances may be corrected for the occurrence of multiple substitutions $[D_{corr}=-\ln(1-D-D^2/5)$ where D is the fraction of amino acid differences between two sequences] (Kimura (1983) *The Neutral Theory of Molecular Evolution*, Cambridge University Press).

The aforementioned search strategy can be used to identify phosphoethanolamine n-methyltransferase-like sequences in nematodes of the following non-limiting, exemplary genera: Plant-parasitic nematode genera: *Afrina, Anguina, Aphelenchoides, Belonolaimus, Bursaphelenchus, Cacopaurus, Cactodera, Criconema, Criconemoides, Cryphodera, Ditylen-* chus, Dolichodorus, Dorylaimus, Globodera, Helicotylenchus, Hemicriconemoides, Hemicycliophora, Heterodera, Hirschmanniella, Hoplolaimus, Hypsoperine, Longidorus, Meloidogyne, Mesoanguina, Nacobbus, Nacobbodera, Panagrellus, Paratrichodorus, Paratylenchus, Pratylenchus, Pterotylenchus, Punctodera, Radopholus, Rhadinaphelenchus, Rotylenchulus, Rotylenchus, Scutellonema, Subanguina, Thecavermiculatus, Trichodorus, Turbatrix, Tylenchorhynchus, Tylenchulus, Xiphinema.

Animal- and human-parasitic nematode genera: Acanthocheilonema, Aelurostrongylus, Ancylostoma, Angiostrongylus, Anisakis, Ascaris, Ascarops, Bunostomum, Brugia, Capillaria, Chabertia, Cooperia, Crenosoma, Cyathostome species (Small Strongyles), Dictyocaulus, Dioctophyma, Dipetalonema, Dirofilaria, Dracunculus, Draschia, Elaneophora, Enterobius, Filaroides, Gnathostoma, Gonylonema, Habronema, Haemonchus, Hyostrongylus, Lagochilascaris, Litomosoides, Loa, Mammomonogamus, Mansonella, Muellerius, Metastrongylid, Necator, Nematodirus, Nippostrongylus, Oesophagostomum, Ollulanus, Onchocerca, Ostertagia, Oxyspirura, Oxyuris, Parafilaria, Parascaris, Parastrongyloides, Parelaphostrongylus, Physaloptera, Physocephalus, Protostrongylus, Pseudoterranova, Setaria, Spirocerca, Stephanurus, Stephanofilaria, Strongyloides, Strongylus, Spirocerca, Syngamus, Teladorsagia, Thelazia, Toxascaris, Toxocara, Trichinella, Trichostrongylus, Trichuris, Uncinaria, and Wuchereria.

Particularly preferred nematode genera include: Plant: Anguina, Aphelenchoides, Belonolaimus, Bursaphelenchus, Ditylenchus, Dolichodorus, Globodera, Heterodera, Hoplolaimus, Longidorus, Meloidogyne, Nacobbus, Pratylenchus, Radopholus, Rotylenchus, Tylenchulus, Xiphinema.

Animal and human parasites: Ancylostoma, Ascaris, Brugia, Capillaria, Cooperia, Cyathostome species, Dictyocaulus, Dirofilaria, Dracunculus, Enterobius, Haemonchus, Necator, Nematodirus, Oesophagostomum, Onchocerca, Ostertagia, Oxyspirura, Oxyuris, Parascaris, Strongyloides, Strongylus, Syngamus, Teladorsagia, Thelazia, Toxocara, Trichinella, Trichostrongylus, Trichuris, and Wuchereria.

Particularly preferred nematode species include: Plant parasites: Anguina tritici, Aphelenchoides fragariae, Belonolaimus longicaudatus, Bursaphelenchus xylophilus, Ditylenchus destructor, Ditylenchus dipsaci Dolichodorus heterocephalous, Globodera pallida, Globodera rostochiensis, Globodera tabacum, Heterodera avenae, Heterodera cardiolata, Heterodera carotae, Heterodera cruciferae, Heterodera glycines, Heterodera major, Heterodera schachtii, Heterodera zeae, Hoplolaimus tylenchiformis, Longidorus sylphus, Meloidogyne acrnea, Meloidogyne arenaria, Meloidogyne chitwoodi, Meloidogyne exigua, Meloidogyne graminicola, Meloidogyne hapla, Meloidogyne incognita, Meloidogyne javanica, Meloidogyne nassi, Nacobbus batatiformis, Pratylenchus brachyurus, Pratylenchus coffeae, Pratylenchus penetrans, Pratylenchus scribneri, Pratylenchus zeae, Radopholus similis, Rotylenchus reniformis, Tylenchulus semipenetrans, Xiphinema americanum.

Animal and human parasites: Ancylostoma braziliense, Ancylostoma caninum, Ancylostoma ceylanicum, Ancylostoma duodenale, Ancylostoma tubaeforme, Ascaris suum, Ascaris lumbrichoides, Brugia malayi, Capillaria bovis, Capillaria plica, Capillaria feliscati, Cooperia oncophora, Cooperia punctata, Cyathostome species, Dictyocaulus filaria, Dictyocaulus viviparus, Dictyocaulus arnfieldi, Dirofiliaria immitis, Dracunculus insignis, Enterobius vermicularis, Haemonchus contortus, Haemonchus placei, Necator americanus, Nematodirus helvetianus, Oesophagostomum radiatum, Onchocerca volvulus, Onchocerca cervicalis, Ostertagia ostertagi, Ostertagia circumcincta, Oxyuris equi, Parascaris equorum, Strongyloides stercoralis, Strongylus vulgaris, Strongylus edentatus, Syngamus trachea, Teladorsagia circumcincta, Toxocara cati, Trichinella spiralis, Trichostrongylus axei, Trichostrongylus colubriformis, Trichuris vulpis, Trichuris suis, Trichurs trichiura, and Wuchereria bancrofti.

Further, a phosphoethanolamine n-methyltransferase-like sequence can be used to identify additional PEAMT-like sequence homologs within a genome. Multiple homologous copies of a PEAMT-like sequence can be present. For example, a nematode PEAMT-like sequence can be used as a seed sequence in an iterative PSI-BLAST search (default parameters, substitution matrix=Blosum62, gap open=11, gap extend=1) of a non redundant database such as wormpep (E value=1e-2, H value=1e-4, using, for example 4 iterations) to determine the number of homologs in a database, e.g., in a database containing the complete genome of an organism. A nematode PEAMT-like sequence can be present in a genome along with 1, 2, 3, 4, 5, 6, 8, 10, or more homologs.

Hybridization Methods. A nematode phosphoethanolamine n-methyltransferase-like sequence can be identified by a hybridization-based method using a sequence provided herein as a probe. For example, a library of nematode genomic or cDNA clones can be hybridized under low stringency conditions with the probe nucleic acid. Stringency conditions can be modulated to reduce background signal and increase signal from potential positives. Clones so identified can be sequenced to verify that they encode PEAMT-like sequences.

Another hybridization-based method utilizes an amplification reaction (e.g., the polymerase chain reaction (PCR)). Oligonucleotides, e.g., degenerate oligonucleotides, are designed to hybridize to a conserved region of a PEAMT-like sequence (e.g., a region conserved in the three nematode sequences depicted in FIG. 3). The oligonucleotides are used as primers to amplify a PEAMT-like sequence from template nucleic acid from a nematode, e.g., a nematode other than *A. suum, H. contortus, M. incognita, M. javanica* and *S. stercoralis* and/or *C. elegans*. The amplified fragment can be cloned and/or sequenced.

Complementation Methods. A nematode phosphoethanolamine n-methyltransferase-like sequence can be identified from a complementation screen for a nucleic acid molecule that restores PEAMT-like activity to a cell lacking a PEAMT-like activity. Routine methods can be used to construct strains (i.e., nematode strains) that lack specific enzymatic activities, e.g., PEAMT activity. For example, a nematode strain mutated at the PEAMT gene locus can be identified by selecting for resistance to inhibitory compounds. Such a strain can be transformed with a plasmid library expressing nematode cDNAs. Strains can be identified in which PEAMT activity is restored. For example, the PEAMT mutant strains transformed with the plasmid library can be exposed to allosteric inhibitors or other inhibitory compounds to select for strains that have acquired sensitivity to the inhibitors and are expressing a nematode PEAMT-like gene. The plasmid harbored by the strain can be recovered to identify and/or characterize the inserted nematode cDNA that provides PEAMT-like activity when expressed.

Full-length cDNA and Sequencing Methods. The following methods can be used, e.g., alone or in combination with another method described herein, to obtain full-length nematode PEAMT-like genes and determine their sequences.

Plant parasitic nematodes are maintained on greenhouse pot cultures depending on nematode preference. Root Knot Nematodes (*Meloidogyne* sp) are propagated on Rutgers tomato (Burpee), while Soybean Cyst Nematodes (*Heterodera* sp) are propagated on soybean. Total nematode RNA is isolated using the TRIZOL reagent (Gibco BRL). Briefly, 2 ml of packed worms are combined with 8 ml TRIZOL reagent and solubilized by vortexing. Following 5 minutes of incubation at room temperature, the samples are divided into smaller volumes and spun at 14,000×g for 10 minutes at 4° C. to remove insoluble material. The liquid phase is extracted with 200 µl of chloroform, and the upper aqueous phase is removed to a fresh tube. The RNA is precipitated by the addition of 500 µl of isopropanol and centrifuged to pellet. The aqueous phase is carefully removed, and the pellet is washed in 75% ethanol and spun to re-collect the RNA pellet. The supernatant is carefully removed, and the pellet is air dried for 10 minutes. The RNA pellet is resuspended in 50 µl of DEPC-$H_2O$ and analyzed by spectrophotometry at λ 260 and 280 nm to determine yield and purity. Yields can be 1-4 mg of total RNA from 2 ml of packed worms.

Full-length cDNAs can be generated using 5' and 3' RACE techniques in combination with EST sequence information. The molecular technique 5' RACE (Life Technologies, Inc., Rockville, Md.) can be employed to obtain complete or near-complete 5' ends of cDNA sequences for nematode PEAMT-like cDNA sequences. Briefly, following the instructions provided by Life Technologies, first strand cDNA is synthesized from total nematode RNA using Murine Leukemia Virus Reverse Transcriptase (M-MLV RT) and a gene specific "antisense" primer, e.g., designed from available EST sequence. RNase H is used to degrade the original mRNA template. The first strand cDNA is separated from unincorporated dNTPs, primers, and proteins using a GlassMAX Spin Cartridge. Terminal deoxynucleotidyl transferase (TdT) is used to generate a homopolymeric dC tailed extension by the sequential addition of dCTP nucleotides to the 3' end of the first strand cDNA. Following addition of the dC homopolymeric extension, the first strand cDNA is directly amplified without further purification using Taq DNA polymerase, a gene specific "antisense" primer designed from available EST sequences to anneal to a site located within the first strand cDNA molecule, and a deoxyinosine-containing primer that anneals to the homopolymeric dC tailed region of the cDNA in a polymerase chain reaction (PCR). 5' RACE PCR amplification products are cloned into a suitable vector for further analysis and sequencing.

The molecular technique, 3' RACE (Life Technologies, Inc., Rockville, Md.), can be employed to obtain complete or near-complete 3' ends of cDNA sequences for nematode PEAMT-like cDNA sequences. Briefly, following the instructions provided by Life Technologies (Rockville, Md.), first strand cDNA synthesis is performed on total nematode RNA using SuperScript™ Reverse Transcriptase and an oligo-dT primer that anneals to the polyA tail. Following degradation of the original mRNA template with RNase H, the first strand cDNA is directly PCR amplified without further purification using Taq DNA polymerase, a gene specific primer designed from available EST sequences to anneal to a site located within the first strand cDNA molecule, and a "universal" primer which contains sequence identity to 5' end of the oligo-dT primer. 3' RACE PCR amplification products are cloned into a suitable vector for further analysis and sequencing.

Nucleic Acid Variants

Isolated nucleic acid molecules of the present invention include nucleic acid molecules that have an open reading frame encoding a PEAMT-like polypeptide. Such nucleic acid molecules include molecules having: the sequences recited in SEQ ID NO: 1, 2, 3, 4, 5 and/or 6; and sequences coding for the PEAMT-like proteins recited in SEQ ID NO: 13, 14, 15, 16, 17 and/or 18. These nucleic acid molecules can be used, for example, in a hybridization assay to detect the presence of a *A. suum, H. contortus, M. incognita, M. javanica* and/or *S. stercoralis* nucleic acid in a sample.

The present invention includes nucleic acid molecules such as those shown in SEQ ID NO: 1, 2, 3, 4, 5 and/or 6 that may be subjected to mutagenesis to produce single or multiple nucleotide substitutions, deletions, or insertions. Nucleotide insertional derivatives of the nematode gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletion variants are characterized by the removal of one or more nucleotides from the sequence. Nucleotide substitution variants are those in which at least one nucleotide in the sequence has been removed and a different nucleotide inserted in its place. Such a substitution may be silent (e.g., synonymous), meaning that the substitution does not alter the amino acid defined by the codon. Alternatively, substitutions are designed to alter one amino acid for another amino acid (e.g., non-synonymous). A non-synonymous substitution can be conservative or non-conservative. A substitution can be such that activity, e.g., a PEAMT-like activity, is not impaired. A conservative amino acid substitution results in the alteration of an amino acid for a similar acting amino acid, or amino acid of like charge, polarity, or hydrophobicity, e.g., an amino acid substitution listed in Table 10 below. At some positions, even conservative amino acid substitutions can disrupt the activity of the polypeptide.

TABLE 10

Conservative Amino Acid Replacements

| Amino acid | Code | Replace with any of |
|---|---|---|
| Alanine | Ala | Gly, Cys, Ser |
| Arginine | Arg | Lys, His |
| Asparagine | Asn | Asp, Glu, Gln, |
| Aspartic Acid | Asp | Asn, Glu, Gln |
| Cysteine | Cys | Met, Thr, Ser |
| Glutamine | Gln | Asn, Glu, Asp |
| Glutamic Acid | Glu | Asp, Asn, Gln |
| Glycine | Gly | Ala |
| Histidine | His | Lys, Arg |
| Isoleucine | Ile | Val, Leu, Met |
| Leucine | Leu | Val, Ile, Met |
| Lysine | Lys | Arg, His |
| Methionine | Met | Ile, Leu, Val |
| Phenylalanine | Phe | Tyr, His, Trp |
| Proline | Pro | |
| Serine | Ser | Thr, Cys, Ala |
| Threonine | Thr | Ser, Met, Val |
| Tryptophan | Trp | Phe, Tyr |
| Tyrosine | Tyr | Phe, His |
| Valine | Val | Leu, Ile, Met |

The current invention also embodies splice variants of nematode PEAMT-like sequences.

Another aspect of the present invention embodies a polypeptide-encoding nucleic acid molecule that is capable of hybridizing under conditions of low stringency (or high stringency) to the nucleic acid molecule put forth in SEQ ID NO: 1, 2, 3, 4, 5 and/or 6, or their complements.

The nucleic acid molecules that encode for phosphoethanolamine n-methyltransferase-like polypeptides may correspond to the naturally occurring nucleic acid molecules or may differ by one or more nucleotide substitutions, deletions, and/or additions. Thus, the present invention extends to genes and any functional mutants, derivatives, parts, fragments, naturally occurring polymorphisms, homologs or analogs thereof or non-functional molecules. Such nucleic acid molecules can be used to detect polymorphisms of PEAMT genes or PEAMT-like genes, e.g., in other nematodes. As mentioned below, such molecules are useful as genetic probes; primer sequences in the enzymatic or chemical synthesis of the gene; or in the generation of immunologically interactive recombinant molecules. Using the information provided herein, such as the nucleotide sequence SEQ ID NO: 1, 2, 3, 4, 5 and/or 6, a nucleic acid molecule encoding a PEAMT-like molecule may be obtained using standard cloning and a screening techniques, such as a method described herein.

Nucleic acid molecules of the present invention can be in the form of RNA, such as mRNA, or in the form of DNA, including, for example, cDNA and genomic DNA obtained by cloning or produced synthetically. The DNA may be double-stranded or single-stranded. The nucleic acids may be in the form of RNA/DNA hybrids. Single-stranded DNA or RNA can be the coding strand, also referred to as the sense strand, or the non-coding strand, also known as the anti-sense strand.

One embodiment of the present invention includes a recombinant nucleic acid molecule, which includes at least one isolated nucleic acid molecule depicted in SEQ ID NO: 1, 2, 3, 4, 5, and/or 6, inserted in a vector capable of delivering and maintaining the nucleic acid molecule into a cell. The DNA molecule may be inserted into an autonomously replicating vector (suitable vectors include, for example, pGEM3Z and pcDNA3, and derivatives thereof). The vector nucleic acid may be a bacteriophage DNA such as bacteriophage lambda or M13 and derivatives thereof. The vector may be either RNA or DNA, single- or double-stranded, prokaryotic, eukaryotic, or viral. Vectors can include transposons, viral vectors, episomes, (e.g., plasmids), chromosomes inserts, and artificial chromosomes (e.g. BACs or YACs). Construction of a vector containing a nucleic acid described herein can be followed by transformation of a host cell such as a bacterium. Suitable bacterial hosts include, but are not limited to, E. coli. Suitable eukaryotic hosts include yeast such as S. cerevisiae, other fungi, vertebrate cells, invertebrate cells (e.g., insect cells), plant cells, human cells, human tissue cells, and whole eukaryotic organisms. (e.g., a transgenic plant or a transgenic animal). Further, the vector nucleic acid can be used to generate a virus such as vaccinia or baculovirus.

The present invention also extends to genetic constructs designed for polypeptide expression. Generally, the genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art and may be functional in, but are not limited to, a bacterium, yeast, plant, or animal cell. The expression vector can also include a translation regulatory sequence (e.g., an untranslated 5' sequence, an untranslated 3' sequence, a poly A addition site, or an internal ribosome entry site), a splicing sequence or splicing regulatory sequence, and a transcription termination sequence. The vector can be capable of autonomous replication or it can integrate into host DNA.

In an alternative embodiment, the DNA molecule is fused to a reporter gene such as β-glucuronidase gene, β-galactosidase (lacZ), chloramphenicol-acetyltransferase gene, a gene encoding green fluorescent protein (and variants thereof), or red fluorescent protein firefly luciferase gene, among others. The DNA molecule can also be fused to a nucleic acid encoding a polypeptide affinity tag, e.g. glutathione S-transferase (GST), maltose E binding protein, protein A, FLAG tag, hexa-histidine, or the influenza HA tag. The affinity tag or reporter fusion joins the reading frames of SEQ ID NO: 1, 2, 3, 4, 5 and/or 6 to the reading frame of the reporter gene encoding the affinity tag such that a translational fusion is generated. Expression of the fusion gene results in translation of a single polypeptide that includes both a nematode PEAMT-like region and reporter protein or affinity tag. The fusion can also join a fragment of the reading frame of SEQ ID NO: 1, 2, 3, 4, 5 and/or 6. The fragment can encode a functional region of the PEAMT-like polypeptides, a structurally intact domain, or an epitope (e.g., a peptide of about 8, 10, 20, or 30 or more amino acids). A nematode PEAMT-like nucleic acid that includes at least one of a regulatory region (e.g., a 5' regulatory region, a promoter, an enhancer, a 5' untranslated region, a translational start site, a 3' untranslated region, a polyadenylation site, or a 3' regulatory region) can also be fused to a heterologous nucleic acid. For example, the promoter of a PEAMT-like nucleic acid can be fused to a heterologous nucleic acid, e.g., a nucleic acid encoding a reporter protein.

Suitable cells to transform include any cell that can be transformed with a nucleic acid molecule of the present invention. A transformed cell of the present invention is also herein referred to as a recombinant or transgenic cell. Suitable cells can either be untransformed cells or cells that have already been transformed with at least one nucleic acid molecule. Suitable cells for transformation according to the present invention can either be: (i) endogenously capable of expressing the PEAMT-like protein or; (ii) capable of producing such protein after transformation with at least one nucleic acid molecule of the present invention.

In an exemplary embodiment, a nucleic acid of the invention is used to generate a transgenic nematode strain, e.g., a transgenic C. elegans strain. To generate such a strain, nucleic acid is injected into the gonad of a nematode, thus generating a heritable extrachromosomal array containing the nucleic acid (see, e.g., Mello et al. (1991) EMBO J. 10:3959-3970). The transgenic nematode can be propagated to generate a strain harboring the transgene. Nematodes of the strain can be used in screens to identify inhibitors specific for a A. suum, H. contortus, M. incognita, M. javanica and/or S. stercoralis PEAMT-like gene.

Oligonucleotides

Also provided are oligonucleotides that can form stable hybrids with a nucleic acid molecule of the present invention. The oligonucleotides can be about 10 to 200 nucleotides, about 15 to 120 nucleotides, or about 17 to 80 nucleotides in length, e.g., about 10, 20, 30, 40, 50, 60, 80, 100, 120 nucleotides in length. The oligonucleotides can be used as probes to identify nucleic acid molecules, primers to produce nucleic acid molecules, or therapeutic reagents to inhibit nematode PEAMT-like protein activity or production (e.g., antisense, triplex formation, ribozyme, and/or RNA drug-based reagents). The present invention includes oligonucleotides of RNA (ssRNA and dsRNA), DNA, or derivatives of either. The invention extends to the use of such oligonucleotides to protect non-nematode organisms (for example e.g., plants and animals) from disease by reading the viability of infecting nematodes, e.g., using a technology described herein. Appropriate oligonucleotide-containing therapeutic compositions can be administered to a non-nematode organism using techniques known to those skilled in the art, including, but not limited to, transgenic expression in plants or animals.

Primer sequences can be used to amplify a phosphoethanolamine n-methyltransferase-like nucleic acid or fragment thereof. For example, at least 10 cycles of PCR amplification can be used to obtain such an amplified nucleic acid. Primers can be at least about 8-40, 10-30 or 14-25 nucleotides in length, and can anneal to a nucleic acid "template molecule", e.g., a template molecule encoding an PEAMT-like genetic sequence, or a functional part thereof, or its complementary sequence. The nucleic acid primer molecule can be any nucleotide sequence of at least 10 nucleotides in length derived from, or contained within sequences depicted in SEQ ID NO: 1, 2, 3, 4, 5 and/or 6 and their complements. The nucleic acid template molecule may be in a recombinant form, in a virus particle, bacteriophage particle, yeast cell, animal cell, plant cell, fungal cell, or bacterial cell. A primer can be chemically synthesized by routine methods.

This invention embodies any phosphoethanolamine n-methyltransferase-like sequences that are used to identify and isolate similar genes from other organisms, including nematodes, prokaryotic organisms, and other eukaryotic organisms, such as other animals and/or plants.

In another embodiment, the invention provides oligonucleotides that are specific for a *A. suum, H. contortus, M. incognita, M. javanica* and/or *S. stercoralis* PEAMT-like nucleic acid molecule. Such oligonucleotides can be used in a PCR test to determine if a *A. suum, H. contortus, M. incognita, M. javanica* and/or *S. stercoralis* nucleic acid is present in a sample, e.g., to monitor a disease caused *A. suum, H. contortus, M. incognita, M. javanica* and/or *S. stercoralis*.

Protein Production

Isolated phosphoethanolamine n-methyltransferase-like proteins from nematodes can be produced in a number of ways, including production and recovery of the recombinant proteins and/or chemical synthesis of the protein. In one embodiment, an isolated nematode PEAMT-like protein is produced by culturing a cell, e.g., a bacterial, fungal, plant, or animal cell, capable of expressing the protein, under conditions for effective production and recovery of the protein. The nucleic acid can be operably linked to a heterologous promoter, e.g., an inducible promoter or a constitutive promoter. Effective growth conditions are typically, but not necessarily, in liquid media comprising salts, water, carbon, nitrogen, phosphate sources, minerals, and other nutrients, but may be any solution in which PEAMT-like proteins may be produced.

In one embodiment, recovery of the protein may refer to collecting the growth solution and need not involve additional steps of purification. Proteins of the present invention, however, can be purified using standard purification techniques, such as, but not limited to, affinity chromatography, thermaprecipitation, immunoaffinity chromatography, ammonium sulfate precipitation, ion exchange chromatography, filtration, electrophoresis, hydrophobic interaction chromatography, and others.

The phosphoethanolamine n-methyltransferase-like polypeptide can be fused to an affinity tag, e.g., a purification handle (e.g., glutathione-S-reductase, hexa-histidine, maltose binding protein, dihydrofolate reductases, or chitin binding protein) or an epitope tag (e.g., c-myc epitope tag, FLAG™ tag, or influenza HA tag). Affinity tagged and epitope tagged proteins can be purified using routine art-known methods.

Antibodies against Phosphoethanolamine n-Methyltransferase-Like Polypeptides

Recombinant phosphoethanolamine n-methyltransferase-like gene products or derivatives thereof can be used to produce immunologically interactive molecules, such as antibodies, or functional derivatives thereof. Useful antibodies include those that bind to a polypeptide that has substantially the same sequence as the amino acid sequences recited in SEQ ID NO: 7, 8, 9, 10, 11 and/or 12, or that has at least 60% similarity over 50 or more amino acids to these sequences. In a preferred embodiment, the antibody specifically binds to a polypeptide having the amino acid sequence recited in SEQ ID NO: 7, 8, 9, 10, 11 and/or 12. The antibodies can be antibody fragments and genetically engineered antibodies, including single chain antibodies or chimeric antibodies that can bind to more than one epitope. Such antibodies may be polyclonal or monoclonal and may be selected from naturally occurring antibodies or may be specifically raised to a recombinant PEAMT-like protein.

Antibodies can be derived by immunization with a recombinant or purified PEAMT-like gene or gene product. As used herein, the term "antibody" refers to an immunoglobulin, or fragment thereof. Examples of antibody fragments include F(ab) and F(ab')$_2$ fragments, particularly functional ones able to bind epitopes. Such fragments can be generated by proteolytic cleavage, e.g., with pepsin, or by genetic engineering. Antibodies can be polyclonal, monoclonal, or recombinant. In addition, antibodies can be modified to be chimeric, or humanized. Further, an antibody can be coupled to a label or a toxin.

Antibodies can be generated against a full-length PEAMT-like protein, or a fragment thereof, e.g., an antigenic peptide. Such polypeptides can be coupled to an adjuvant to improve immunogenicity. Polyclonal serum is produced by injection of the antigen into a laboratory animal such as a rabbit and subsequent collection of sera. Alternatively, the antigen is used to immunize mice. Lymphocytic cells are obtained from the mice and fused with myelomas to form hybridomas producing antibodies.

Peptides for generating phosphoethanolamine n-methyltransferase-like antibodies can be about 8, 10, 15, 20, 30 or more amino acid residues in length, e.g., a peptide of such length obtained from SEQ ID NO: 7, 8, 9, 10, 11 and/or 12. Peptides or epitopes can also be selected from regions exposed on the surface of the protein, e.g., hydrophilic or amphipathic regions. An epitope in the vicinity of the active or binding site can be selected such that an antibody binding such an epitope would block access to the active site or prevent binding. Antibodies reactive with, or specific for, any of these regions, or other regions or domains described herein are provided. An antibody to a PEAMT-like protein can modulate a PEAMT-like activity.

Monoclonal antibodies, which can be produced by routine methods, are obtained in abundance and in homogenous form from hybridomas formed from the fusion of immortal cell lines (e.g., myelomas) with lymphocytes immunized with PEAMT-like polypeptides such as those set forth in SEQ ID NO: 7, 8, 9, 10, 11 and/or 12.

In addition, antibodies can be engineered, e.g., to produce a single chain antibody (see, for example, Colcher et al. (1999) *Ann N Y Acad Sci* 880: 263-280; and Reiter (1996) *Clin Cancer Res* 2: 245-252). In still another implementation, antibodies are selected or modified based on screening procedures, e.g., by screening antibodies or fragments thereof from a phage display library.

Antibodies of the present invention have a variety of important uses within the scope of this invention. For example, such antibodies can be used: (i) as therapeutic compounds to passively immunize an animal in order to protect the animal from nematodes susceptible to antibody treatment; (ii) as reagents in experimental assays to detect presence of nematodes; (iii) as tools to screen for expression of the gene product in nematodes, animals, fungi, bacteria, and plants; and/or (iv) as a purification tool of PEAMT-like protein; (v) as PEAMT inhibitors/activators that can be expressed or introduced into plants or animals for therapeutic purposes.

An antibody against a phosphoethanolamine n-methyltransferase-like protein can be produced in a plant cell, e.g., in a transgenic plant or in culture (see, e.g., U.S. Pat. No. 6,080,560).

Antibodies that specifically recognize a *A. suum, H. contortus, M. incognita, M. javanica* and/or *S. stercoralis* PEAMT-like proteins can be used to identify *A. suum, H. contortus, M. incognita, M. javanica* and/or *S. stercoralis* nematodes, and, thus, can be used to monitor a disease caused by *A. suum, H. contortus, M. incognita, M. javanica* and/or *S. stercoralis*.

Nucleic Acids Agents

Also featured are isolated nucleic acids that are antisense to nucleic acids encoding nematode phosphoethanolamine n-methyltransferase-like proteins. An "antisense" nucleic acid includes a sequence that is complementary to the coding strand of a nucleic acid encoding a PEAMT-like protein. The complementarity can be in a coding region of the coding strand or in a noncoding region, e.g., a 5' or 3' untranslated region, e.g., the translation start site. The antisense nucleic acid can be produced from a cellular promoter (e.g., a RNA polymerase II or III promoter), or can be introduced into a cell, e.g., using a liposome. For example, the antisense nucleic acid can be a synthetic oligonucleotide having a length of about 10, 15, 20, 30, 40, 50, 75, 90, 120 or more nucleotides in length.

An antisense nucleic acid can be synthesized chemically or produced using enzymatic reagents, e.g., a ligase. An antisense nucleic acid can also incorporate modified nucleotides, and artificial backbone structures, e.g., phosphorothioate derivative, and acridine substituted nucleotides.

Ribozymes. The antisense nucleic acid can be a ribozyme. The ribozyme can be designed to specifically cleave RNA, e.g., a PEAMT-like mRNA. Methods for designing such ribozymes are described in U.S. Pat. No. 5,093,246 or Haselhoff and Gerlach (1988) *Nature* 334:585-591. For example, the ribozyme can be a derivative of Tetrahymena L-19 IVS RNA in which the nucleotide sequence of the active site is modified to be complementary to a PEAMT-like nucleic acid (see, e.g., Cech et al. U.S. Pat. No. 4,987,071; and Cech et al. U.S. Pat. No. 5,116,742).

Peptide Nucleic acid (PNA). An antisense agent directed against an phosphoethanolamine n-methyltransferase-like nucleic acid can be a peptide nucleic acid (PNA). See Hyrup et al. (1996) *Bioorganic & Medicinal Chemistry* 4: 5-23) for methods and a description of the replacement of the deoxyribose phosphate backbone for a pseudopeptide backbone. A PNA can specifically hybridize to DNA and RNA under conditions of low ionic strength as a result of its electrostatic properties. The synthesis of PNA oligomers can be performed using standard solid phase peptide synthesis protocols as described in Hyrup et al. (1996) supra and Perry-O'Keefe et al. *Proc. Natl. Acad. Sci.* 93: 14670-14675.

RNA Mediated Interference (RNAi). A double stranded RNA (dsRNA) molecule can be used to inactivate a phosphoethanolamine n-methyltransferase-like gene in a cell by a process known as RNA mediated-interference (RNAi; e.g., Fire et al. (1998) *Nature* 391:806-811, and Gönczy et al. (2000) *Nature* 408:331-336). The dsRNA molecule can have the nucleotide sequence of a PEAMT-like nucleic acid described herein or a fragment thereof. The molecule can be injected into a cell, or a syncytium, e.g., a nematode gonad as described in Fire et al., supra.

Screening Assays

Another embodiment of the present invention is a method of identifying a compound capable of altering (e.g., inhibiting or enhancing) the activity of PEAMT-like molecules. This method, also referred to as a "screening assay," herein, includes, but is not limited to, the following procedure: (i) contacting an isolated PEAMT-like protein with a test inhibitory compound under conditions in which, in the absence of the test compound, the protein has PEAMT-like activity; and (ii) determining if the test compound alters the PEAMT-like activity. Suitable inhibitors or activators that alter a nematode PEAMT-like activity include compounds that interact directly with a nematode PEAMT-like protein, perhaps but not necessarily, in the active or binding site. They can also interact with other regions of the nematode PEAMT protein by binding to regions outside of the active site or site responsible for regulation, for example, by allosteric interaction.

In one embodiment the *A. suum, H. contortus, M. incognita, M. javanica* or *S. stercoralis* PEAMT is expressed in a yeast or bacterial cell and then purified and screened in a TLC based radioactivity assay (Bolognese & McGraw (2000) *Plant Physiol.* 124(4):1800-13; Nuccio et al. (2000) *J Biol Chem.* 275(19):14095-101; Charron et al. (2002) *Plant Physiol.* 129(1):363-73). $^{14}$C-labelled S-adenosyl-methionine ($^{14}$C-SAM) co-factor is used and the conversion of phosphoethanolamine (pEA), phosphomonomethylethanolamine (pMME), or phosphodimethylethanolamine (pDME) to $^{14}$C-labelled pMME, pDME or phosphocholine (pCho) is monitored after TLC separation. Compounds that decrease the conversion of pEA, pMME or pDME to pMME, pDME or pCho are candidate PEAMT inhibitors.

Compounds. A test compound can be a large or small molecule, for example, an organic compound with a molecular weight of about 100 to 10,000; 200 to 5,000; 200 to 2000; or 200 to 1,000 daltons. A test compound can be any chemical compound, for example, a small organic molecule, a carbohydrate, a lipid, an amino acid, a polypeptide, a nucleoside, a nucleic acid, or a peptide nucleic acid. Small molecules include, but are not limited to, metabolites, metabolic analogues, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds). Compounds and components for synthesis of compounds can be obtained from a commercial chemical supplier, e.g., Sigma-Aldrich Corp. (St. Louis, Mo.). The test compound or compounds can be naturally occurring, synthetic, or both. A test compound can be the only substance assayed by the method described herein. Alternatively, a collection of test compounds can be assayed either consecutively or concurrently by the methods described herein.

Compounds can also act by allosteric inhibition or directly by preventing the substrate phosphoethanolamine, phosphomonomethylethanolamine, phosphodimethylethanolamine or the cofactor S-adenosylmethionine from binding to the enzyme, and thus, regulating its target, i.e., a phosphoethanolamine n-methyltransferase.

A high-throughput method can be used to screen large libraries of chemicals. Such libraries of candidate compounds can be generated or purchased, e.g., from Chembridge Corp. (San Diego, Calif.). Libraries can be designed to cover a diverse range of compounds. For example, a library can include 10,000, 50,000, or 100,000 or more unique compounds. Merely by way of illustration, a library can be constructed from heterocycles including pyridines, indoles, quinolines, furans, pyrimidines, triazines, pyrroles, imidazoles, naphthalenes, benzimidazoles, piperidines, pyrazoles, benzoxazoles, pyrrolidines, thiphenes, thiazoles, benzothiazoles, and morpholines. A library can be designed and synthesized to cover such classes of chemicals, e.g., as described in DeWitt et al. (1993) *Proc. Natl. Acad. Sci. U.S.A.* 90:6909-6913; Erb et al. (1994) *Proc. Natl. Acad. Sci. USA* 91:11422-11426; Zuckermann et al. (1994) *J. Med. Chem.* 37:2678-2685; Cho et al. (1993) *Science* 261:1303-1305; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233-1251.

Organism-based Assays. Organisms can be grown in microtiter plates, e.g., 6-well, 32-well, 64-well, 96-well, 384-well plates.

In one embodiment, the organism is a nematode. The nematodes can be genetically modified. Non-limiting examples of such modified nematodes include: 1) nematodes or nematode cells (*A. suum, H. contortus, M. incognita, M. javanica, S. stercoralis*, and/or *C. elegans*) having one or more PEAMT-like genes inactivated (e.g., using RNA mediated interference); 2) nematodes or nematode cells expressing a heterologous PEAMT-like gene, e.g., an PEAMT-like gene from another species; and 3) nematodes or nematode cells having one or more endogenous PEAMT-like genes inactivated and expressing a heterologous PEAMT-like gene, e.g., a *A. suum, H. contortus, M. incognita, M. javanica* and/or *S. stercoralis* PEAMT-like gene as described herein.

A plurality of candidate compounds, e.g., a combinatorial library, can be screened. The library can be provided in a format that is amenable for robotic manipulation, e.g., in microtitre plates. Compounds can be added to the wells of the microtiter plates. Following compound addition and incubation, viability and/or reproductive properties of the nematodes or nematode cells are monitored.

The compounds can also be pooled, and the pools tested. Positive pools are split for subsequent analysis. Regardless of the method, compounds that decrease the viability or reproductive ability of nematodes, nematode cells, or progeny of the nematodes are considered lead compounds.

In another embodiment, the compounds can be tested on a microorganism or a eukaryotic or mammalian cell line, e.g., rabbit skin cells, Chinese hamster ovary cells (CHO), and/or Hela cells. For example, CHO cells absent for PEAMT-like genes, but expressing a nematode PEAMT-like gene can be used. The generation of such strains is routine in the art. As described above for nematodes and nematode cells, the cell lines can be grown in microtitre plates, each well having a different candidate compound or pool of candidate compounds. Growth is monitored during or after the assay to determine if the compound or pool of compounds is a modulator of a nematode PEAMT-like polypeptide.

In Vitro Activity Assays. The screening assay can be an in vitro activity assay. For example, a nematode phosphoethanolamine n-methyltransferase-like polypeptide can be purified as described above. The polypeptide can be disposed in an assay container, e.g., a well of a microtitre plate. A candidate compound can be added to the assay container, and the PEAMT-like activity is measured. Optionally, the activity is compared to the activity measured in a control container in which no candidate compound is disposed or in which an inert or non-functional compound is disposed In Vitro Binding Assays. The screening assay can also be a cell-free binding assay, e.g., an assay to identify compounds that bind a nematode PEAMT-like polypeptide. For example, a nematode PEAMT-like polypeptide can be purified and labeled. The labeled polypeptide is contacted to beads; each bead has a tag detectable by mass spectroscopy, and test compound, e.g., a compound synthesized by combinatorial chemical methods. Beads to which the labeled polypeptide is bound are identified and analyzed by mass spectroscopy. The beads can be generated using "split-and-pool" synthesis. The method can further include a second assay to determine if the compound alters the activity of the PEAMT-like polypeptide.

Optimization of a Compound. Once a lead compound has been identified, standard principles of medicinal chemistry can be used to produce derivatives of the compound. Derivatives can be screened for improved pharmacological properties, for example, efficacy, pharmacokinetics, stability, solubility, and clearance. The moieties responsible for a compound's activity in the above-described assays can be delineated by examination of structure-activity relationships (SAR) as is commonly practiced in the art. One can modify moieties on a lead compound and measure the effects of the modification on the efficacy of the compound to thereby produce derivatives with increased potency. For an example, see Nagarajan et al. (1988) *J. Antibiot.* 41:1430-1438. A modification can include N-acylation, amination, amidation, oxidation, reduction, alkylation, esterification, and hydroxylation. Furthermore, if the biochemical target of the lead compound is known or determined, the structure of the target and the lead compound can inform the design and optimization of derivatives. Molecular modeling software to do this is commercially available (e.g., Molecular Simulations, Inc.). "SAR by NMR," as described in Shuker et al. (1996) *Science* 274:1531-1534, can be used to design ligands with increased affinity, by joining lower-affinity ligands.

A preferred compound is one that interferes with the function of a phosphoethanolamine n-methyltransferase-like polypeptide and that is not substantially toxic to plants, animals, or humans. By "not substantially toxic" it is meant that the compound does not substantially affect the respective animal, or human PEAMT proteins or phosphoethanolamine n-methyltransferase activity. Thus, particularly desirable inhibitors of *A. suum, H. contortus, M. incognita, M. javanica* and/or *S. stercoralis* PEAMT do not substantially inhibit non-nematode PEAMT-like polypeptides or phosphatidylethanolamine n-methyltransferase activity of vertebrates, e.g., humans for example. Other desirable compounds do not substantially inhibit to phosphoethanolamine n-methyltransferase activity of plants such as tomato (GenBank® Identification No: 12584943), spinach (GenBank® Identification No: 7407189), or wheat (GenBank® Identification No: 17887465).

Standard pharmaceutical procedures can be used to assess the toxicity and therapeutic efficacy of a modulator of a PEAMT-like activity. The LD50 (the dose lethal to 50% of the population) and the ED50 (the dose therapeutically effective in 50% of the population can be measured in cell cultures, experimental plants (e.g., in laboratory or field studies), or experimental animals. Optionally, a therapeutic index can be determined which is expressed as the ratio: LD50/ED50. High therapeutic indices are indicative of a compound being an effective PEAMT-like inhibitor, while not causing undue toxicity or side effects to a subject (e.g., a host plant or host animal).

Alternatively, the ability of a candidate compound to modulate a non-nematode phosphoethanolamine n-methyltransferase-like polypeptide is assayed, e.g., by a method described herein. For example, the inhibition constant of a candidate compound for a mammalian PEAMT-like polypeptide can be measured and compared to the inhibition constant for a nematode PEAMT-like polypeptide.

The aforementioned analyses can be used to identify and/or design a modulator with specificity for nematode phosphoethanolamine n-methyltransferase-like polypeptide over vertebrate or other animal (e.g., mammalian) phosphatidylethanolamine n-methyltransferase-like polypeptides. Suitable nematodes to target are any nematodes with the PEAMT-like proteins or proteins that can be targeted by a compound that otherwise inhibits, reduces, activates, or generally affects the activity of nematode PEAMT proteins.

Inhibitors of nematode phosphoethanolamine n-methyltransferase-like proteins can also be used to identify phosphoethanolamine n-methyltransferase-like proteins in the nematode or other organisms using procedures known in the art, such as affinity chromatography. For example, a specific antibody may be linked to a resin and a nematode extract passed over the resin, allowing any PEAMT-like proteins that bind the antibody to bind the resin. Subsequent biochemical techniques familiar to those skilled in the art can be performed to purify and identify bound PEAMT-like proteins.

Agricultural Compositions

A compound that is identified as a phosphoethanolamine n-methyltransferase-like polypeptide inhibitor can be formulated as a composition that is applied to plants, soil, or seeds in order to confer nematode resistance. The composition can be prepared in a solution, e.g., an aqueous solution, at a concentration from about 0.005% to 10%, or about 0.01% to 1%, or about 0.1% to 0.5% by weight. The solution can include an organic solvent, e.g., glycerol or ethanol. The composition can be formulated with one or more agriculturally acceptable carriers. Agricultural carriers can include: clay, talc, bentonite, diatomaceous earth, kaolin, silica, benzene, xylene, toluene, kerosene, N-methylpyrrolidone, alcohols (methanol, ethanol, isopropanol, n-butanol, ethylene glycol, propylene glycol, and the like), and ketones (acetone, methylethyl ketone, cyclohexanone, and the like). The formulation can optionally further include stabilizers, spreading agents, wetting extenders, dispersing agents, sticking agents, disintegrators, and other additives, and can be prepared as a liquid, a water-soluble solid (e.g., tablet, powder or granule), or a paste.

Prior to application, the solution can be combined with another desired composition such as another anthelmintic agent, germicide, fertilizer, plant growth regulator and the like. The solution may be applied to the plant tissue, for example, by spraying, e.g., with an atomizer, by drenching, by pasting, or by manual application, e.g., with a sponge. The solution can also be distributed from an airborne source, e.g., an aircraft or other aerial object, e.g., a fixture mounted with an apparatus for spraying the solution, the fixture being of sufficient height to distribute the solution to the desired plant tissues. Alternatively, the composition can be applied to plant tissue from a volatile or airborne source. The source is placed in the vicinity of the plant tissue and the composition is dispersed by diffusion through the atmosphere. The source and the plant tissue to be contacted can be enclosed in an incubator, growth chamber, or greenhouse, or can be in sufficient proximity that they can be outdoors.

If the composition is distributed systemically thorough the plant, the composition can be applied to tissues other than the leaves, e.g., to the stems or roots. Thus, the composition can be distributed by irrigation. The composition can also be injected directly into roots or stems.

A skilled artisan would be able to determine an appropriate dosage for formulation of the active ingredient of the composition. For example, the ED50 can be determined as described above from experimental data. The data can be obtained by experimentally varying the dose of the active ingredient to identify a dosage effective for killing a nematode, while not causing toxicity in the host plant or host animal (i.e. non-nematode animal).

A number of embodiments of the invention have been described. Nevertheless, it will be understood that various modifications may be made without departing from the spirit and scope of the invention. Accordingly, other embodiments are within the scope of the following claims.

What is claimed is:

1. A purified polypeptide comprising an amino acid sequence that is at least 95% identical to the amino acid sequence of SEQ ID NO:7, wherein the polypeptide has methyltransferase activity.

2. A purified polypeptide comprising an amino acid sequence that is at least 98% identical to the amino acid sequence of SEQ ID NO:7, wherein the polypeptide has methyltransferase activity.

3. A purified polypeptide comprising the amino acid sequence of SEQ ID NO:7.

* * * * *